(12) United States Patent
Shuber et al.

(10) Patent No.: US 7,776,524 B2
(45) Date of Patent: Aug. 17, 2010

(54) METHODS FOR ANALYSIS OF MOLECULAR EVENTS

(75) Inventors: Anthony P. Shuber, Mendon, MA (US); Lisa Kann, Arlington, MA (US); Duncan Whitney, Sudbury, MA (US)

(73) Assignee: Genzyme Corporation, Cambridge, MA (US)

( * ) Notice: Subject to any disclaimer, the term of this patent is extended or adjusted under 35 U.S.C. 154(b) by 1446 days.

(21) Appl. No.: 10/369,123

(22) Filed: Feb. 18, 2003

(65) Prior Publication Data

US 2003/0203382 A1 Oct. 30, 2003

Related U.S. Application Data

(60) Provisional application No. 60/357,585, filed on Feb. 15, 2002.

(51) Int. Cl.
    C12Q 1/68 (2006.01)
(52) U.S. Cl. ......................................................... 435/6
(58) Field of Classification Search ...................... 435/6
    See application file for complete search history.

(56) References Cited

U.S. PATENT DOCUMENTS

| | | | |
|---|---|---|---|
| 3,413,464 A | 11/1968 | Hetensky | |
| 4,072,574 A | 2/1978 | Loeb et al. | |
| 4,101,279 A | 7/1978 | Aslam | |
| 4,309,782 A | 1/1982 | Paulin | |
| 4,333,734 A | 6/1982 | Fleisher | |
| 4,358,535 A | 11/1982 | Falkow et al. | |
| 4,445,235 A | 5/1984 | Slover et al. | |
| 4,535,058 A | 8/1985 | Weinberg et al. | |
| 4,578,358 A | 3/1986 | Oksman et al. | |
| 4,683,195 A | 7/1987 | Mullis et al. | |
| 4,683,202 A | 7/1987 | Mullis | |
| 4,705,050 A | 11/1987 | Markham | |
| 4,735,905 A | 4/1988 | Parker | |
| 4,786,718 A | 11/1988 | Weinberg et al. | |
| 4,857,300 A | 8/1989 | Maksem | |
| 4,863,849 A | 9/1989 | Melamede | |
| 4,871,838 A | 10/1989 | Bos et al. | |
| 4,935,342 A | 6/1990 | Seligson et al. | |
| 4,968,602 A | 11/1990 | Dattagupta | |
| 4,968,603 A | 11/1990 | Slamon et al. | |
| 4,981,783 A | 1/1991 | Augenlicht | |
| 4,982,615 A | 1/1991 | Sultan et al. | |
| 4,988,617 A | 1/1991 | Landegren et al. | |
| 5,075,217 A | 12/1991 | Weber | |
| 5,087,617 A | 2/1992 | Smith | |
| 5,126,239 A | 6/1992 | Livak et al. | |
| 5,137,806 A | 8/1992 | LeMaistre et al. | |
| 5,141,849 A | 8/1992 | Chou | |
| 5,149,506 A | 9/1992 | Skiba et al. | |
| 5,185,244 A | 2/1993 | Wallace | |
| 5,196,167 A | 3/1993 | Guadagno et al. | |
| 5,200,314 A | 4/1993 | Urdea | |
| 5,202,231 A | 4/1993 | Drmanac et al. | |
| 5,248,671 A | 9/1993 | Smith | |
| 5,272,057 A | 12/1993 | Smulson et al. | |
| 5,296,349 A | 3/1994 | Wallace | |
| 5,302,509 A | 4/1994 | Cheeseman | |
| 5,330,892 A | 7/1994 | Vogelstein et al. | |
| 5,331,973 A | 7/1994 | Fiedler et al. | |
| 5,348,855 A | 9/1994 | Dattagupta et al. | |
| 5,352,775 A | 10/1994 | Albertsen et al. | |
| 5,362,623 A | 11/1994 | Vogelstein et al. | |
| 5,369,004 A | 11/1994 | Polymeropoulos et al. | |
| 5,378,602 A | 1/1995 | Polymeropoulos et al. | |
| 5,380,645 A | 1/1995 | Vogelstein | |
| 5,380,647 A | 1/1995 | Bahar | |
| 5,382,510 A | 1/1995 | Levine et al. | |
| 5,409,586 A | 4/1995 | Kamahori et al. | |
| 5,416,025 A | 5/1995 | Krepinsky et al. | |
| 5,455,166 A | 10/1995 | Walker | |
| 5,458,761 A | 10/1995 | Kamahori et al. | |
| 5,463,782 A | 11/1995 | Carlson et al. | |
| 5,466,576 A | 11/1995 | Schulz et al. | |
| 5,468,610 A | 11/1995 | Polymeropoulos et al. | |
| 5,468,613 A | 11/1995 | Erlich et al. | |
| 5,482,834 A | 1/1996 | Gillespie | |
| 5,489,508 A | 2/1996 | West et al. | |
| 5,492,808 A | 2/1996 | de la Chapelle et al. | |
| 5,496,470 A | 3/1996 | Lenhart | |
| 5,496,699 A | 3/1996 | Sorenson | |

(Continued)

FOREIGN PATENT DOCUMENTS

AU          A-11325/95          10/1994

(Continued)

OTHER PUBLICATIONS

Gardner and Jack, Nucleic acids research, vol. 30, No. 2, pp. 605-613, Jan. 2002.*

(Continued)

*Primary Examiner*—Gary Benzion
*Assistant Examiner*—Cynthia B Wilder
(74) *Attorney, Agent, or Firm*—Fangli Chen

(57) ABSTRACT

Methods and compositions are provided for detecting the presence of nucleic acid sequence variants in a subpopulation of nucleic acid molecules in a biological sample. These methods are particularly useful for identifying individuals with mutations indicative of cancer.

13 Claims, 2 Drawing Sheets

U.S. PATENT DOCUMENTS

| | | | |
|---|---|---|---|
| 5,506,105 A | 4/1996 | Haydock | |
| 5,508,164 A | 4/1996 | Kausch et al. | |
| 5,512,441 A | 4/1996 | Ronal | |
| 5,514,547 A | 5/1996 | Balazs et al. | |
| 5,527,676 A | 6/1996 | Vogelstein et al. | |
| 5,532,108 A | 7/1996 | Vogelstein | |
| 5,538,851 A | 7/1996 | Fach et al. | |
| 5,545,527 A | 8/1996 | Stevens et al. | |
| 5,552,283 A | 9/1996 | Diamandis et al. | |
| 5,559,014 A | 9/1996 | Estes et al. | |
| 5,561,041 A | 10/1996 | Sidransky | |
| 5,569,584 A | 10/1996 | Augenlicht | |
| 5,571,676 A | 11/1996 | Shuber | |
| 5,578,458 A | 11/1996 | Caskey et al. | |
| 5,580,729 A | 12/1996 | Vogelstein | |
| 5,589,330 A | 12/1996 | Shuber | |
| 5,589,335 A | 12/1996 | Kearney et al. | |
| 5,599,662 A | 2/1997 | Respess | |
| 5,604,099 A | 2/1997 | Erlich et al. | |
| 5,610,287 A | 3/1997 | Nikiforov et al. | |
| 5,612,473 A | 3/1997 | Wu et al. | |
| 5,616,463 A | 4/1997 | Fornace, Jr. et al. | |
| 5,627,032 A | 5/1997 | Ulanovsky | |
| 5,633,134 A | 5/1997 | Shuber | |
| 5,635,347 A | 6/1997 | Link et al. | |
| 5,635,352 A | 6/1997 | Urdea et al. | |
| 5,641,628 A | 6/1997 | Bianchi | |
| 5,645,995 A | 7/1997 | Kieback | |
| 5,648,212 A | 7/1997 | Albertson et al. | |
| 5,650,277 A | 7/1997 | Navot et al. | |
| 5,650,281 A | 7/1997 | Vogelstein | |
| 5,670,325 A | 9/1997 | Lapidus et al. | |
| 5,683,877 A | 11/1997 | Lu-Chang et al. | |
| 5,687,716 A | 11/1997 | Kaufmann et al. | |
| 5,688,643 A | 11/1997 | Oka et al. | |
| 5,709,998 A | 1/1998 | Kinzler et al. | |
| 5,710,028 A | 1/1998 | Eyal et al. | |
| 5,726,019 A | 3/1998 | Sidransky | |
| 5,741,650 A | 4/1998 | Lapidus et al. | |
| 5,753,439 A | 5/1998 | Smith et al. | |
| 5,759,777 A | 6/1998 | Kearney et al. | |
| 5,798,266 A | 8/1998 | Quay et al. | |
| 5,800,347 A | 9/1998 | Skates et al. | |
| 5,830,665 A | 11/1998 | Shuber et al. | |
| 5,834,181 A | 11/1998 | Shuber | |
| 5,834,193 A | 11/1998 | Kozlowski et al. | |
| 5,846,710 A | 12/1998 | Bajaj | |
| 5,856,092 A | 1/1999 | Dale et al. | |
| 5,856,104 A | 1/1999 | Chee et al. | |
| 5,866,323 A | 2/1999 | Markowitz et al. | |
| 5,882,865 A | 3/1999 | Vogelstein et al. | |
| 5,885,775 A | 3/1999 | Haff et al. | |
| 5,888,778 A | 3/1999 | Shuber | |
| 5,888,819 A | 3/1999 | Goelet et al. | |
| 5,910,407 A | 6/1999 | Vogelstein et al. | |
| 5,916,744 A | 6/1999 | Taylor | |
| 5,928,870 A | 7/1999 | Lapidus et al. | |
| 5,942,396 A | 8/1999 | Shiff et al. | |
| 5,945,284 A | 8/1999 | Livak et al. | |
| 5,952,178 A | 9/1999 | Lapidus et al. | |
| 5,958,684 A | 9/1999 | Van Leeuwen et al. | |
| 5,976,798 A * | 11/1999 | Parker et al. | 435/6 |
| 5,976,800 A | 11/1999 | Lau et al. | |
| 5,976,842 A * | 11/1999 | Wurst | 435/91.2 |
| 5,981,180 A | 11/1999 | Chandler et al. | |
| 6,013,431 A | 1/2000 | Soderlund et al. | |
| 6,017,704 A | 1/2000 | Herman et al. | |
| 6,020,124 A | 2/2000 | Sorenson | |
| 6,020,137 A | 2/2000 | Lapidus et al. | |
| 6,037,465 A | 3/2000 | Hillebrand et al. | |
| 6,084,091 A | 7/2000 | Muller et al. | |
| 6,100,029 A | 8/2000 | Lapidues et al. | |
| 6,100,040 A | 8/2000 | Ramberg | |
| 6,107,032 A | 8/2000 | Kilger et al. | |
| 6,107,061 A * | 8/2000 | Johnson | 435/91.1 |
| 6,110,678 A | 8/2000 | Weisburg et al. | |
| 6,114,114 A | 9/2000 | Seilhamer et al. | |
| 6,130,049 A | 10/2000 | Paul et al. | |
| 6,143,529 A | 11/2000 | Lapidus et al. | |
| 6,146,828 A | 11/2000 | Lapidus et al. | |
| 6,150,100 A | 11/2000 | Ruschoff et al. | |
| 6,150,117 A | 11/2000 | Zetter et al. | |
| 6,153,379 A | 11/2000 | Caskey et al. | |
| 6,156,504 A | 12/2000 | Gocke et al. | |
| 6,177,251 B1 | 1/2001 | Vogelstein et al. | |
| 6,180,408 B1 | 1/2001 | Kwok et al. | |
| 6,203,993 B1 | 3/2001 | Suber et al. | |
| 6,214,187 B1 | 4/2001 | Hammond et al. | |
| 6,214,558 B1 | 4/2001 | Shuber et al. | |
| 6,221,592 B1 | 4/2001 | Schwartz et al. | |
| 6,225,092 B1 | 5/2001 | Kilger et al. | |
| 6,228,596 B1 | 5/2001 | Macina et al. | |
| 6,235,474 B1 | 5/2001 | Feinberg | |
| 6,235,486 B1 | 5/2001 | Young et al. | |
| 6,238,927 B1 | 5/2001 | Abrams et al. | |
| 6,251,638 B1 | 6/2001 | Umansky et al. | |
| 6,251,660 B1 | 6/2001 | Muir et al. | |
| 6,258,540 B1 | 7/2001 | Lo et al. | |
| 6,265,229 B1 | 7/2001 | Fodstad et al. | |
| 6,268,136 B1 | 7/2001 | Shuber et al. | |
| 6,280,947 B1 | 8/2001 | Shuber et al. | |
| 6,300,077 B1 | 10/2001 | Shuber et al. | |
| 6,303,304 B1 | 10/2001 | Shuber et al. | |
| 6,312,893 B1 | 11/2001 | Van Ness et al. | |
| 6,351,857 B2 | 3/2002 | Sloan et al. | |
| 6,355,433 B1 | 3/2002 | Xu et al. | |
| 6,361,940 B1 | 3/2002 | Van Ness et al. | |
| 6,406,857 B1 | 6/2002 | Shuber et al. | |
| 6,415,455 B1 | 7/2002 | Sloan et al. | |
| 6,415,555 B1 | 7/2002 | Montague | |
| 6,428,964 B1 | 8/2002 | Shuber | |
| 6,448,002 B1 | 9/2002 | Hillebrand et al. | |
| 6,458,544 B1 | 10/2002 | Miller | |
| 6,475,738 B2 | 11/2002 | Shuber et al. | |
| 6,482,595 B2 | 11/2002 | Shuber et al. | |
| 6,498,012 B2 | 12/2002 | Laken | |
| 6,503,718 B2 | 1/2003 | Shuber et al. | |
| 6,518,026 B2 | 2/2003 | Hartley | |
| 6,534,273 B2 | 3/2003 | Weisburg et al. | |
| 6,551,777 B1 | 4/2003 | Shuber et al. | |
| 6,566,101 B1 * | 5/2003 | Shuber et al. | 435/91.2 |
| 6,586,177 B1 | 7/2003 | Shuber | |
| 6,605,433 B1 | 8/2003 | Fliss et al. | |
| 6,818,404 B2 | 11/2004 | Shuber | |
| 6,844,155 B2 | 1/2005 | Shuber | |
| 6,849,403 B1 | 2/2005 | Shuber | |
| 6,919,174 B1 | 7/2005 | Shuber | |
| 6,964,846 B1 | 11/2005 | Shuber | |
| 7,368,233 B2 | 5/2008 | Shuber et al. | |
| 7,432,050 B2 | 10/2008 | Markowitz | |
| 7,485,420 B2 | 2/2009 | Markowitz | |
| 2001/0018180 A1 | 8/2001 | Shuber et al. | 435/6 |
| 2001/0039012 A1 | 11/2001 | Lapidus | 435/6 |
| 2001/0042264 A1 | 11/2001 | Sloan et al. | 4/315 |
| 2002/0001800 A1 | 1/2002 | Lapidus | 435/6 |
| 2002/0004201 A1 | 1/2002 | Lapidus et al. | 435/6 |
| 2002/0009727 A1 | 1/2002 | Schultz et al. | |
| 2002/0012922 A1 | 1/2002 | Hilbush et al. | |
| 2002/0025525 A1 | 2/2002 | Shuber | 435/6 |
| 2002/0040498 A1 | 4/2002 | Sloan et al. | 4/315 |
| 2002/0045183 A1 | 4/2002 | Shuber et al. | 435/6 |
| 2002/0048752 A1 | 4/2002 | Lapidus et al. | 435/6 |
| 2002/0064787 A1 | 5/2002 | Shuber et al. | 435/6 |
| 2002/0102604 A1 | 8/2002 | Edwards et al. | |

| | | | |
|---|---|---|---|
| 2002/0110810 A1 | 8/2002 | Shuber | 435/6 |
| 2002/0119469 A1 | 8/2002 | Shuber et al. | 435/6 |
| 2002/0119472 A1 | 8/2002 | Lapidus et al. | 435/6 |
| 2002/0123052 A1 | 9/2002 | Laken | 435/6 |
| 2002/0132251 A1 | 9/2002 | Shuber | 435/6 |
| 2002/0164631 A1 | 11/2002 | Shuber et al. | 435/6 |
| 2003/0044780 A1 | 3/2003 | Lapidus et al. | 435/6 |
| 2003/0049659 A1 | 3/2003 | Lapidus et al. | 435/6 |
| 2003/0087258 A1 | 5/2003 | Shuber | 435/6 |
| 2004/0043467 A1 | 3/2004 | Shuber et al. | |
| 2005/0247563 A1 | 11/2005 | Shuber et al. | |
| 2005/0260638 A1 | 11/2005 | Shuber | |
| 2006/0121495 A1 | 6/2006 | Shuber | |
| 2007/0202513 A1 | 8/2007 | Shuber | |
| 2008/0145852 A1 | 6/2008 | Shuber | |

FOREIGN PATENT DOCUMENTS

| | | |
|---|---|---|
| AU | 1132595 A | 4/1996 |
| AU | 711754 B2 | 7/1997 |
| AU | 704696 B2 | 8/1997 |
| AU | 745862 B2 | 9/1998 |
| AU | 744746 B2 | 1/1999 |
| AU | 199879732 B2 | 1/1999 |
| AU | 19942333 A1 | 9/1999 |
| AU | 720489 B2 | 6/2000 |
| CA | 2228769 A1 | 2/1997 |
| CA | 2211702 A1 | 7/1997 |
| DE | 19530132 A1 | 2/1997 |
| DE | 19712332 A1 | 10/1998 |
| DE | 19736691 A1 | 2/1999 |
| EP | 0 063 879 A2 | 11/1982 |
| EP | 0063879 B1 | 11/1982 |
| EP | 0 185 494 A2 | 6/1986 |
| EP | 0185494 A2 | 6/1986 |
| EP | 0259031 A2 | 3/1988 |
| EP | 0270017 A2 | 6/1988 |
| EP | 0 284 362 A2 | 9/1988 |
| EP | 0284362 A2 | 9/1988 |
| EP | 0 332 435 A2 | 9/1989 |
| EP | 0332435 A2 | 9/1989 |
| EP | 0 337 498 A2 | 10/1989 |
| EP | 0337498 A2 | 10/1989 |
| EP | 0 063 879 B1 | 11/1989 |
| EP | 0 390 323 A2 | 10/1990 |
| EP | 0 390 323 A3 | 10/1990 |
| EP | 0390323 A2 | 10/1990 |
| EP | 0391565 A2 | 10/1990 |
| EP | 0 407 789 A1 | 1/1991 |
| EP | 0 407 789 B1 | 1/1991 |
| EP | 0 408 918 A1 | 1/1991 |
| EP | 0407789 A1 | 1/1991 |
| EP | 0408918 A1 | 1/1991 |
| EP | 0 332 435 B1 | 4/1992 |
| EP | 0 497 527 A1 | 8/1992 |
| EP | 0497527 A1 | 8/1992 |
| EP | 0 408 918 B1 | 11/1993 |
| EP | 0 608 004 A2 | 7/1994 |
| EP | 0608004 A2 | 7/1994 |
| EP | 0 259 031 B1 | 11/1994 |
| EP | 0648845 A2 | 4/1995 |
| EP | 0 664 339 A1 | 7/1995 |
| EP | 0664339 A1 | 7/1995 |
| EP | 1 251 183 A2 | 10/2002 |
| EP | 1251183 A2 | 10/2002 |
| GB | 229323 A | 9/1925 |
| GB | 2 293 238 A | 3/1996 |
| GB | 2327497 A | 1/1999 |
| JP | 3325270 | 7/2002 |
| WO | WO 89/11211 | 11/1989 |
| WO | WO-8911211 A2 | 11/1989 |
| WO | WO 90/09455 | 8/1990 |
| WO | WO-9009455 A1 | 8/1990 |
| WO | WO 91/02087 | 2/1991 |
| WO | WO-9102087 A1 | 2/1991 |
| WO | WO 91/13075 | 9/1991 |
| WO | WO-9113075 A2 | 9/1991 |
| WO | WO 92/13103 | 8/1992 |
| WO | WO-9213103 A1 | 8/1992 |
| WO | WO 92/15712 | 9/1992 |
| WO | WO-9215712 A1 | 9/1992 |
| WO | WO 92/16657 | 10/1992 |
| WO | WO-9216657 A1 | 10/1992 |
| WO | WO 93/06240 | 4/1993 |
| WO | WO-9306240 A1 | 4/1993 |
| WO | WO 93/18186 | 9/1993 |
| WO | WO-9318186 A1 | 9/1993 |
| WO | WO 93/20233 | 10/1993 |
| WO | WO 93/20235 | 10/1993 |
| WO | WO-9320233 A1 | 10/1993 |
| WO | WO-9320235 A1 | 10/1993 |
| WO | WO 93/25563 | 12/1993 |
| WO | WO-9325563 A1 | 12/1993 |
| WO | WO 94/00603 | 1/1994 |
| WO | WO 94/01447 | 1/1994 |
| WO | WO-9400603 A1 | 1/1994 |
| WO | WO-9401447 A1 | 1/1994 |
| WO | WO 94/09161 | 4/1994 |
| WO | WO-9409161 A1 | 4/1994 |
| WO | WO 94/10575 | 5/1994 |
| WO | WO 94/11383 | 5/1994 |
| WO | WO-9410575 A1 | 5/1994 |
| WO | WO-9411383 A1 | 5/1994 |
| WO | WO 94/23055 | 10/1994 |
| WO | WO-9423055 A1 | 10/1994 |
| WO | WO 95/00669 | 1/1995 |
| WO | WO-9500669 A1 | 1/1995 |
| WO | WO 95/07361 | 3/1995 |
| WO | WO-9507361 A1 | 3/1995 |
| WO | WO 95/09928 | 4/1995 |
| WO | WO 95/09929 | 4/1995 |
| WO | WO 95/12606 | 4/1995 |
| WO | WO-9509928 A1 | 4/1995 |
| WO | WO-9509929 A1 | 4/1995 |
| WO | WO 95/12607 | 5/1995 |
| WO | WO 95/13397 | 5/1995 |
| WO | WO-9512606 A1 | 5/1995 |
| WO | WO-9512607 A1 | 5/1995 |
| WO | WO-9513397 A1 | 5/1995 |
| WO | WO-9514108 A1 | 5/1995 |
| WO | WO 95/15400 | 6/1995 |
| WO | WO 95/16792 | 6/1995 |
| WO | WO-9515400 A1 | 6/1995 |
| WO | WO-9516792 A1 | 6/1995 |
| WO | WO 95/18818 | 7/1995 |
| WO | WO 95/19448 | 7/1995 |
| WO | WO-9518818 A1 | 7/1995 |
| WO | WO-9519448 A1 | 7/1995 |
| WO | WO 95/20680 | 8/1995 |
| WO | WO-9520680 A1 | 8/1995 |
| WO | WO 95/25813 | 9/1995 |
| WO | WO-9525813 A1 | 9/1995 |
| WO | WO 95/31728 | 11/1995 |
| WO | WO-9531728 A1 | 11/1995 |
| WO | WO 96/01907 | 1/1996 |
| WO | WO-9601907 A1 | 1/1996 |
| WO | WO 96/02671 | 2/1996 |
| WO | WO-9602671 A1 | 2/1996 |
| WO | WO 96/06951 | 3/1996 |
| WO | WO 96/08514 | 3/1996 |
| WO | WO-9606951 A1 | 3/1996 |
| WO | WO-9608514 A1 | 3/1996 |
| WO | WO 96/12821 | 5/1996 |
| WO | WO 96/13611 | 5/1996 |
| WO | WO-9612821 A1 | 5/1996 |
| WO | WO-9613611 A1 | 5/1996 |

| | | | |
|---|---|---|---|
| WO | WO-9623895 A1 | 8/1996 |
| WO | WO-9629430 A1 | 9/1996 |
| WO | WO 96/30545 | 10/1996 |
| WO | WO-9630545 A1 | 10/1996 |
| WO | WO-9707239 A1 | 2/1997 |
| WO | WO 97/09449 | 3/1997 |
| WO | WO 97/09600 | 3/1997 |
| WO | WO-9709449 A1 | 3/1997 |
| WO | WO-9709600 A2 | 3/1997 |
| WO | WO-9719191 A1 | 5/1997 |
| WO | WO 97/22719 | 6/1997 |
| WO | WO-9722719 A1 | 6/1997 |
| WO | WO 97/23651 | 7/1997 |
| WO | WO 97/25442 | 7/1997 |
| WO | WO-9723651 A1 | 7/1997 |
| WO | WO-9725442 A1 | 7/1997 |
| WO | WO 97/28450 | 8/1997 |
| WO | WO-9728450 A1 | 8/1997 |
| WO | WO-9734015 A1 | 9/1997 |
| WO | WO-9808971 A1 | 3/1998 |
| WO | WO 98/13522 | 4/1998 |
| WO | WO-9813522 A1 | 4/1998 |
| WO | WO-9814616 A1 | 4/1998 |
| WO | WO 98/38338 | 9/1998 |
| WO | WO 98/39478 | 9/1998 |
| WO | WO-9838338 A1 | 9/1998 |
| WO | WO-9839474 A1 | 9/1998 |
| WO | WO-9839478 A1 | 9/1998 |
| WO | WO 98/58081 | 12/1998 |
| WO | WO 98/58084 | 12/1998 |
| WO | WO-9858081 A1 | 12/1998 |
| WO | WO-9858084 A1 | 12/1998 |
| WO | WO-9907894 A1 | 2/1999 |
| WO | WO-9907895 A1 | 2/1999 |
| WO | WO-9910528 A1 | 3/1999 |
| WO | WO 99/20798 | 4/1999 |
| WO | WO-9920798 A1 | 4/1999 |
| WO | WO 99/28507 | 6/1999 |
| WO | WO-9926724 A2 | 6/1999 |
| WO | WO-9928507 A1 | 6/1999 |
| WO | WO 99/45147 | 9/1999 |
| WO | WO-9943851 A1 | 9/1999 |
| WO | WO-9945147 A1 | 9/1999 |
| WO | WO-9945374 A2 | 9/1999 |
| WO | WO 99/53316 | 10/1999 |
| WO | WO-9953316 A1 | 10/1999 |
| WO | WO 99/55912 | * 11/1999 |
| WO | WO 99/60160 | 11/1999 |
| WO | WO 99/60161 | 11/1999 |
| WO | WO 99/60162 | 11/1999 |
| WO | WO-9955912 A1 | 11/1999 |
| WO | WO-9960160 A1 | 11/1999 |
| WO | WO-9960161 A1 | 11/1999 |
| WO | WO-9960162 A1 | 11/1999 |
| WO | WO 99/66077 | 12/1999 |
| WO | WO-9966077 A2 | 12/1999 |
| WO | WO-9966078 A1 | 12/1999 |
| WO | WO-9966079 A1 | 12/1999 |
| WO | WO 00/09751 | 2/2000 |
| WO | WO-0009751 A1 | 2/2000 |
| WO | WO 00/11215 | 3/2000 |
| WO | WO-0011215 A2 | 3/2000 |
| WO | WO 00/31298 | 6/2000 |
| WO | WO 00/31303 | 6/2000 |
| WO | WO 00/31305 | 6/2000 |
| WO | WO 00/32820 | 6/2000 |
| WO | WO-0031298 A1 | 6/2000 |
| WO | WO-0031303 A2 | 6/2000 |
| WO | WO-0031305 A2 | 6/2000 |
| WO | WO-0032820 A1 | 6/2000 |
| WO | WO-0042223 A1 | 7/2000 |
| WO | WO 00/50640 | 8/2000 |
| WO | WO-0050640 A1 | 8/2000 |
| WO | WO-0050870 A1 | 8/2000 |
| WO | WO 00/58514 | 10/2000 |
| WO | WO 00/61808 | 10/2000 |
| WO | WO-0058514 A2 | 10/2000 |
| WO | WO-0060118 A2 | 10/2000 |
| WO | WO-0061808 A2 | 10/2000 |
| WO | WO 00/66005 | 11/2000 |
| WO | WO 00/70096 | 11/2000 |
| WO | WO-0066005 A1 | 11/2000 |
| WO | WO-0070096 A2 | 11/2000 |
| WO | WO 01/11083 | 2/2001 |
| WO | WO-0111083 A2 | 2/2001 |
| WO | WO 01/18252 | 3/2001 |
| WO | WO-0118252 A2 | 3/2001 |
| WO | WO 01/42502 | 6/2001 |
| WO | WO 01/42503 | 6/2001 |
| WO | WO 01/42781 | 6/2001 |
| WO | WO-0142502 A2 | 6/2001 |
| WO | WO-0142503 A2 | 6/2001 |
| WO | WO-0142781 A2 | 6/2001 |
| WO | WO 01/64950 | 9/2001 |
| WO | WO-0164950 A2 | 9/2001 |
| WO | WO 02/055740 | 7/2002 |
| WO | WO-02055740 A2 | 7/2002 |
| WO | WO 02/059379 | 8/2002 |
| WO | WO-02059379 A2 | 8/2002 |
| WO | WO 02/074995 | 9/2002 |
| WO | WO-02074995 A1 | 9/2002 |
| WO | WO 02/092858 | 11/2002 |
| WO | WO-02092858 A2 | 11/2002 |
| WO | WO-02099126 A1 | 12/2002 |
| WO | WO-03010442 A1 | 2/2003 |
| WO | WO 03/044217 | 5/2003 |
| WO | WO-03044217 A2 | 5/2003 |
| WO | WO 03/071252 | 8/2003 |
| WO | WO-03071252 A2 | 8/2003 |
| WO | WO-2004007773 A1 | 1/2004 |
| WO | WO-2004011357 A2 | 2/2004 |
| WO | WO-2005/017207 A2 | 2/2005 |
| WO | WO-05111244 A2 | 11/2005 |
| WO | WO-07044071 A2 | 4/2007 |
| WO | WO-2007/044071 A3 | 1/2008 |

OTHER PUBLICATIONS

Aaltonen et al. (1994), "Replication Errors in Benign and Malignant Tumors from Hereditary Nonpolyposis Colorectal Cancer Patients" *Cancer Research* 54:1645-1648.

Aaltonen et al. (1998), "Incidence of Hereditary Nonpolyposis Colorectal Cancer and the Feasibility of Molecular Screening for the Disease" *The New England Journal of Medicine* 338:1481-1487.

Abarzua et al. (1984), "Enzymatic techniques for the isolation of random single-base substitutions in vitro at high frequency" *Proc. Natl. Acad. Sci.*, 81:2030-2034.

Ahlquist et al. (2000), "Colorectal Cancer Screening by Detection of Altered Human DNA in Stool: Feasibility of a Multitarget Assay Panel" *Gastroenterology*, 119:1219-1227.

Ausubel et al. (1995), *Short Protocols in Molecular Biology*, 3d ed., pp. 2-3 -2-12, 3-30 -3-33.

Azhikina et al (1996), "Factors affecting the priming efficiency of short contiguous oligonucleotide strings in the primer walking strategy of DNA sequencing" *DNA Sequence—The Journal of Sequencing and Mapping*, 6:211-216.

Beck (1987), "Colorimetric—detected DNA sequencing" *Anal. Biochem.*, 164(2):514-520. Abstract only.

Bertario et al. (1999) "Risk of Colorectal Cancer Following Colonoscopic Polypectomy" *Tumori*, 85:157-162.

Beskin et al., "On the Mechanism of the Modular Primer Effect," *Nucleic Acids Research*, vol. 23, No. 15, pp. 2881-2885 (1995).

Blum H.E., (1995) "Colorectal Cancer: Future Population Screening for Early Colorectal Cancer" *European Journal of Cancer*, vol. 31A, pp. 1369-1372.

Böhm et al., (1997) "Deletion Analysis at the DEL-27, APC and MTSI Loci in Bladder Cancer: LOH at the *DEL-27* Locus on 5p13-12 is a Prognostic Marker of Tumor Progression" *Int. J. Cancer (Pred. Oncol.)*, 74:291-295.

Boom et al., "Rapid and Simple Method for Purification of Nucleic Acids", *Journal of Clinical Microbiology*, vol. 28, No. 3, pp. 495-503 (1990).

Bos et al., (May 28, 1987) "Prevalence of *ras* Gene Mutations in Human Colorectal Cancers" *Nature*, vol. 327, pp. 293-297.

Botstein et al. (1985) "Strategies and Applications of in vitro Mutagenesis," *Science*, 229(4719):1193-1201.

Braun et al., (1997) "Improved Analysis of Microsatellites Using Mass spectrometry" *Genomics*, vol. 46, pp. 18-23.

Brochure (undated), "Genotyping on the Tm/Luminex Universal Array Platform Using Primer Extension Chemistry," *Tm Bioscience Corporation*, Technical Bulletin—403, six pages.

Caetano-Anollés "Amplifying DNA with Arbitrary Oligonucleotide Primers," *Cold Spring Harbor Laboratory Press*, ISSN 1054-9803, pp. 85-94 (1993).

Caldas et al., (Jul. 1, 1994) "Detection of K-ras Mutations in the Stool of Patients with Pancreatic Adenocarcinoma and Pancreatic Ductal Hyperplasia" *Cancer Research*, vol. 54, pp. 3568-3573.

Capozzi et al. (1999) "Evaluation of the Replication Error Phenotype in Relation to Molecular and Clinicopathological Features in Hereditary and Early Onset Colorectal Cancer" *European Journal of Cancer*, 35:289-295.

Carothers et al., "Point Mutation Analysis in a Mammalian Gene: Rapid Preparation of Total RNA, PCR Amplification of cDNA, and Taq Sequencing by a Novel Method," *494 BioTechniques*, vol. 7, pp. 494-499 (date unknown), Abstract only.

Cave et al., (1994) "Reliability of PCR Directly from Stool Samples: Usefulness of an Internal Standard," *BioTechniques*, vol. 16, No. 5, pp. 809-810.

Chambers et al. (1986) "The structure of the mouse glutathione peroxidase gene: the selenocysteine in the active site is encoded by the 'termination' codon, TGA" *EMBO Journal*, 5(6):1221-1227. Abstract only.

Chapelle (1999) " Testing Tumors for Microsatellite Instability" *European Journal of Human Genetics*, 7:407-408.

Charlesworth et al., (Sep. 15, 1994) "The Evolutionary Dynamics of Repetitive DNA in Eukaryotes," *Nature*, vol. 371, pp. 215-220.

Chen et al. (1985) "Supercoil Sequencing: A Fast and Simple Method for Sequencing Plasmid DNA" *DNA*, 4(2):165-170.

Chen et al. (1997) "Microsatellite Instability in Sporadic-Colon-Cancer Patients With and Without Liver Metastases" *International Journal of Cancer*, 74:470-474.

Chen et al. "Template-Directed Dye-Terminator Incorporation (TDI) Assay: A Homogeneous DNA Diagnostic Method Based on Fluorescence Resonance Energy Transfer," *Nucleic Acids Research*, vol. 25, No. 2, pp. 347-353 (1997).

Chen et al., "Fluorescence Energy Transfer Detection as a Homogeneous DNA Diagnostic Method," *Proc. Natl. Acad. Sci.*, vol. 97, pp. 10756-10761 (Sep. 1997).

Coll et al., (Oct. 1989) "Evaluation of a Rapid Method of Extracting DNA from Stool Samples for Use in Hybridization Assays," *Journal of Clinical Microbiology*, vol. 27, No. 10, pp. 2245-2248.

Coughlin et al. (1999) "Public Health Perspectives on Testing for Colorectal Cancer Susceptibility Genes" *American Journal of Preventive Medicine*, 16:99-104.

Cunningham C. and M.G. Dunlop, (1996) "Molecular Genetic Basis of Colorectal Cancer Susceptibility," *British Journal of Surgery*, vol. 83, pp. 321-329.

Deng et al., (Dec. 20, 1996) "Loss of Heterozygosity in Normal Tissue Adjacent to Breast Carcinomas," *Science*, vol. 274, pp. 2057-2059.

Deuter et al., (1995) "A Method for Preparation of Fecal DNA Suitable for PCR," *Nucleic Acids Research*, vol. 23, No. 18, pp. 3800-3801.

Dib et al., (Mar. 14, 1996) "A Comprehensive Genetic Map of the Human Genome Based on 5,264 Microsatellites," *Nature* vol. 380, pp. 152-154.

Driscoll et al. (1989) "An In Vitro System for the Editing of Apolipoprotein B mRNA" *Cell*, 58:519-525.

Duffy.M.J., (1995) "Can Molecular Markers Now be Used for Early Diagnosis of Malignancy?" *Clin, Chem,.* vol. 41, No. 10, pp. 1410-1413.

Eguchi et al., (Apr. 15, 1996) "Mutations of the p53 Gene in the Stool of Patients with Resectable Colorectal Cancer," *Cancer Supplement*, vol. 77, No. 8, pp. 1707-1710.

Enari et al., (Jan. 1, 1998) "A Caspase-Activated DNase that Degrades DNA During Apoptosis, and its Inhibitor ICAD," *Nature*, vol. 391, pp. 43-50.

England et al., (1978) "3'-Terminal labeling of RNA with T4 RNA ligase," *Nature*, 275:560-561.

Erster et al., (1988) "Use of Rnase H and primer extension to analyze RNA splicing," *Nucleic Acids Res.*, 16(13):5999-6014.

Fabian et al,. (1989) "Allele-specific expression of the murine Ren-1 genes," *J. Biol. Chem.*, 264(29):17589-17594.

Fearon, E.R., (1995) "16 Molecular Abnormalities in Colon and Rectal Cancer," *The Molecular Basis of Cancer*, pp. 340-357.

Fournie et al., (1995) "Plasma DNA as a Marker of Cancerous Cell Death. Investigations in Patients Suffering from Lung Cancer and in Nude Mice Bearing Human Tumours," *Cancer Letters*, 91:221-227.

Frangi et al., "Nonsense Mutations Affect C1 Inhibitor Messenger RNA Levels in Patients with Type I Hereditary Angioneurotic Edema," *J. Clinical Invest*, 88:755-759.

Fu et al., "A DNA Sequencing Strategy That Requires Only Five Bases of Known Terminal Sequence for Priming," *Proc. Natl. Acad. Sci. USA*, 92: pp. 10162-10166 (1995).

Galinsky et al., (1988) "Molecular cloning and sequence analysis of the human parainfluenza 3 virus gene encoding the L protein," *Virology*, 165(2):499-510.

Gao et al., (1988) "Restriction primer extension method of labeling oligonucleotide probes and its application to the detection of Hb E genes," *Hemoglobin*, 12(5-6):691-697.

Gardner et al., (2002) "Acyclic and dideoxy terminator preferences denote divergent sugar recognition by archaeon and *Taq* DNA polymerase," *Nucleic Acids Research*, 30(2):605-613.

Giacona et al., "Cell-Free DNA in Human Blood Plasma: Length Measurements in Patients with Pancreatic Cancer and Healthy Controls," *Pancreas*, vol. 17, No. 1, pp. 89-97 (1998).

Gismondi et al., (1997) "Characterization of 19 Novel and Sic Recurring APC Mutations in Italian Adenomatous Polyposis Patients, Using Two Different Mutation Detection Techniques" *Human Mutation*, vol. 9, No. 4, pp. 370-373.

Godson, (1980) "Primed synthesis methods of sequencing DNA and RNA," *Fed. Proc.*, 39(10):2822-2829, Abstract only.

Green et al., (1980) "Targeted deletions of sequences from closed circular DNA," *Proc. Natl. Acad. Sci.*, 77(5):2455-2459.

Greene et al., (2001) "A Novel Method for SNP Analysis Using Fluorescence Polarization," *Perkin Elmer Life Sciences*.

Grossman et al. (1988), "Colonoscopic Screening of persons With Suspected Risk Factors for Colon Cancer" *Gastroenterology* 94:395-400.

Gyllensten U. B., Allen M., (1995) "Sequencing of In Vitro Amplified DNA," *Recombinant DNA Methodology II*, (Wu, ed.), pp. 565-578.

Hasegawa et al., (1995) "Detection of K-ras Mutations in DNAs Isolated From Feces of Patients with Colorectal Tumors by Mutant-Allele-Specific Amplification (MASA)," *Oncogene*, vol. 10, pp. 1441-1445.

Hickman et al. (1994), "Apoptosis and cancer chemotherapy," *Phil. Trans R. Soc. Lond.*, 345:319-325.

Hoang et al. (1997) "BAT-26, an Indicator of the Replication Error Phenotype in Colorectal Cancers and Cell Lines" *Cancer Research* 57:300-303.

Hollstein et al., "p53 Mutations in Human Cancers," *Science*, vol. 253, pp. 49-53 (Jul. 5, 1991).

Honchel et al., (1995) "Genomic Instability in Neoplasia," *Seminars in Cell Biology*, vol. 6, pp. 45-52.

Homes et al., (1990) "Emerging Techniques: Magnetic DNA Hybridization Properties of Oligonucleotide Probes Attached to Superparamagnetic Beads and Their Use in the Isolation of Poly(A) mRNA From Eukaryotic Cells," *GATA*, 7(6):145-150.

Hoss et al., (Sep. 17, 1992) "Excrement Analysis by PCR" *Scientific Correspondence* pp. 199.

Hunkapiller et al., (1984) "A microchemical facility for the analysis and synthesis of genes and proteins," *Nature*, 310:305-311.

Iacopetta et al. (1998) "Rapid and Nonisotopic SSCP-based Analysis of the BAT-26 Mononucleotide Repeat for Identification of the Replication Error Phenotype in Human Cancers," *Human Mutation* 12:355-360.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52:5-9.

Ikonen et al., "Quantitative Determination of Rare mRNA Species by PCR and Solid-phase Minisequencing," *Cold Spring Harbor Laboratory Press*, ISSN 1054-8903, pp. 234-240 (1992).

Iniesta et al. (1998) "Genetic Abnormalities and Microsatellite Instability in Colorectal Cancer" *Cancer Detection and Prevention* 22:383-395.

Ishimaru et al. (1995) "Microsatellite Instability in Primary and Metastatic Colorectal Cancers" *International Journal of Cancer* 64:153-157.

Iwaya et al. (1998) "Infrequent Frameshift Mutations of Polynucleotide Repeats in Multiple Primary Cancers Affecting the Esophagus and Other Organs" *Genes, Chrom & Cancer* 23:317-322.

Jack et al. (2002) "Kicking the Sugar Habit: AcyNTP Terminator Incorporation by Vent DNA Polymerase" *HGH2002 Poster Abstracts: 12, New Technologies*, Poster No. 621, Abstract only.

Jarvinen et al. (1995) "Screening Reduces Colorectal Cancer Rate in Families With Hereditary Nonpolyposis Colorectal Cancer" *Gastroenterology* 108:1405-1411.

Jernvall et al. (1999) "Microsatellite Instability: Impact on Cancer Progression in Proximal and Distal Colorectal Cancers" *European Journal of Cancer* 35:197-201.

Jessup J.M. and G.E. Gallick, (Sep./Oct. 1992) "The Biology of Colorectal Carcinoma," *Current Problems in Cancer* pp. 263-328.

Jonsson et al., (Jan. 1995) "From Mutation Mapping to Phenotype Cloning," *Proc. Natl. Acad. Sci.*, vol. 92 pp. 83-85.

Kainz et al., (1989) "A modified primer extension procedure for specific detection of DNA-RNA hybrids on nylon membranes," 179(2):366-370, Abstract only.

Kawakami et al. (2000), "Hypermethylated APC DNA in Plasma and Prognosis of Patients with Esophageal Adenocarcinoma," *Journal of the National Cancer Institute*, 92(22):1805-1811.

Kieleczawa et al., "DNA *Sequencing by Primer Walking with Strings of Contiguous Hexamers,*" *Science*, 258: pp. 1787-1791 (Dec. 11, 1992).

Kim et al. (1998) "Microsatellite Instability in Young Patients With Colorectal Cancer" *Pathology International* 48: 586-594.

Ko et al. (1999), "Genomic Instability and Alterations in *Apc, Mcc* and *Dcc* in Hong Kong Patients with Colorectal Carcinoma," *Int. J. Cancer (Pred. Oncol.)*, 84:404-409.

Konishi et al. (1996) "Molecular Nature of Colon Tumors in Hereditary Nonpolyposis Colon Cancer, Familial Polyposis, and Sporadic Colon Cancer" *Gastroenterology* 111: 307-317.

Kornher et al. (1989) "Mutation detection using nucleotide settings that alter electrophoretic mobility," *Nucleic Acids Research*, 17(19):7779-7784.

Kotler et al., (1993) "DNA Sequencing: Modular Primers Assembled from a Library of Hexamers or Pentamers," *Proc. Natl. Acad. Sci. USA*, 90: pp. 4241-4245 (May 1993).

Krook et al., "Rapid and simultaneous detection of multiple mutations by pooled and multiplex single nucleotide primer extension: application to the study of insulin-responsive glucose transporter and insulin receptor mutations in non-insulin-dependent diabetes," *Human Molecular Genetics*, vol. 1, No. 6, pp. 391-395 (1992).

Kuppuswamy et al. (1991) "Single Nucleotide primer extension to detect genetic diseases: Experiemental application to hemophilia B (factor IX) and Cystic fibrosis genes," *Proc. Natl. Acad. Sci.*, 88:1143-1147.

Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" *Gut* 44:839-843.

Lee et al., (1992) "DNA sequencing with dye-labeled terminators and T7 DNA polymerase: effect of dyes and dNTPs on incorporation of dye-terminators and probability analysis of termination fragments," *Nucleic Acids Research*, 20(10):2471-2483.

Lengauer et al., (Dec. 17, 1998) "Genetic Instabilities in Human Cancers," *Nature*, vol. 396, pp. 643-649.

Leong et al., (1993) "Detection of MYCN Gene Amplification and Deletions of Chromosome 1p in Neuroblastoma by In Situ Hybridization Using Routine Histologic Sections," *Laboratory Investigations*, vol. 69, No. 1, pp. 43-50.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41:428-433.

Lipkin et al., (1998) "Quantitative Trait Locus Mapping in Dairy Cattle by Means of Selective Milk DNA Pooling Using Dinucleotide Microsatellite Markers: Analysis of Milk Protein Percentage" *Genetics* 49:1557-1567.

Litia et al., (1992) "Simultaneous Detection of Two Cystic Fibrosis Alleles Using Dual-Label Time-Resolved Fluorometry," *Molecular and Cellular Probes*, vol. 6, pp. 505-512.

Liu et al., (1986) "Synthesis of a fixed-length single—stranded DNA probe by blocking primer extension in bacteriophage M13," *Gene*, 42:113-117.

Lleonart et al. (1998) "Microsatellite Instability and p53 Mutations in Sporadic Right and Left Colon Carcinoma" *American Cancer Society* 83:889-895.

Lo et al., (1984) "Specific amino acid substitutions in bacterioopsin: Replacement of a restriction fragments containing altered codons," *Proc. Natl. Acad. Sci.*, 81:2285-2289.

Loktionov A. and I. K. O'Neill, (1995) "Early Detection of Cancer—Associated Gene Alterations in DNA Isolated from Rat Feces During Intestinal Tumor Induction with 1,2-Dimethylhydrazine," *International Journal of Oncology*, vol. 6, pp. 437-445.

Loktionov et al., (Feb. 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337-341.

Lothe, et al., (1998) "The APC Gene I1307K Variant is Rare in Norwegian Patients with Familial and Sporadic Colorectal or Breast Cancer" *Cancer Research*, vol. 58, pp. 2923-2924.

Luo et al., (1988) "Point mutations in glycoprotein gene of vesicular stomatitis virus (New Jersey serotype) selected by resistance to neutralization by epitope-specific monoclonal antibodies," *Virology*, 163(2):341-348.

Mao L. et al., (Feb. 2, 1996) "Molecular Detection of Primary Bladder Cancer by Microsatellite Analysis," *Science*. vol. 271, pp. 659-662.

Matteucci et al. (1981)"Studies on Nucleotide Chemistry IV. Synthesis of Deoxyoligonucleotides on a Polymer Support," *J. Am. Chem. Soc.*, 103:3185-3191.

Maxam et al., (1977) "A new method for sequencing DNA," *Proc. Natl. Acad. Sci.*, 74(2):560-564, Abstract only.

Medeiros et al., (1989) "M13 Bioprints: non-isotopic detection of individual-specific human DNA fingerprints with biotinylated M13 bacteriophage," *Forensic Sci. Int.*, 43(3):275-280.

Middendorf et al. "8 Sequencing Technology," pp. 183-198.

Miller et al. (1997) "Semiautomated Resolution of Overlapping Stutter Patterns in Genomic Microsatellite Analysis" *Analytical Biochemistry* 251:50-56.

Mills, Stacey E., (2001) "Digital Diagnoses in an Analog World," *American Society for Clinical Pathology*, Editorial, two pages.

Morinaga et al., (Jul. 1984) "Improvement of Oligonucleotide-Directed Site-Specific Mutagenesis Using Double-Stranded Plasmid DNA," *Biotechnology*, pp. 636-639.

Myers, R.M., (Feb. 12, 1993) "The Pluses of Subtraction," *Science*, vol. 259, pp. 942-943.

Naber S. P., (Dec. 1, 1994) "Molecular Pathology—Detection of Neoplasia," *New England Journal of Medicine*, vol. 331, No. 22, pp. 1508-1510.

Netzer, P. et al., (1997) "Screening sigmoidoscopy or colosopy for detection of colorectal adenomas and cancers?" *Gastroenterology*, 112(4):A626, Abstract only.

Nikiforov et al., (1994) "Genetic Bit Analysis: a solid phase method for typing single nucleotide polymorphisms," *Nucleic Acids Research*, vol. 22, No. 20, pp. 4167-4175, Abstract only.

Nollau et al., (1996) "Detection of K-ras Mutations in Stools of Patients with Colorectal Cancer by Mutant-Enriched PCR," *Int. J. Cancer*, vol. 66 pp. 332-336.

Nollau et al., (May 1996) "Isolation of DNA from Stool and Bodily Fluids for PCR Amplication," *BioTechniques*, vol. 20, No. 5, pp. 784-788.

Olsen et al., (1989) "Incomplete primer extension during in vitro DNA amplification catalyzed by Taq polymerase; exploitation for DNA sequencing," *Nucleic Acids Res.*, 17(23):9613-9620, Abstract only.

Orlow I., et al., (Oct. 18, 1995) "Deletion of the p16 and p15 Genes in Human Bladder Tumors *Journal of the National Cancer Institute*.," vol. 87, No. 20, pp. 1524-1529.

Park et al. (1999) "Gene-Environment Interaction in Hereditary Nonpolyposis Colorectal Cancer with Implications for Diagnosis and Genetic Testing" *International Journal of Cancer* 82: 516-519.

Parker et al., (1988) "Interaction of 2-Halogenated dATP analogs (F, Cl and Br) with human DNA polymerases, DNA primase, and ribonucleotide reductase," *Mol. Pharmacol.*, 34(4):485-491, Abstract only.

Peattie, (1979) "Direct chemical method for sequencing RNA," *Proc. Natl. Acad. Sci.*, 76(4):1760-1764.

Peltomaki et al. (1997) "Mutations Predisposing to Hereditary Nonpolyposis Colorectal Cancer: Database and Results of a Collaborative Study" *Gastroenterology*113: 1146-1158.

Perlin et al., (1995) "Toward Fully Automated Tenotyping: Genotyping Microsatellite Markers by Deconvolution" *American Journal of Human Genetics* 57:1199-1210.

Ph Lebacq, "Polymerase chain reaction and other methods to detect hot-spot and multiple gene mutations," *Advances in Clinical Biology*, vol. 50, pp. 709-712 (1992).

Pharmacia, (1991/1992) *Molecular and Cell Biology Catalogue*, pp. 8.3-8.6.

Pharmacia, (1998) *BioDirectory*, pp. 104-109.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865-872.

Ponz de Leon et al. (1998) "Frequency and Type of Colorectal Tumors in Asymptomatic High -Risk Individuals in Families with Hereditary Nonpolyposis Colorectal Cancer" *Cancer Epidemiology. Biomarkers & Prevention* 7:639-641.

Ponz de Leon et al. (1999) "Hereditary Colorectal Cancer in the General Population: From Cancer Registration to Molecular Diagnosis" *Gut* 45:32-38.

Prober et al., (1987) "A System for Rapid DNA Sequencing with Fluorescent Chain-Terminating Dideoxynucleotides," *Research Articles*, pp. 336-341.

Pyatt et al. (1999) "Polymorphic Variation at the BAT-25 and BAT-26 Loci in Individuals of African Origin" *American Journal of Pathology* 155:349-353.

Raff M., (Nov. 12, 1998) "Cell Suicide for Beginners," *Nature*, vol. 396, pp. 119-122.

Rashid et al. (1999) "Genetic Epidemiology of Mutated K-*ras* Proto-Oncogene, Altered Suppressor Genes, and Microsatellite Instability in Colorectal Adenomas" *Gut* 44:826-833.

Ravelingien et al., (1995) "Contribution of Molecular Oncology in the Detection of Colorectal Carcinomas," *Acta Gastro-Enterologica Belgica*, vol. 58, pp. 270-273.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240-251.

Ridanpaa et al., (1995) "Detection of Loss of Heterozygosity in the p53 Tumor Suppressor Gene Using a PCR-based Assay," *Path. Res. Pract.*, vol. 191, pp. 399-402.

Riegler et al. (1999) "Prevalence of HNPCC in a Series of Consecutive Patients on the First Endoscopic Diagnosis of Colorectal Cancer: A Multicenter Study" *Endoscopy* 31:337-341.

Rinaldy et al. (1988) "Gene Cloning Using cDNA Libraries in a Differential Competition Hybridization Strategy: Application to Cloning XP-A Related Genes" *DNA*, 7(8):563-570.

Rodriguez-Bigas et al. (1997) "A National Cancer Institute Workshop on Hereditary Nonpolyposis Colorectal Cancer Syndrome: Meeting Highlights and Bethesda Guidelines" *Journal of the National Cancer Institute* 89:1758-1762.

Roemer et al., "Sequencing BAC DNA With Near-Infrared Flourescent Non-Nucleotide Terminators," *LI-COR On-line Poster 530*, LI-COR, Inc., Biotechnology, Lincoln, Nebraska, nine pages.

Rosenthal et al. (1985) " Solid-phase methods for sequencing of nucleic acids, I. Simultaneous sequencing of different oligodeoxyribonucleotides using a new, mechanically stable anion-exchange paper," *Nucleic Acids Research*, 13(4):1173-1184.

Runnebaum et al., "Multiplex PCR Screening detects small p53 deletions and insertions in human ovarian cancer cell lines," *Human Genetics*, vol. 93, pp. 620-624 (1994).

Salahshor et al. (1999) "Microsatellite Instability in Sporadic Colorectal Cancer is Not an Independent Prognostic Factor" *British Journal of Cancer* 81:190-193.

Sambrook, J. et al. (1989) "Molecular Cloning," Second Edition, p. 13.67-13.69.

Samiotaki et al., (1994) "Dual-Color Detection of DNA Sequence Variants by Ligase-Mediated Analysis," *Genomics*, 20:238-242.

Samowitz et al. (1995) "Microsatellite Instability in Human Colonic Cancer Is Not a Useful Clinical Indicator of Familial Colorectal Cancer" Gastroenterology 109:1765-1771.

Samowitz et al. (1997) "Microsatellite Instability in Colorectal Adenomas" *Gastroenterology* 112:1515-1519.

Samowitz et al. (1999) "BAT-26 and BAT-40 Instability in Colorectal Adenomas and Carcinomas and Germline Polymorphisms" *American Journal of Pathology* 154:1637-1641.

Sanger et al., (1975) "A Rapid Method for Determing Sequences in DNA by Primed Synthesis with DNA Polymerase," *J. Mol. Biol.*, 94:441-448.

Sanger et al., (Dec. 1977) "DNA Sequencing with Chain-Terminating Inhibitors" *Proc. Natl. Acad. Sci. USA*, vol. 74, No. 12, pp. 5463-5467.

Segel I., (1976), "Double Label Analysis," *Biochemical Calculations*, 2d ed., pp. 373-376.

Sheehan et al., (1987) "Reducing agent-sensitive dimerization of the hemagglutinin-neuraminidase glycoprotein of Newcastle disease virus correlates with the presence of cycteine at residue 123," *Virology*, 161(2):603-606.

Shitoh et al., (1998), "Important Microsatellite Markers in the Investigation of RER in Colorectal Cancers," *Jpn. J. Cli. Oncol*, vol. 28, No. 8, pp. 538-541.

Shortle et al., (1980) "Segment-directed mutagenesis: Construction in vitro of point mutations limited to a small predetermined region of a circular DNA molecule," *Proc. Natl. Acad. Sci.*, 77(9):5375-5379.

Shortle et al., (1981) "Directed Mutagenesis," *Ann. Rev. Genet.*, 15:265-294.

Shortle et al., (1982) "Gap misrepair mutagenesis: Efficient site-directed induction of transition, transversion, and frameshift mutations in vitro," *Proc. Natl. Acad. Sci.*, 79:1588-1592.

Shumaker et al., (1996) "Mutation Detection by Solid Phase Primer Extension," *Human Mutation*, vol. 7, pp. 346-354.

Sidransky et al., (1991) "Identification of p53 Gene Mutations in Bladder Cancers and Urine Samples," *Science*, vol. 252, pp. 706-709. Abstract only.

Sidransky, et al., (Apr. 3, 1992) "Identification of ras Oncogene Mutations in the Stool of Patients with Curable Colorectal Tumors," *Science*, vol. 256, pp. 102-105.

Singer et al., (1989) "Effect of 3' flanking neighbors on kinetics of pairing of dCTP or dTTP opposite $O^6$—methylguanine in a defined primed oligonucleotide when *Escherichia coli* DNA polymerase I is used," *Proc. Natl. Acad. Sci.*, 86:8271-8274.

Singer-sam et al., (1992) "A Sensitive, Quantitative Assay for Measurement of Allele-specific Transcripts Differing by a Single Nucleotide," *PCR Methods and Applications*, 1:160-163.

Smith-Ravin et al., (1995) "Detection of c-Ki-ras Mutations in Faecal Samples from Sporadic Colorectal Cancer Patients," *Gut*, vol. 36, pp. 81-86.

Sokolov, (1989) "Primer extension technique for the detection of single nucleotide in genomic DNA," *Nucleic Acids Research*, 18(12):3671.

Stahl et al., (1988) "Solid phase DNA sequencing using the biotin-avidin system," *Nucleic Acids Research*, 16(7):3025-3038.

Syngal et al. (1998) "Benefits of Colonoscopic Surveillance and Prophylactic Colectomy in Patients With Hereditary Nonpolyposis Colorectal Cancer Mutations" *Annals of Internal Medicine* 129:787-796.

Syngal et al. (1999) "Interpretation of Genetic Test Results for Hereditary Nonpolyposis Colorectal Cancer" *JAMA* 282:247.

Syvänen et al., (1990) "A primer-Guided Nucleotide Incorporation Assay in the Genotyping of Apolipoprotein E," *Genomics*, 8:684-692.

Syvänen, (1994) "Detection of Point Mutations in Human Genes by the Solid-phase Minisequencing Method," *Clinica Chimica Acta*, vol. 226, pp. 225-236.

Syvänen, (1997) "Solid-Phase Minisequencing," *Detection of Mutations and Polymorphisms in DNA*, Chapter 6, pp. 53-64.

Takeda et al., (1993) "Detection of K-ras Mutation in Sputum by Mutant-Allele-Specific Amplification (MASA)," *Human Mutation*, vol. 2, pp. 112-117.

Thibodeau et al., (May 7, 1993) "Microsatellite Instability in Cancer of the Proximal Colon," *Science*, vol. 260, pp. 816-819.

Traverso et al., (2002) "Detection of APC Mutations in Fecal DNA from Patients with Colorectal Cancer," *N Engl. J. Med.*, 346(5):311-320.

Ugozzoli, et al., "Detection of Specific Alleles by Using Allele-Specific Primer Extension Followed by Capture on Solid Support," *GATA* 9(4): pp. 107-112 (1992).

Vasen et al. (1993) "Surveillance in Hereditary Nonpolyposis Colorectal Cancer: An International Cooperative Study of 165 Families" *Diseases of the Colon & Rectum*) 36:1-4.

Vasen et al. (1998) "A Cost-Effectiveness Analysis of Colorectal Screening of Hereditary Nonpolyposis Colorectal Carcinoma Gene Carriers" *American Cancer Society* 82:1632-1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroenterology* 116:1453-1456.

Villa et al., (May 1996) "Identification of Subjects at Risk for Colorectal Carcinoma Through a Test Based on K-ras Determination in the Stool," *Gastroenterology*, vol. 110, No. 5, pp. 1346-1353.

Vogelstein, B. and Kinzler, K.W., (Aug. 1999) "Digital PCR," *Proc. Natl. Acad. Sci. USA*, vol. 96, pp. 9236-9241.

Vreeland et al. (2002) "Multiplexed, High-Throughput Genotyping by Single-Base Extension and End-Labeled Free-Solution Electrophoresis," *Anal. Chem.*, 74:4328-4333.

Wada et al., (1983) "Automatic DNA sequencer: Computer-programmed microchemical manipulator for the Maxam-Gilbert sequencing method," *Rev. Sci. Instrum.*, 54(11):1569-1572.

Wallace et al., (1979) "Hybridization of Synthetic Oligodeoxyribonucleotides to $\Phi_x$ 174 DNA: the Effect of Single Base Pair Mismatch," *Nucleic Acids Research*, vol. 6, No. 11, pp. 3543-3557.

Walsh et al., (1996) "Sequence Analysis and Characterization of Stutter Products at the Tetranucleotide Repeat Locus vWA," *Nucleic Acids Research* vol. 24, No. 14, 2807-2812.

Walsh et al., (Feb. 6, 1992) "Preferential PCR Amplification of Alleles: Mechanisms and Solutions," *PCR Methods and Applications*, pp. 241-250.

Wang et al., (May 15, 1998) "Large-Scale Identification, Mapping, and Genotyping of Single-Nucleotide Olymorphisms in the Human Genome," *Science*, vol. 280, pp. 1077-1082.

Watson et al., "Isolation of Differentiality Expressed Sequence Tags from Human Breast Cancer," *Advances in BriefXP 000576043*, pp. 4598-4602.

Wijnen et al. (1999) "Familial Endometrial Nature Cancer in Female Carriers of MSH6 Germline Mutations" *Nature Genectis* 23: 142-144.

Young G.P., and B.H. Demediu, (1992) "The Genetics, Epidemiology, and Early Detection of Gastrointestinal Cancers" *Current Opinion in Oncology*, vol. 4, pp. 728-735.

Zakour et al., (1984) "Site specific mutagenesis: insertion of single noncomplementary nucleotides at specified sites by error-directed DNA polymerization," *Nucleic Acids Research*, 12(16):6615-6628.

Zhou et al. (1997) "Allelic Profiles of Mononucleotide Repeat Microsatellites in Control Individuals and in Colorectal Tumors With and Without Replication Errors" *Oncogene* 15: 1713-1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21: 101-107.

Zimmern et al., (1978) "3'-Terminal nucleotide sequence of encephalomyocarditis virus RNA determined by reverse transcriptase and chain-terminating inhibitors," *Proc. Natl. Acad. Sci.*, 75:4257-4260.

Zoller et al. (1982) "Oligonucleotide-directed mutagenesis using M13-derived vectors: an efficient and general procedure for the production of point mutations in any fragment of DNA," *Nucleic Acids Research*, 10(20):6487-6500.

International Search Report for PCT/US03/04827 from the International Searching Authority, Date of Mailing: Sep. 4, 2003, 5 pages.

International Preliminary Examination Report for PCT/US99/08849 (Aug. 8, 2000).

Aaltonen et al. (1994) "Replication Errors in Benign and Malignant Tumors from Hereditary Nonpolyposis Colorectal Cancer Patients". Cancer Research 54:1645-1648.

Aaltonen et al. (1998) "Incidence of Hereditary Nonpolyposis Colorectal Cancer and the Feasibility of Molecular Screening for the Disease" The New England Journal of Medicine 338:1481-1487.

Abarzua et al. (1984) "Enzymatic techniques for the isolation of random single-base substitutions in vitro at high frequency" Proc. Natl. Acad. Sci., 81:2030-2034.

Agathanggelou et al. (2001) "Methylation associated inactivation of RASSF1A from region 3p21.3 in lung, breast and ovarian tumours" Oncogene 20(12):1509-18.

Agathanggelou et al. (2003) "Epigenetic inactivation of the candidate 3p21.3 suppressor gene BLU in human cancers" Oncogene 22(10):1580-8.

Agathanggelou et al. (2003) "Identification of novel gene expression targets for the Ras association domain family 1 (RASSF1A) tumor suppressor gene in non-small celllung cancer and neuroblastoma" Cancer Res. 63(17):5344-51.

Agathanggelou et al. (2005) "Role of the Ras-association domain family 1 tumor suppressor gene in human cancers" Cancer Res. 65(9):3497-508. Erratum in: Cancer Res. 65(12):5480.

Ahlquist et al. (2000) "Colorectal Cancer Screening by Detection of Altered Human DNA in Stool: Feasibility of a Multitarget Assay Panel" Gastroenterology, 119:1219-1227.

Akino et al. (2005) "The Ras Effector RASSF2 is a Novel Tumor-Suppressor Gene in Human Colorectal Cancer" Gastroenterology, 129:156-169.

Alonzo et al. (2007) "Statistical methods for evaluating DNA methylation as a marker for early detection or prognosis" Disease Markers, 23:113-120.

Ausubel et al. (1995) Short Protocols in Molecular Biology, 3d ed., pp. 2-3-2-12, 3-30-3-33.

Azhikina et al. (1996) "Factors affecting the priming efficiency of short contiguous oligonucleotide strings in the primer walking strategy of DNA sequencing" DNA Sequence—The Journal of Sequencing and Mapping, 6:211-216.

Behn et al. (1998) "Frequent detection of ras and p53 mutations in brush cytology samples from lung cancer patients by a restriction fragment length polymorphism-based "enriched PCR" technique," Clin Cancer Res. 4(2):361-71.

Behn et al. (1998) "Simple and reliable factor V genotyping by PNA-mediated PCR clamping" Thromb Haemost. 79(4):773-7.

Bertario et al. (1999) "Risk of Colorectal Cander Following Colonoscopic Polypectomy" Tumori, 85:157-162.

Beskin et al. (1995) "On the Mechanism of the Modular Primer Effect" Nucleic Acids Research, 23(15):2881-2885.

Blum H.E. (1995) "Colorectal Cancer: Future Population Screening for Early Colorectal Cancer" European Journal of Cancer, 31A:1369-1372.

Bohm et al. (1997) Deletion Analysis at the DEL-27, APC and WS] Loci in Bladder Cancer: LOH at the DEL-27 Locus on 5p13-12 is a Prognostic.

Boom et al. (1990) "Rapid and Simple Method for Purification of Nucleic Acids" Journal of Clinical Microbiology 28(3):495-503.
Bos et al. (1987) "Prevalence of ras Gene Mutations in Human Colorectal Cancers" Nature 327:293-297.
Botstein et al. (1985) "Strategies and Applications of in vitro Mutagenesis," Science, 229(4719):1193-1201.
Boynton et al. (2003) "DNA integrity as a potential marker for stool-based detection of colorectal cancer " Clinical Chemistry, 49(7):1058-1065.
Braun et al. (1997) "Improved Analysis of Microsatellites Using Mass spectrometry " Genomics, 46:18-23.
Brenner et al. (2005) "Fecal DNA Biomarkers for the Detection of Colorectal Neoplasia: Attractive, but is it feasible?" Journal of the National Cancer Institute, 97(15):1107-1109.
Brochure (undated) "Genotyping on the Tm/Luminex Universal Array Platform Using Primer Extension Chemistry," Tm Bioscience Corporation Technical Bulletin—403, six pages.
Burbee et al. (2001) "Epigenetic inactivation of RASSF1A in lung and breast cancers and malignant phenotype suppression" J Natl Cancer Inst. 93(9):691-9.
Caetano-Anolles (1993) "Amplifying DNA with Arbitrary Oligonucleotide Primers" Cold Spring Harbor Laboratory Press, ISSN 1054-9803, pp. 85-94.
Caldas et al. (1994) "Detection of K-ras Mutations in the Stool of Patients with Pancreatic Adenocarcinoma and Pancreatic Ductal Hyperplasia" Cancer Research, 54:3568-3573.
Capozzi et al. (1999) "Evaluation of the Replication Error Phenotype in Relation to Molecular and Clinicopaihological Features in Hereditary and Early Onset Colorectal Cancer" European Journal of Cancer 35:289-295.
Carothers et al. "Point Mutation Analysis in a Mammalian Gene: Rapid Preparation of Total RNA, PCR Amplification of cDNA, and Taq Sequencing by a Novel Method" 494 BioTechniques, 7:494-499 (date unknown) Abstract only.
Cave et al. (1994) "Reliability of PCR Directly from Stool Samples: Usefulness of an Internal Standard" BioTechniques, 16(5):809-810.
Chambers et al. (1986) "The structure of the mouse glutathione peroxidase gene: the selenocysteine in the active site is encoded by the 'termination' codon, TGA" EMBO Journal 5(6):1221-1227. Abstract only.
Chapelle (1999) " Testing Tumors for Microsatellite Instability" European Journal of Human Genetics 7:407-408.
Charlesworth et al. (1994) The Evolutionary Dynamics of Repetitive DNA in Eukaryotes, Nature, vol. 371, pp. 215-220.
Chen et al. (1985) "Supercoil Sequencing: A Fast and Simple Method for Sequencing Plasmid DNA" DNA, 4(2):165-170.
Chen et al. (1997) "Fluorescence Energy Transfer Detection as a Homogeneous DNA Diagnostic Method" Proc. Natl Acad. Sci., 97:10756-10761.
Chen et al. (1997) "Microsatellite Instability in Sporadic-Colon-Cancer Patients With and Without Liver Metastases" International Journal of Cancer, 74:470-474.
Chen et al. (1997) "Template-Directed Dye-Terminator Incorporation (TDI) Assay: A Homogeneous DNA Diagnostic Method Based on Fluorescence Resonance Energy Transfer" Nucleic Acids. Research, vol. 25, No. 2, pp. 347-353.
Chen et al. (2005) "Detection in fecal DNA of colon cancer-specific methylation of the nonexpressed vimentin gene" J Natl Cancer Inst. 97:1124-1132.
Coll et al. (1989) "Evaluation of a Rapid Method of Extracting DNA from Stool Samples for Use in Hybridization Assays" Journal of Clinical Microbiology, 27(10):2245-2248.
Coughlin et al. (1999) "Public Health Perspectives on Testing for Colorectal Cancer Susceptibility Genes" American Journal of Preventive Medicine, 16:99-104.
Cunningham C. and M.G. Dunlop (1996) "Molecular Genetic Basis of Colorectal Cancer Susceptibility" British Journal of Surgery, 83:321-329.
Dallol et al. (2004) "RASSF1A interacts with microtubule-associated proteins and modulates microtubule dynamics" Cancer Res. 64(12):4112-6.

Dammann et al. (2000) "Epigenetic inactivation of a RAS association domain family protein from the lung tumour suppressor locus 3p21.3." Nat Genet. 25(3):315-9.
Deng et al., (1996) "Loss of Heterozygosity in Normal Tissue Adjacent to Breast Carcinomas" Science. 274:2057-2059.
Deuter et al. (1995) "A Method for Preparation of Fecal DNA Suitable for PCR" Nucleic Acids Research, 23(18):3800-3801.
Dib et al. (1996) "A Comprehensive Genetic Map of the Human Genome Based on 5,264 Microsatellites" Nature 380:152-154.
Downward (2002) "Targeting RAS signalling pathways in cancer therapy" Nat Rev Cancer. 3(1):11-22.
Downward (2003) "Cell biology: metabolism meets death" Nature. 424(6951):896-7.
Downward (2003) "Role of receptor tyrosine kinases in G-protein-coupled receptor regulation of Ras: transactivation or parallel pathways?" Biochem J. 376(Pt 3):e9-10.
Dreijerink et al. (2001) "The candidate tumor suppressor gene, RASSF1A, from human chromosome 3p21.3 is involved in kidney tumorigenesis" Proc Natl Acad Sci USA, 98(13):7504-9.
Driscoll el al. (1989) "An In Vitro System for the Editing of Apolipoprotein B mRNA" Cell, 58:519-525.
Duffy (1995) "Can Molecular Markers Now be Used for Early Diagnosis of Malignancy?" Clin. Chem. 41(10):1410-1413.
Eckfeld et al. (2004) "RASSF4/AD037 is a potential ras effector/tumor suppressor of the RASSF family" Cancer Res. 64(23):8688-93.
Eguchi et al. (1996) "Mutations of the p53 Gene in the Stool of Patients with Resectable Colorectal Cancer" Cancer Supplement, 77(8):1707-1710.
Enari et al. (1998) "A Caspase-Activated DNase that Degrades DNA During Apoptosis, and its Inhibitor ICAD," Nature, 391:43-50.
Endoh et al. (2005) "RASSF2, a potential tumor suppressor, is silenced by CpG island hypermethylation in gastric cancer" British Journal of Cancer, 93:1395-1399.
England et al. (1978) "3'-Terminal labeling of RNA with T4 RNA ligase" Nature 275:560-561.
Erster et al. (1988) "Use of Rnase H and primer extension to analyze RNA splicing" Nucleic Acids Res., 16(13):5999-6014.
Fabian et al. (1989) "Allele-specific expression of the murine Ren-1 genes" J. Biol. Chem. 264(29):17589-17594.
Fearon (1995) "16 Molecular Abnormalities in Colon and Rectal Cancer" The Molecular Basis of Cancer, pp. 340-357.
Fearon et al. (1990) "A genetic model for colorectal tumorigenesis" Cell. 61(5):759-67.
Feng et al. (2006) "Molecular Biomarkers for Cancer Detection in Blood and Bodily Fluids" Critical Reviews in Clinical Laboratory Sciences, 43(5-6):497-560.
Floss et al. (Sep. 17, 1992) "Excrement Analysis by PCR" Scientific Correspondence pp. 199.
Fournie et al. (1995) "Plasma DNA as a Marker of Cancerous Cell Death. Investigations in Patients Suffering from Lung Cancer and in Nude Mice Bearing Human Tumours". Cancer Letters, 91:221-227.
Frangi et al. Nonsense Mutations Affect CI Inhibitor Messenger RNA Levels in Patients with Type I Hereditary Angioneurotic Edema, J. Clinical Invest. 88:755-759.
Galinsky et al. (1988) "Molecular cloning and sequence analysis of the human parainfluenza 3 virus gene encoding the L protein" Virology, 165(2):499-510.
Gao et al. (1988) "Restriction primer extension method of labeling oligonucleotide probes and its application to the detection of Hb E genes" Hemoglobin, 12(5-6):691-697.
Gardner et al. (2002) "Acyclic and dideoxy terminator preferences denote divergent sugar recognition by archaeon and Taq DNA polymerases" Nucleic Acids Research, 30(2):605-613.
Giacona et al. (1998) "Cell-Free DNA in Human Blood Plasma: Length Measurements in Patients with Pancreatic Cancer and Healthy Controls" Pancreas, 17(1):89-97.
Gismondi et al. (1997) "Characterization of 19 Novel and Sic Recuroing APC Mutations in Italian Adenomatous Polyposis Patients, Using TWO-Different Mutation Detection Techniques" Human Mutation, 9(4):370-373.
Godson, (1980) "Primed synthesis methods of sequencing DNA and RNA" Fed. Proc.. 39(10):2822-2829, Abstract only.

Green et al. (1980) "Targeted deletions of sequences from closed circular DNA" Proc. Natl. Acad. Sci. 77(5):2455-2459.
Greene et al. (2001) "A Novel Method for SNP Analysis Using Fluorescence Polarization" Perkin Elmer Life Sciences.
Grossman et al. (1988) "Colonoscopic Screening of persons With Suspected Risk Factors for Colon Cancer" Gastmenterology 94:395-400.
Gyllensten et al. (1995) "Sequencing of In Vitro Amplified DNA" Recombinant DNA Methodology II, (Wu, ed.) pp. 565-578.
Hasegawa et al. (1995) "Detection of K-ras Mutations in DNAs Isolated From Feces of Patients with Colorectal Tumors by Mutant-Allele-Specific Amplification (MASA)" Oncogene, 10:1441-1445.
Herman (2002) "Hypermethylation pathways to colorectal cancer. Implications for prevention and detection" Gastroenterol Clin North Am. 31(4):945-58.
Herman JG, et al. "Methylation-specific PCR: A novel PCR assay for methylation status of CpG islands" Proc Natl Acad Sci USA 93:9821-9826.
Hesson et al. (2003) "NORE1A, a homologue of RASSF1A tumour suppressor gene is inactivated in human cancers" Oncoqene. 22(6):947-54.
Hesson et al. (2004) "Frequent epigenetic inactivation of RASSF1A and BLU genes located within the critical 3p21.3 region in gliomas" Oncogene 23( 3):2408-19.
Hesson et al. (2005) "CpG island promoter hypermethylation of a novel Ras-effector gene RASSF2A is an early event in colon carcinogenesis and correlates inversely with K-ras mutations" Oncogene 24:3987-3994.
Hickman et al. (1994) "Apoptosis and cancer chemotherapy" Phil. Trans R. Soc. Lond., 345:319-325.
Hoang et al. (1997) "BAT-26, an Indicator of the Replication Error Phenotype in Colorectal Cancers and Cell Lines" Cancer Research 57: 300-303.
Hollstein et al. (1991) "p53 Mutations in Human Cancers" Science, 253:49-53.
Honchel et al. (1995) "Genomic Instability in Neoplasia," Seminars in Cell Biology, 6:45-52.
Hunkapiller et al. (1984) "A microchemical facility for the analysis and synthesis of genes and proteins" Nature 310:305-311.
Iacopetta et al. (1998) "Rapid and Nonisotopic SSCP-based Analysis of the BAT-26 Mononucleotide Repeat for Identification of the Replication Error Phenotype in Human Cancers" Human Mutation 12:355-360.
Iino et al. (1999) "DNA Microsatellite Instability in Hyperplastic Polyps, Serrated Adenomas, and Mixed Polyps: a Mild Mutator Pathway for Colorectal Cancer?" Journal of Clinical Pathology 52: 5-9.
Ikonen et al. (1992) "Quantitative Determination of Rare mRNA Species by PCR and Solid-phase Minisequencing" Cold Spring Harbor Laboratory Press, ISSN 1054-8903, pp. 234-240.
Iniesta et al. (1998) "Genetic Abnormalities and Microsatellite Instability in Colorectal Cancer" Cancer Detection and Prevention 22:383-395.
International Search Report for PCT/US03/04827 from the International Searching Authority, Date of Mailing: Sep. 4, 2003, 5 pages.
International Search Report for PCT/US05/016518 dated Apr. 7, 2006.
International Search Report for PCT/US05/30942 dated Jul. 26, 2006.
International Search Report for PCT/US05/39670 dated Apr. 12, 2006.
Irimia et al. (2004) "CpG island promoter hypermethylation of the Ras-effector gene NORE1 A occurs in the context of a wild-type K-ras in lung cancer" Oncogene. 23(53):8695-9.
Ishimaru et al. (1995) "Microsatellite Instability in Primary and Metastatic Colorectal Cancers" International Journal of Cancer 64:153-157.
Iwaya et al. (1998) "Infrequent Fratneshift Mutations of Polynucleotide Repeats in Multiple Primary Cancers Affecting the Esophagus and Other Organs" Genes, Chrom & Cancer 23:317-322.
Jack et al. (2002) "Kicking the Sugar Habit: AcyNTP Terminator Incorporation by Vent DNA Polymerase" HGH2002 Poster Abstracts: 12. New Technologies, Poster No. 621, Abstract only.
Jarvinen et al. (1995) "Screening Reduces Colorectal Cancer Rate in Families With Hereditary Nonpolyposis Colorectal Cancer" Gastroenterology 108: 1405-1411.
Jeffreys et al. (2003) "DNA enrichment by allele-specific hybridization (DEASH): a novel method for haplotyping and for detecting low-frequency base substitutional variants and recombinant DNA molecules" Genome Research, 13:2316-2324.
Jernvall et al. (1999) "Microsatellite Instability: Impact on Cancer Progression in Proximal and Distal Colorectal Cancers" European Journal of Cancer 35:197-201.
Jessup et al. (1992) "The Biology of Colorectal Carcinoma," Current Problems in Cancer pp. 263-328.
Jonsson et al. (1995) "From Mutation Mapping to Phenotype Cloning" Proc. Natl. Acad. Sci., 92:83-85.
Kawakami et al. (2000) "Hypermethylated APC DNA in Plasma and Prognosis of Patients with Esophageal Adenocarcinoma" Journal of the National Cancer Institute, 92(22):1805-1811.
Khokhlatchev et al. (2002) "Identification of a novel Ras-regulated proapoptotic pathway" Curr Biol. 12(4):253-65.
Kieleczawa et al. (1992) "DNA Sequencing by Primer Walking with Strings of Contiguous Hexamers" Science,258:1787-1791.
Kim et al. "CpG island methylation of genes accumulates during the adenoma progression step of the multistep pathogenesis of colorectal cancer" Genes Chromosomes Cancer 45:781-789.
Kim et al. (1998) "Microsatellite Instability in Young Patients With Colorectal Cancer" Pathology International 48: 586-594.
Ko et al. (1999) "Genomic Instability and Alterations in Apc, Mcc and Dcc in Hong Kong Patients with Colorectal Carcinoma" Int. J. Cancer (Pred. Oncol.1, 84:404-409.
Komher at al. (1989) "Mutation detection using nucleotide settings that alter electrophoretic mobility" Nucleic Acids Research, 17(19):7779-7784.
Kondo et al. (2004) "Epigenetic changes in colorectal cancer" Cancer Metastasis Rev. 23(1-2):29-39.
Konishi et al. (1996) "Molecular Nature of Colon Tumors in Hereditary Nonpolyposis Colon Cancer, Familial Polyposis, and Sporadic Colon Cancer" Gastroenterology 1 1 1 : 307-317.
Kotler et al, (1993) "DNA Sequencing: Modular Primers Assembled from a Library of Hexamers or Pentamers" Proc. Natl. Acad Sci. USA, 90: 4241-4245 (May 1993).
Krook et al. (1992) "Rapid and simultaneous detection of multiple mutations by pooled and multiplex single nucleotide primer extension: application to the study of insulin-responsive glucose transporter and insulin receptor mutations in non-insulin-dependent diabetes" Human Molecular Genetics, 1(6):391-395.
Kuppuswamy et al. (1991) "Single Nusleotide primer extension to detect genetic diseases: Experiemental application to hemophilia B (factor IX) and Cystic fibrosis genes" Proc. Natl. Acad. Sci., 88:1143-1147.
Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" Gut 44:839-843.
Lebacq (1992) "Polymerase chain reaction and other methods to detect hot-spot and multiple gene mutations" Advances in Clinical Biology, 50:709-712.
Lee et al, (1992) "DNA sequencing with dye-labeled terminators and T7 DNA polymerase: effect of dyes and dNTPs on incorporation of dye-terminators and probability anaylsis of termination fragments" Nucleic Acid Research 20(10):2471-2483.
Lengauer et al. (1998) "Genetic Instabilities in Human Cancers" Nature, 396:643-649.
Leong et al. (1993) "Detection of MYCN Gene Amplification and Deletions of Chromosome Ip in Neuroblastoma by In Situ Hybridization Using Routine Histologic Sections" Laboratorv Investigations, 69(1):43-50.
Lerman et al. (2000) "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium," Cancer Res. 60(21):6116-33.

Lin et al. (1998) "Colorectal and Extracolonic Cancer Variations in MLHI/MSH2 Hereditary Nonpolyposis Colorectal Cancer Kindreds and the General Population" Diseases of the Colon & Rectum 41:428-433.

Lipkin et al. (1998) "Quantitative Trait Locus Mapping in Dairy Cattle by Means of Selective Milk DNA Pooling Using Dinucleotide Microsatellite Markers: Analysis of Milk Protein Percentage" Genetics 49:1557-1567.

Litia et al. (1992) "Simultaneous Detection of TWO-Cystic Fibrosis Alleles Using Dual-Label Time-Resolved Fluorometry" Molecular and Cellular Probes, 6:505-512.

Liu et al. (2003) "Control of microtubule stability by the RASSF1A tumor suppressor," Oncogene. 22(50):8125-36.

Liu et al. (1986) "Synthesis of a fixed-length single—stranded DNA probe by blocking primer extension in bacteriophage M13" Gene, 42:113-117.

Lleonart et al. (1998) "Microsatellite Instability and p53 Mutations in Sporadic Right and Left Colon Carcinoma" American Cancer Society 83:889-895.

Lo et al. (1984) "Specific amino acid substitutions in bacterioopsin: Replacement of a restriction fragments containing altered codons," Proc. Natl. Acad. Sci., 81:2285-2289.

Loktionov A. and I. K. O'Neill, (1995) "Early Detection of Cancer-Associated Gene Alterations in DNA Isolated from Rat Feces During Intestinal Tumor Induction with 1,2-Dimethylhydrazine" International Journal of Oncology, 6:437-445.

Loktionov et al. (1998) "Quantitation of DNA from Exfoliated Colonocytes Isolated from Human Stool Surface as a Novel Noninvasive Screening Test for Colorectal Cancer" Clinical Cancer Research, 4:337-341.

Lothe, et al. (1998) "The APC Gene 11307K Variant is Rare in Norwegian Patients with Familial and Sporadic Colorectal or Breast Cancer" Cancer Research, 58:2923-2924.

Luo et al. (1988) "Point mutations in glycoprotein gene of vesicular stomatitis virus (New Jersey serotype) selected by resistance to neutralization by epitope-specific monoclonal antibodies" Virology, 163(2):341-348.

Mao L. et al. (1996) "Molecular Detection of Primary Bladder Cancer by Microsatellite Analysis" Science. 271:659-662.

Matteucci et al. (1981)"Studies on Nucleotide Chemistry IV. Synthesis of Deoxyoligonucleotides on a Polymer Support" J. Am. Chem. Soc., 103:3185-3191.

Maxam et al. (1977) "A new method for sequencing DNA" Proc. Natl. Acad. Sci., 74(2):560-564, Abstract only.

Medeiros et al. (1989) "M13 Bioprints: non-isotopic detection of individual-specific human DNA fingerprints with biotinylated M13 bacteriophage" Forensic Sci. Int., 43(3):275-280.

Meijers-Heijboer et al. (1999) "Familial Endometrial Cancer in Female Carriers of MSH6 Germline Mutations" Nature Genetics 23: 142-144.

Middendorf et al. "8 Sequencing Technology," pp. 183-198.

Miller et al. (1997) "Semiautomated Resolution of Overlapping Stutter Patterns in Genomic Microsatellite Analysis" Analytical Biochemistry 251:50-56.

Mills, Stacey E. (2001) "Digital Diagnoses in an Analog World" American Society for Clinical Pathology Editorial, two-pages.

Morinaga et al. (1984) "Improvement of Oligonucleotide—Directed Site-Specific Mutagenesis Using Double-Stranded Plasmid DNA," Biotechnology pp. 636-639.

Muller et al. (2004) "Methylation changes in faecal DNA: a marker for colorectal cancer screening?" Lancet. 363(9417):1283-5.

Myers, R.M. (1993) "The Pluses of Subtraction" Science, 259:942-943.

Naber (1994) "Molecular Pathology—Detection of Neoplasia" New England Journal of Medicine, 331(22):1508-1510.

Netzer, P. et al. (1997) "Screening sigmoidoscopy or colosopy for detection of colorectal adenomas and cancers?" Gastroenterology, 112(4):A626, Abstract only.

Nikiforov et al. (1994) "Genetic Bit Analysis: a solid phase method for typing single nucleotide polymorphisms" Nucleic Acids Research, 22(20):4167-4175, Abstract only.

Nollau et al. (1996) "Detection of K-ras Mutations in Stools of Patients with Colorectal Cancer by Mutant— Enriched PCR" Int. J. Cancer, 66:332-336.

Nollau et al. (1996) "Isolation of DNA from Stool and Bodily Fluids for PCR Amplication" BioTechniques, 20(5):784-788.

Olsen et al. (1989) "Incomplete primer extension during in vitro DNA amplification catalyzed by Taq polymerase; exploitation for DNA sequencing" Nucleic Acids Res . . . 17(23):9613-9620, Abstract only.

Olson et al. "DNA stabilization is critical for maximizing performance of fecal DNA based colorectal cancer tests" Diaqn Mol Pathol 14:183-191.

Orlow et al. (1995) "Deletion of the p16 and p15 Genes in Human Bladder Tumors Journal of the National Cancer Institute" 87(20):1524-1529.

Ortiz-Vega et al. (2002) "The putative tumor suppressor RASSF1A homodimerizes and heterodimerizes with the Ras-GTP binding protein Nore1" Oncogene. 21(9):1381-90. Erratum in: Oncogene 21(12):1943.

Park et al.(1999) "Gene-Environment Interaction in Hereditary Nonpolyposis Colorectal Cancer with Implications for Diagnosis and Genetic Testing" International Journal of Cancer 82: 516-519.

Parker et al. (1988) "Interaction of 2-Halogenated dATP analogs (F, Cl and Br) with human DNA polymerases, DNA primase, and ribonucleotide reductase" Mol. Pharmacol., 34(4):485491, Abstract only.

Peattie, (1979) "Direct chemical method for sequencing RNA" Proc. Natl. Acad. Sci., 76(4):1760-1764.

Peltomaki et al (1997) "Mutations Predisposing to Hereditary Nonpolyposis Colorectal Cancer: Database and Results of a Collaborative Study" Gastroenterology 113: 1146-1158.

Perlin et al. (1995) "Toward Fully Automated Tenotyping: Genotyping Microsatellite Markers by Deconvolution" American Journal of Human Genetics 57:1199-1210.

Pharmacia (1991/1992) Molecular and Cell Biology Catalogue, pp. 8.3-8.6.

Pharmacia (1998) BioDirectorv, pp. 104-109.

Piao et al. (1997) "Relationship between Loss of Heterozygosity of Tumor Suppressor Genes and Histologic Differentiation in Hepatocellular Carcinoma" Cancer, 80(5):865-872.

Ponz de Leon et al. (1998) "Frequency and Type of Colorectal Tumors in Asymptomatic High Risk Individuals in Families with Hereditary Nonpolyposis Colorectal Cancer" Cancer Epidemiology, Biomarkers & Prevention 7: 639-641.

Ponz de Leon et al. (1999) "Hereditary Colorectal Cancer in the General Population: From Cancer Registration to Molecular Diagnosis" Gut 45: 32-38.

Praskova et al. (2004) "Regulation of the MST1 kinase by autophosphorylation, by the growth inhibitory proteins, RASSF1 and NORE1, and by Ras" Biochem J. 381(Pt 2):453-62.

Prober et al. (1987) "A System for Rapid DNA Sequencing with Fluorescent Chain—Terminating Dideoxynucleotides" Research Articles, pp. 336-341.

Pyatt et al. (1999) "Polymorphic Variation at the BAT-25 and BAT-26 Loci in Individuals of African Origin" American Journal of Pathology 155: 349-353.

Raff (1998) "Cell Suicide for Beginners," Nature, 396:119-122.

Rashid et al. (1999) "Genetic Epidemiology of Mutated K-ras Proto-Oncogene, Altered Suppressor Genes, and Microsatellite Instability in Colorectal Adenomas" Gut 44: 826-833.

Ravelingien et al. (1995) "Contribution of Molecular Oncology in the Detection of Colorectal Carcinomas" Acta Gastro-Enterologica Belgica, 58:270-273.

Rhyu (1996) Molecular Mechanisms Underlying Hereditary Nonpolyposis Colorectal Carcinoma, Journal of the National Cancer Institute, 88(5):240-251.

Rice et al. (2001) "Identification of single nucleotide polymorphisms (SNPs) and other sequence changes and estimation of nucleotide diversity in coding and flanking regions of the NMDAR1 receptor gene in schizophrenic patients" Molecular Psychiatry, 6(3):274-284.

Ridanpaa et al. (1995) "Detection of Loss of Heterozygosity in the p53 Tumor Suppressor Gene Using a PCR-based Assay" Path. Res. Pract., 191:399-402.

Riegler et al. (1999) "Prevalence of HNPCC in a Series of Consecutive Patients on the First Endoscopic Diagnosis of Colorectal Cancer: A Multicenter Study" Endoscopy 31: 337-341.

Rinaldy et al. (1988) "Gene Cloning Using cDNA Libraries in a Differential Competition Hybridization Strategy: Application to Cloning XP-A Related Genes" DNA 7(8):563-70.

Rodriguez-Bigas et al. (1997) "A National Cancer Institute Workshop on Hereditary NonpolyposisColorectal Cancer Syndrome: Meeting Highlights and Bethesda Guidelines" Journal of the National CancerInstitute 89:1758-1762.

Roemer et al (2000) "Sequencing BAC DNA With Near-Infrared Flourescent Non-Nucleotide Terminators" LI-COR On-line Poster 530, LI-COR, Inc., Biotechnology, Lincoln, Nebraska, nine pages.

Rosenthal et al. (1985) " Solid-phase methods for sequencing of nucleic acids, I. Simultaneous sequencing different oligodeoxyribonucleotides using a new, mechanically stable anion-exchange paper" Nucleic Acids Research, 13(4):1173-1184.

Runnebaum et al. (1994) "Multiplex PCR Screening detects small p53 deletions and insertions in human ovarian cancer cell lines" Human Genetics, 93:620-624 .

Salahshor et al. (1999) "Microsatellite Instability in Sporadic Colorectal Cancer is Not an Independent Prognostic Factor" British Journal of Cancer, 81:190-193.

Samiotaki et al. (1994) "Dual-Color Detection of DNA Sequence Variants by Ligase-Mediated Analysis" Genomics 20:238-42.

Samowitz et al. (1995) "Microsatellite Instability in Human Colonic Cancer Is Not a Useful Clinical Indicator of Familial Colorectal Cancer" Gastroenterology 109:1765-1771.

Samowitz et al. (1997) "Microsatellite Instability in Colorectal Adenomas" Gastroenterology 112:1515-1519.

Samowitz et al. (1999) "BAT-26 and BAT-40 Instability in Colorectal Adenomas and Carcinomas and Germline Polymorphisms" American Journal of Pathology 154:1637-1641.

Sanger et al. (1975) "A Rapid Method for Determining Sequences in DNA by Primed Synthesis with DNA Polymerase " J. Mol. Biol., 94:441-448.

Sanger et al. (Dec. 1977) "DNA Sequencing with Chain—Terminating Inhibitors" Proc. Natl. Acad. Sci. USA, 74(12):5463-5467.

Segel (1976) "Double Label Analysis" Biochemical Calculations, 2d ed., pp. 373-376.

Sheehan et al. (1987) "Reducing agent—sensitive dimerization of the hemagglutinin—neuraminidase glycoprotein of Newcastle disease virus correlates with the presence of cycteine at residue 123" Virology, 161(2):603-606.

Shitoh et al. (1998) "Important Microsatellite Markers in the Investigation of RER in Colorectal Cancers," Jim. J. Cli, Oncol., 28(8):538-541.

Shortle et al, (1980) "Segment-directed mutagenesis: Construction in vitro of point mutations limited to a small predetermined region of a circular DNA molecule" Proc. Natl. Acad. Sci., 77(9):5375-5379.

Shortle et al. (1981) "Directed Mutagenesis" Ann. Rev. Genet. 15:265-294.

Shortle et al. (1982) "Gap misrepair mutagenesis: Efficient site—directed induction of transition, transversion, and frameshift mutations in vitro" Proc. Natl. Acad. Sci., 79:1588-1592.

Shumaker et al. (1996) "Mutation Detection by Solid Phase Primer Extension" Human Mutation, 7:346-354.

Sidransky (1997) "Nucleic acid—based methods for the detection of cancer" Science, 278(5340):1054-1057.

Singer et al. (1989) "Effect of 3' flanking neighbors on kinetics of pairing of dCTP or dTTP opposite O6-methylguanine in a defined primed oligonucleotide when *Escherichia coli* DNA polymerase I is used" Proc. Natl. Acad. Sci., 86:8271-8274.

Singer-sam et al. (1992) "A Sensitive, Quantitative Assay for Measurement of Allele—specific Transcripts Differing by a Single Nucleotide" PCR Methods and Applications. 1:160-163.

Smith-Ravin et al. (1995) "Detection of c-Ki-ras Mutations in Fecal Samples from Sporadic Colorectal Cancer Patients," Gut, 36:81-86.

Sokolov, (1989) "Primer extension technique for the detection of single nucleotide in genomic DNA" Nucleic Acids Research, 18(12):3671.

Srinivas et al. (2001) "Trends in biomarker research for cancer detection" The Lancet, 2:698-704.

Stahl et al. (1988) "Solid phase DNA sequencing using the biotin-avidin system" Nucleic Acids Research, 16(7):3025-3038.

Suzuki et al. (2002) "A genomic screen for genes upregulated by demethylation and histone deacetylase inhibition in human colorectal cancer" Nat Genet 31(2):141-9. Epub May 6, 2002.

Syngal et al. (1998) "Benefits of Colonoscopic Surveillance and Prophylactic Colectomy in Patients With Hereditary Nonpolyposis Colorectal Cancer Mutations" Annals of Internal Medicine 129: 787-796.

Syngal et al. (1999) "Interpretation of Genetic Test Results for Hereditary Nonpolyposis Colorectal Cancer" JAMA 282: 247.

Syvanen (1994) 'Detection of Point Mutations in Human Genes by the Solid-phase Minisequencing Method Clinica Chimica Acta, 226:225-236.

Syvanen et al. (1990) "A primer—Guided Nucleotide Incorporation Assay in the Genotyping of Apolipoprotein E" Genomics, 8:684-692.

Syvanen, (1997) "Solid-Phase Minisequencing" Detection of Mutations and Polymorphisms in DNA, Chapter 6, pp. 53-64.

Takeda et al. (1993) "Detection of K-ras Mutation in Sputum by Mutant-Allele-Specific Amplification (MASA)" Human Mutation, 2:112-117.

Thibodeau et al. (1993) "Microsatellite Instability in Cancer of the Proximal Colon" Science, 260:816-819.

Tommasi et al. (2002) "RASSF3 and NORE1: identification and cloning of two-human homologues of the putative tumor suppressor gene RASSF1" Oncogene. 21(17):2713-20.

Toyota et al. (1999) "CpG island methylator phenotype in colorectal cancer" Proc Nat. Acad Sci USA 96:8681-8686.

Traverso et al. (2002) "Detection of APC Mutations in Fecal DNA from Patients with Colorectal Cancer" N Engl. J. Med . . . 346(5):311-320.

Ugozzoli, et al. (1992) "Detection of Specific Alleles by Using Allele—Specific Primer Extension Followed by Capture on Solid Support" CATA 9(4):107-112.

van Engeland et al. (2002) "K-ras mutations and RASSF1 a promoter methylation in colorectal cancer" Oncogene. 21(23):3792-5.

Vasen et al. (1998) "A Cost-Effectiveness Analysis of Colorectal Screening of Hereditary Nonpolyposis Colorectal Carcinoma Gene Carriers" American Cancer Society 82:1632-1637.

Vasen et al. (1999) "New Clinical Criteria for Hereditary Nonpolyposis Colorectal Cancer (HNPCC, Lynch Syndrome) Proposed by the International Collaborative Group on HNPCC" Gastroenterology, 116:1453-1456.

Vavvas et al. (1998) "Identification of Nore1 as a potential Ras effector" J Biol Chem. 273(10):5439-42.

Villa et al. (1996) "Identification of Subjects at Risk for Colorectal Carcinoma Through a Test Based on K-ras Determination in the Stool" Gastroenterology, 110(5):346-1353.

Vogelstein et al. (1999) "Digital PCR," Proc. Natl. Acad. Sci. USA, 96:9236-9241.

Vos et al. (2003) "RASSF2 is a novel K-Ras-specific effector and potential tumor suppressor," J Biol Chem. 278(30):28045-51.

Vos et al. (2004) "A role for the RASSF1 A tumor suppressor in the regulation of tubulin polymerization and genomic stability" Cancer Res. 64(12).4244-50.

Vreeland et al. (2002) "Multiplexed, High-Throughput Genotyping by Single-Base Extension and End- Labeled Free-Solution Electrophoresis" Anal. Chem. 74:4328-4333.

Wada et al. (1983) "Automatic DNA sequencer: Computer-programmed microchemical manipulator for the Maxam-Gilbert sequencing method" Rev. Sci. Instrum., 54(11):1569-1572.

Wagner et al. (2002) "Frequent RASSF1A tumour suppressor gene promoter methylation in Wilms' tumour and colorectal cancer" Oncoqene. 21 (47):7277-82.

Wallace et al. (1979) "Hybridization of Synthetic Oligodeoxyribonucleotides to <DT 174 DNA: the Effect of Single Base Pair Mismatch" Nucleic Acids Research, 6(11):3543-3557.

Walsh et al. (1996) "Sequence Analysis and Characterization of Stutter Products at the Tetranucleotide Repeat Locus vWA" Nucleic Acids Research 24(14):2807-2812.

Walsh et al. (1992) "Preferential PCR Amplification of Alleles: Mechanisms and Solutions" PCR Methods and Applications, pp. 241-250.

Wang et al. (1998) "Large-Scale Identification, Mapping, and Genotyping of Single Nucleotide Olymorphisms in the Human Genome" Science, 280:1077-1082.

Whitney et al. (2004) "Enhanced retrieval of DNA from human fecal samples results in improved performance of colorectal cancer screening test" J Mol Diagn. 6:386-395.

Written opinion for PCT/US05/30942 dated Jul. 26, 2006.

Written opinion for PCT/US05/39670 dated Apr. 12, 2006.

Young et al. (1992) "The Genetics, Epidemiology, and Early Detection of Gastrointestinal Cancers" Current Opinion in Oncology, vol. 4, pp. 728-735.

Zakour et al. (1984) "Site specific mutagenesis: insertion of single noncomplementary nucleotides at specified sites by error-directed DNA polymerization" Nucleic Acids Research, 12(16):6615-6628.

Zhang et al. (2006) "Inactivation of RASSF2A by promoter methylation correlates with lymph node metastasis in nasopharyngeal carcinoma.," International Journal of Cancer, 120:32-38.

Zhou et al. (1997) "Allelic Profiles of Mononucleotide Repeat Microsatellites in Control Individuals and in Colorectal Tumors With and Without Replication Errors" Oncoeene 15: 1713-1718.

Zhou et al. (1998) "Determination of the Replication Error Phenotype in Human Tumors Without the Requirement for Matching Normal DNA by Analysis of Mononucleotide Repeat Microsatellites" Genes. Chromosomes & Cancer 21: 101-107.

Zimmem et al. (1978) "3'-Terminal nucleotide sequence of encephalomyocarditis virus RNA determined by reverse transcriptase and chain-terminating inhibitors" Proc. Natl. Acad. Sci., 75:4257-4260.

Zitt et al. (2007) "DNA methylation in colorectal cancer" Disease Markers 23(1-2):51-71.

Zoller et al. (1982) "Oligonucleotide—directed mutagenesis using M13-derived vectors: an efficient and general procedure for the production of point mutations in any fragment of DNA" Nucleic Acids Research, 10(20):6487-6500.

Behn et al. (1998) "Sensitive detection of p53 gene mutations by a 'mutant enriched' PCR-SSCP technique," Nucleic Acids Res. 26(5):1356-8.

Erickson et al.(2001) "One base sequencing (OBS): an improved method for accurate SNP scoring" Human Genome Meeting (HGM).

Samuels et al. (2004) "High frequency of mutations of the PIK3CA gene in human cancers" Science, 304(5670):554.

Tagore et al. (2003) "Sensitivity and Specificity of a Stool DNA Multitarget Assay Panel for the Detection of Advanced Neoplasia" Clinical Colorectal Cancer, 3(1):47-53.

* cited by examiner

R110 acyclo –TTP dilutions

Load volumes

METHODS FOR ANALYSIS OF MOLECULAR EVENTS

RELATED APPLICATIONS

This application claims priority to, and the benefit of U.S. Ser. No. 60/357,585, filed Feb. 15, 2002, the disclosure of which is incorporated by reference herein.

FIELD OF INVENTION

The invention relates to methods for detection and identification of genetic events in a biological sample. Methods of the invention are useful for disease detection and diagnosis.

BACKGROUND OF THE INVENTION

Many diseases are thought to be associated with genomic instability. Specific nucleic acid variations, such as mutations, insertions, deletions and other alterations can serve as valuable markers for a variety of diseases, including certain types of cancer. For example, mutations in the BRCA genes have been proposed as indications for breast cancer, and mutations in the p53 cell cycle regulator gene have been associated with numerous cancers, especially colorectal cancer. Other diseases that are linked with genomic instability include, for example, sickle cell anemia, phenylketonuria, hemophilia, and cystic fibrosis. Early detection of these variations allow for early disease diagnosis and provide an avenue for treatment before disease symptoms are presented, when a cure is more readily attainable. It has been suggested that specific variations might be a basis for molecular screening assays for the early stages of certain types of cancer. See, e.g., Sidransky, et al., Science, 256: 102-105 (1992). Therefore, in an effort to detect whether certain variations have occurred and further ascertain whether a person is at risk for developing a disease associated with these variations, molecular screening assays have been developed. However, current screening methods are difficult to manage, lack specificity and are not efficient. Furthermore, such screening assays are not reliable for detecting variations that are present in low frequency in the early stages of diseases such as cancer.

Many cancers are curable if detected early in their development. For example, colorectal cancers typically originate in the colonic epithelium, and are not extensively vascularized (and therefore not invasive) during early stages of development. The transition to a highly-vascularized, invasive and ultimately metastatic cancer commonly takes ten years or longer. If the presence of cancer is detected prior to extensive metastasis, surgical removal typically is an effective cure. However, colorectal cancer is often detected only upon manifestation of clinical symptoms, such as pain and black tarry stool or the presence of blood in stool. Generally, such symptoms are present only when the disease is well established, and often after metastasis has occurred. Early detection of colorectal cancer therefore is important in order to significantly reduce its morbidity.

Invasive diagnostic methods, such as endoscopic examination, allow direct visual identification, removal, and biopsy of potentially-cancerous tissue. However, endoscopy is expensive, uncomfortable, inherently risky, and not a practical tool for early diagnosis.

Established non-invasive screening methods involve assaying stool samples for the presence of fecal occult blood or for elevated levels of carcinoembryonic antigen, both of which are suggestive of the presence of colorectal cancer. Additionally, recent developments in molecular biology provide methods of great potential for detecting the presence of a range of DNA variations indicative of colorectal cancer. The presence of such variations can be detected in DNA found in stool samples during various stages of colorectal cancer. However, stool comprises cells and cellular debris from the patient, from microorganisms, and from food, resulting in a heterogeneous population of DNA. This makes detection of small, specific subpopulations difficult to detect reliably.

Attempts have been made to identify and use nucleic acid events that are indicative of cancer and other diseases. However, even when such events are identified, using them to screen patient samples, especially heterogeneous samples, has proven unsuccessful either due to an inability to obtain sufficient sample material, or due to the low sensitivity that results from measuring only a single marker. For example, simply obtaining an adequate amount of human DNA from one type of heterogeneous sample, stool, has proven difficult. See Villa, et al., Gastroenterol., 110: 1346-1353 (1996) (reporting that only 44.7% of all stool specimens, and only 32.6% of stools from healthy individuals produced sufficient DNA for mutation analysis). Other reports in which adequate DNA has been obtained have reported low sensitivity in identifying a patient's disease status based upon a single cancer-associated mutation. See Eguchi, et al., Cancer, 77: 1707-1710 (1996) (using a p53 mutation as a marker for cancer).

Increased knowledge of the molecular basis for disease has lead to a proliferation of screening assays capable of detecting disease-associated nucleic acid variations. One such method identifies a genomic region thought to be associated with a disease and compares the wild-type sequence in that region with the sequence in a patient sample. Differences in the sequences constitute a positive screen. See e.g., Engelke, et al., Proc. Natl. Acad. Sci., 85: 544-548 (1988). However, such methods are time-consuming, costly, and do not have sufficient sensitivity to identify the variation of interest in a heterogeneous sample containing a large amount of non-variant nucleic acid. Thus, sequencing is not practical for large-scale screening assays.

Variations have also been detected by differential hybridization techniques using allele-specific oligonucleotide probes. Saiki et al., Proc. Natl. Acad. Sci., 86: 6230-6234 (1989). Variations are identified on the basis of the higher thermal stability of the perfectly-matched probes as compared to mismatched probes. Disadvantages of this approach for variation analysis include: (1) the requirement for optimization of hybridization for each probe, (2) the nature of the mismatch and the local sequence impose limitations on the degree of discrimination of the probes, and (3) the difficulty in detecting rare variant nucleic acid molecules in heterogeneous populations of nucleic acid. In practice, tests based only on parameters of nucleic acid hybridization function poorly when the sequence complexity of the test sample is high (e.g., in a heterogeneous biological sample). This is partly due to the small thermodynamic differences in hybrid stability generated by single nucleotide changes. In addition, such methods also lack the sensitivity required to detect a small amount of variant nucleic acid in a heterogeneous sample.

A number of detection methods have been developed which are based on template-dependent primer extension. These methods involve hybridizing primers to template nucleic acids and extending the primers using a polymerase. Those methods can be placed into one of two categories: (1) methods using primers which span the region to be interrogated for the variation, and (2) methods using primers which hybridize upstream of the region to be interrogated for the variation. Typically, the primer extension reaction results in an extended product that can indicate the presence of a variant.

Strategies based on primer extension require considerable optimization to ensure that only the perfectly annealed oligonucleotide functions as a primer for the extension reaction. The advantage conferred by the high fidelity of the polymerases can be compromised by the tolerance of nucleotide mismatches in the hybridization of the primer to the template. Any "false" priming will be difficult to distinguish from a true positive signal. The reaction conditions of a primer extension reaction can be optimized to reduce "false" priming due to a mismatched oligonucleotide. However, optimization is labor intensive and expensive, and often results in lower sensitivity due to a reduced yield of extended primer. Also, current primer extension reactions do not reproducibly detect small amounts of variant nucleic acid in biological samples. For this reason, there is a need in the art for additional non-invasive methods for early diagnosis of cancer that will detect early characteristics indicative of the presence of cancer.

SUMMARY OF THE INVENTION

The invention is useful to detect nucleic acid variants or mutations that are present at low frequency in a biological sample. The invention provides methods, compositions, and kits that are useful to detect rare variants or mutations that may otherwise by undetectable in a primer extension assay. According to the invention, a first sequence variant at a predetermined position or target site in a target nucleic acid is detected by performing a primer extension reaction under conditions that prevent misincorporation of a nucleotide that is complementary to the first sequence variant if the target nucleic acid does not contain the first sequence variant at the target site. Accordingly, the specificity of a primer extension reaction is increased by reducing the amount of signal due to misincorporation of a nucleotide complementary to a sequence variant of interest. Typically, the sequence variant of interest is a rare mutation in a heterogeneous biological patient sample such as stool. However, the sequence variant of interest may also be a rare genotype or polymorphism that is present in a heterogeneous sample such as a sample containing a population of viruses or microorganisms or a sample comprised of pooled patient samples. Typically, the nucleotide complementary to the variant of interest is labeled. The invention reduces the amount of background noise due to misincorporation of the label. This allows small amounts of a variant nucleic acid to be detected in a heterogeneous biological sample. The invention also reduces the likelihood of a false positive detection of a variant that is not present in the biological sample. Methods of the invention can also be used to detect the presence of any one of two or three variants at a target position in a target nucleic acid. In one embodiment, the invention includes obtaining a heterogeneous biological sample suspected to contain one or more variant nucleic acids at low frequency. The invention also includes detecting one or more variant target nucleic acids that are present at less than 50%, preferably less than 20%, more preferably less than 10%, more preferably less than 1%, more preferably less than 0.5%, and even more preferably less than 0.1% of the amount of unaltered target nucleic acid in a heterogeneous nucleic acid sample.

In one aspect, a primer extension reaction of the invention prevents misincorporation of a nucleotide complementary to a first variant by including a blocking nucleotide that is complementary to a second variant at the target site. In a typical biological sample of interest, the abundance of nucleic acids containing the first variant is low relative to that of nucleic acids containing the second variant. Accordingly, the specificity of the extension reaction on target nucleic acids containing the first variant is increased by blocking misincorporation on target nucleic acids containing the second variant. The blocking nucleotide is preferably a terminator nucleotide. However, useful blocking may also be obtained using a nucleotide that is extended inefficiently. In some embodiments, useful blocking may also be obtained using a nucleotide that is extended. However, the blocking nucleotide is preferably different from the nucleotide that is complementary to the first variant. The blocking nucleotide is preferably unlabeled or differentially labeled to reduce background noise in the extension reaction. Typically, the first variant is a mutant or polymorphism that is rare relative to the second variant. Accordingly, the first variant can be referred to as an altered nucleotide. The second variant can be referred to as a wild-type nucleotide, a normal nucleotide, or an unaltered nucleotide. Methods of the invention can be used to detect the presence of one or more of several variant nucleotides at a target site in a heterogeneous sample containing an abundant amount of unaltered target nucleic acids. In some embodiments, several labeled nucleotides can be included in a single reaction in order to detect the presence of any one of several mutations that are complementary to the labeled nucleotides. In other embodiments, several different primers are extended in a single reaction using a single labeled nucleotide that is complementary to a mutation adjacent to any one of the primers. This allows several mutations at different genetic loci to be assayed for in one single multiplexed reaction (provided that each of the mutations is due to the presence of the same mutant nucleotide). Under some circumstances, several different primers and several different labeled terminators may be used in a single reaction if the presence of one or two unlabeled blocking nucleotides blocks extension on the unaltered template nucleic acids without blocking extension on a mutant template nucleic acid that is being assayed for. In one embodiment, a screen to detect a mutation indicative of cancer in a patient includes primer extension reactions designed to detect more than one mutation. Preferably, between 2 and 40 mutations are screened for. More preferably, about 20 mutations are screened for. Even more preferably, 21 mutations are screened for. In addition, a deletion at the BAT-26 locus may also be screened for. In particularly preferred embodiments, any two or more of the primers in the Examples are used to screen for the presence of two or more mutations in a patient sample. According to the invention, the detection of any one of the mutations being screened for is indicative of the presence of disease in the patient.

In another aspect, the invention increases the specificity of a detection assay by providing a second polymerase in the extension reaction in addition to the blocking nucleotide. Preferably, the second polymerase preferentially incorporates the blocking nucleotide and the first polymerase preferentially incorporates the nucleotide that is complementary to the first variant at the target site.

In another aspect, the invention provides an internal control to normalize the signal obtained in a primer extension reaction. The internal control is preferably a primer extension reaction that incorporates a control nucleotide that is different from either the first or second nucleotides. The amount of control nucleotide that is incorporated can be used to normalize the observed incorporation of first nucleotide when it is compared to a reference amount indicative of the presence of the first variant in the sample.

Methods of the invention can be used to detect any variant in a biological sample. However, methods of the invention are particularly useful if the variant is a rare variant that is present in less than 20%, less than 10%, and even less than 1% of the target nucleic acids in a sample. Methods of the invention can be used to detect the presence of rare variants that may otherwise be undetectable due to background signal in a primer extension assay. These and other advantages and aspects of the invention will be understood upon consideration of the following detailed description thereof.

DETAILED DESCRIPTION OF THE INVENTION

Figure 1:
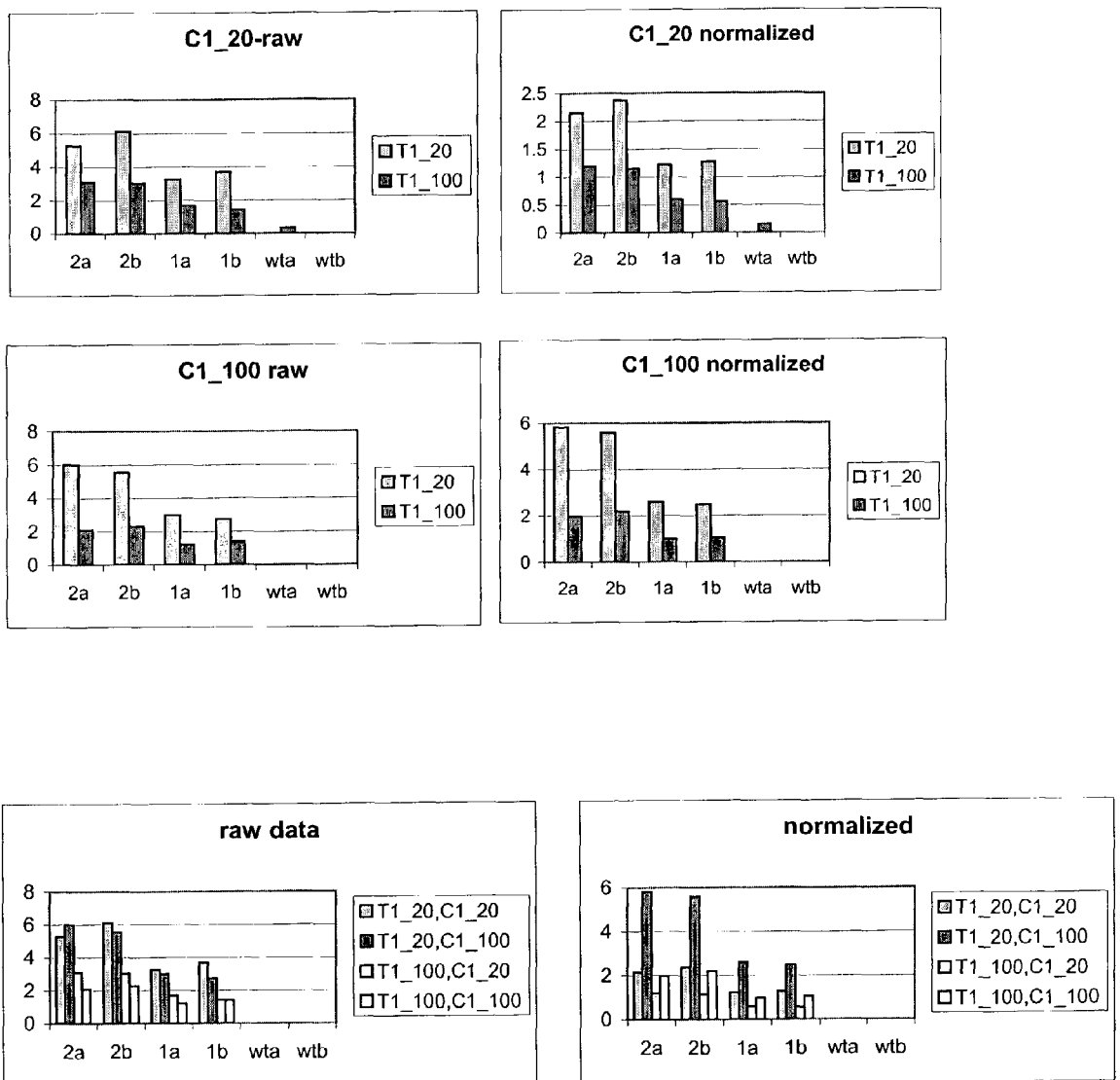
FIG. 1 shows six charts that illustrate the results of four different reaction conditions tested using an internal control sequence.

The invention provides methods and compositions for increasing the sensitivity of primer extension assays for detecting nucleic acid mutations or variations in biological samples.

The invention provides methods for reducing misincorporation of one or more incorrect nucleotides during a primer extension reaction. In general, misincorporation of a mutant or variant nucleotide on a wild-type or unaltered template nucleic acid is reduced by performing a primer extension reaction under conditions that promote incorporation of a correct nucleotide (i.e. wild-type or unaltered) in a primer extension reaction at a target site in the absence of a mutation on the template. Preferably, the incorporation of the correct nucleotide blocks the extension reaction and prevents misincorporation of a mutant or variant nucleotide at that position. According to the invention, a primer extension reaction typically fails to detect a small amount of mutant or variant nucleic acid in a heterogeneous test sample due to nucleotide misincorporation during the extension reaction. For example, nucleotide misincorporation on a wild-type template can result in a background level of incorrectly incorporated mutant nucleotide that conceals a small amount of mutant nucleotide that is correctly incorporated on a small amount of mutant template that may be present in a heterogeneous sample. According to the invention, a significant source of misincorporation results from a correctly hybridized primer being extended with an incorrect nucleotide (i.e. a nucleotide that is not complementary to the template at the position where it is incorporated into the primer extension product). In certain aspects, methods of the invention reduce misincorporation by reducing the number of sites of misincorporation. In further aspects, methods of the invention reduce misincorporation of variant-specific nucleotides and provide highly specific assays for detecting rare variant or mutant nucleic acids in heterogeneous biological samples. Methods of the invention can detect a variant or mutant nucleic acid that represents about 1%, or less, of the target nucleic acid in a heterogeneous nucleic acid sample. The invention is also useful to detect a variant or mutant nucleic acid that represents about 10%, or less; or about 20%, or less of the target nucleic acid in a heterogeneous nucleic acid sample.

Accordingly, the invention provides primer extension methods and kits that are useful for detecting the presence of nucleic acid variations such as insertions, deletions and/or point mutations in heterogeneous biological samples. In one embodiment, methods of the invention are useful to detect variations at loci that are associated with a disease such as cancer. Also, the invention in generally useful to detect variations at loci having a known wild-type nucleic acid.

In general, primer extension methods of the invention comprise identifying a target nucleic acid region suspected of containing a variation, and interrogating the target region using a primer extension reaction. A primer is hybridized to a nucleic acid, preferably a single stranded nucleic acid, in the presence of one or more nucleotides and polymerases, and the primer is extended via the incorporation of one or more nucleotides creating a primer extension product. In one aspect, methods of the invention comprise assays for the analysis of a genomic region suspected to be indicative of disease. In general, methods of the invention comprise annealing a primer near a region in which a variation is suspected to occur, and extending the primer in a template-dependent reaction. Also, in one embodiment, methods of the invention include terminating the extension product at a known end-point. In certain embodiments, the extended primer is labeled downstream of a region suspected to be deleted. In certain embodiments, methods of the invention include providing a terminator nucleotide to block the extension on a wild-type or unaltered template. In some embodiments, an extension nucleotide can be used to block or minimize nucleotide misincorporation on a wild-type or unaltered template. Additionally, more than one type of blocking nucleotide may be used. Preferably, the one or more blocking nucleotides are unlabeled to reduce signal noise from abundant unaltered nucleic acid in a heterogeneous nucleic acid sample. According to the invention, a terminator nucleotide is a nucleotide that can be incorporated into a primer extension product, but that cannot be extended further by a polymerase such as DNA polymerase or other similar enzyme. Useful terminator nucleotides include dideoxy NTPs (ddNTPs), alkynyl acycloterminators, and non-extendable analogs thereof. According to the invention, extension nucleotides are nucleotides that can be incorporated into a primer extension product, and can be extended further by a polymerase such as a DNA polymerase or other similar enzyme. Preferred extension nucleotides include deoxynucleotides (dNTPs) and extendable analogs thereof.

In certain embodiments, the extension reaction is terminated at a site beyond the target region. In other embodiments, the extension product is analyzed, and the product is used as an indicator of the presence or absence of a mutation or variation in the target nucleic acid region. Also, the presence of certain extension products may be indicative of the presence of a deletion in the target region. Conversely, the presence of certain extension products may be generally indicative of the presence of an insertion in the target region. However, the presence of extension product can also be an indicator of a point mutation in the target region, as exemplified in greater detail in the examples that follow.

1. Providing a Blocking Nucleotide to Increase Sensitivity of Primer Extension Assays Certain aspects of the invention are useful for identifying a variation at a predetermined position in a nucleic acid. In one embodiment, methods of the invention include providing a target nucleic acid; contacting the target nucleic acid sequence with a nucleic acid primer substantially complementary to a region of the target nucleic acid sequence to form a nucleic acid complex; extending the nucleic acid primer in the presence of a wild-type nucleotide complementary to a wild-type nucleotide and a variant nucleotide complementary to variant nucleotide, wherein the wild-type extension nucleotide will be incorporated into an extension product on a wild-type target nucleic acid and the variant extension nucleotide will be incorporated into an extension product on a variant target nucleic acid, thereby preventing a wild-type nucleotide from misincorporating opposite a variant base or a variant nucleotide from misincorporating opposite a wild-type base. Preferably, the wild-type nucleotide is unlabeled and the variant nucleotide is labeled. Alternatively, the wild-type extension nucleotide can be labeled with a label that is detectably different than the label of the variant nucleotide. According to a preferred embodiment, the wild-type nucleotide is a terminator nucleotide. Alternatively, or in addition, the variant nucleotide can be a terminator nucleotide. In one embodiment, wild-type and variant nucleotides are the only nucleotides added to the primer extension reaction. However the primer extension reactions can also include other variant-specific nucleotides or internal controls.

Further methods of the invention include providing a target nucleic acid; contacting the target nucleic acid sequence with a nucleic acid primer substantially complementary to the target nucleic acid sequence to form a nucleic acid complex; extending the nucleic acid primer in the presence of an unlabeled extension nucleotide complementary to a variant nucleotide base at a position downstream from the nucleic acid primer in the target nucleic acid sequence to form an unlabeled primer extension product, wherein the extending step is performed in the essential absence of an unlabeled extension nucleotide complementary to a wild-type nucleotide base at a position downstream from the nucleic acid primer; and extending the unlabeled primer extension product in the presence of a labeled extension nucleotide complementary to a corresponding wild-type nucleotide downstream from the position of the variation in the target nucleic acid sequence to form a labeled extension product. A terminator nucleotide corresponding to the unaltered nucleotide at the target position is preferably included in the reaction mixture to block the extension of primers hybridized to unaltered target nucleic acid molecules. This prevents misincorporation of variant nucleotides on unaltered templates.

In another aspect, methods of the invention further include the step of terminating a labeled extension product with a terminator of a nucleic acid primer extension capable of terminating the labeled extension product. In one embodiment, a terminator corresponding to a nucleotide in a corresponding variant and/or wildtype sequence is provided downstream from the labeled extension product.

In another aspect, the invention provides methods for essentially minimizing or reducing background signal when interrogating a target nucleic acid region suspected of containing a variation. Generally, methods of the invention include the steps of contacting a single stranded target nucleic acid sequence with a nucleic acid primer substantially complementary to said target nucleic acid sequence; providing an extension (or a terminator) nucleotide complementary to a variant nucleic acid sequence; and, providing a terminator, wherein the terminator corresponds to a wild-type nucleotide at a potentially variant site such that extension of the nucleic acid primer hybridized to a wild-type nucleic acid is essentially prevented, thereby blocking extension of the wild-type template and minimizing background when interrogating a target nucleic acid suspected of containing a variation.

In one embodiment, a region suspected to contain a deletion comprises a poly-nucleotide tract or repeat in which the deletion is suspected to occur, and the sequence immediately downstream of the region is known and does not repeat a nucleotide species present in the polynucleotide tract. Preferably, the polynucleotide tract comprises three, two, or preferably one, species of nucleotide.

Also, methods of the invention retain the specificity of primer extension assays while increasing their sensitivity by reducing background due to primer extension on a wild-type nucleic acid. Therefore, methods of the invention provide a highly sensitive and highly specific assay for detecting a small amount of variant nucleic acid in a heterogeneous sample of predominantly wild-type nucleic acid. As provided by the examples shown herein, the invention provides for essentially minimizing background by blocking extension of a primer corresponding to wild-type nucleic acid sequences when interrogating a target nucleic acid region suspected of containing a variation. For example, methods of the invention include the steps of contacting a single stranded target nucleic acid sequence with a nucleic acid primer substantially complementary to said target nucleic acid sequence; providing an extension nucleotide complementary to a variant nucleic acid sequence; and, providing a terminator, wherein the terminator corresponds to a wild-type nucleotide at the potentially variant site such that extension of the nucleic acid primer corresponding to a wild-type nucleic acid is essentially prevented, thereby minimizing background when interrogating a target nucleic acid suspected of containing a variation.

Methods of the invention provide screening assays for the detection of a variation in a region of the genome comprising at least one species of nucleotide, and that is characterized by having a sequence for primer hybridization immediately downstream or upstream, and a sequence immediately downstream or upstream that does not contain a nucleotide present in the region suspected to be deleted. Variations can include, for example, nucleic acid insertions, deletions, and point mutations. In a preferred embodiment, methods of the invention comprise selecting a nucleic acid having a known wild-type sequence and having a region where a variation is suspected; hybridizing an oligonucleotide primer, or pair of oligonucleotide primers, immediately downstream or upstream of the target region; extending the primer by using a polymerase in the presence of the nucleotide bases that are complementary to the nucleotide bases of the target region, thereby to form a primer extension product; and, further extending the primer extension product in the presence of a labeled nucleotide that is complementary to a nucleotide base downstream from the target region, but not complementary to a nucleotide base within the target region. Further embodiments may include the step of determining the size of the extension product compared to a standard (e.g., a wild-type product or a molecular weight standard).

In a preferred embodiment, the primer extension product is terminated by incorporating a terminator nucleotide that is complementary to a nucleotide downstream from the target region in a wild type nucleic acid. In certain embodiments, the terminator may not be complementary to any of the nucleotides of the target region. However, in certain embodiments, the terminator may be complementary to a nucleotide of the target region. In an embodiment of the invention, the terminator may correspond to a known variation in the variant nucleic acid. In another embodiment, the terminator may correspond to a known nucleotide in the wild-type sequence. In an alternative embodiment, more than one nucleotide base is incorporated into the extension product prior to incorporation of the terminator nucleotide. In a highly preferred embodiment, an unlabeled nucleotide is incorporated into the extension product prior to the incorporation of the labeled nucleotide. Also, in a highly preferred embodiment, first, the unlabeled nucleotide is incorporated into the nucleic acid primer forming an extension product, and thereafter the labeled nucleotide is incorporated into the extension product.

Furthermore, in another highly preferred embodiment, a terminator is introduced to remove background. In one embodiment, nucleotides incorporated during extension through the region suspected of containing a deletion are unlabeled.

In a preferred embodiment, methods of the invention comprise detecting a nucleic acid variation in a biological sample, such as stool, urine, semen, blood, sputum, cerebrospinal fluid, pus, or aspirate, that contains a heterogeneous mixture of nucleic acid having a deletion in the target region and wild type nucleic acid. Such a deletion in the target region may be present in only about 1-5% of the nucleic acid molecules having the target region. To increase the sensitivity of the assay, the sample may comprise a polymerase chain reaction product. Method of the invention are particularly useful in analyzing a deletion in the target region that is indicative of the presence of cancerous or precancerous tissue in such a biological sample, including colorectal cancer or precancer detection in stool.

In another embodiment, methods of the invention comprise detecting a mutation, such as, for example, a deletion in a sample by selecting a nucleic acid with a known wild-type sequence and having a target region suspected of containing a deletion, wherein the target region contains at least one or at most three different types of nucleotide bases selected from the group consisting of dGTP, dATP, dTTP, and dCTP; hybridizing an oligonucleotide primer to a region adjacent to the target region, in a nucleic acid sample; contacting the hybridized oligonucleotide primer with an extension reaction mixture comprising: i) nucleotides which are complementary to the nucleotides in the target region, ii) a labeled nucleotide which is complementary to a nucleotide found upstream or downstream from the target region, and iii) a terminator nucleotide which is complementary to a nucleotide found upstream or downstream from the target region, but which is not complementary to any nucleotide found in the target region; and extending the hybridized oligonucleotide primer to generate a labeled extension product.

2. Using Two Different DNA Polymerases to Reduce Misincorporation of Nucleic Acids Certain aspects of invention relate to primer extension methods using two or more different polymerases for detecting and identifying variant nucleic acids within a heterogeneous population of nucleic acids. Methods of the invention reduce misincorporation of variant-specific nucleotides in primer extension assays by providing a specific polymerase that preferentially incorporates an unaltered nucleotide in a primer extension reaction in the absence of a sequence variation in the template nucleic acid. According to the invention, a significant source of misincorporation results from a correctly hybridized primer being extended with an incorrect nucleotide (i.e. a nucleotide that is not complementary to the template at the position where it is incorporated into the primer extension product). The invention provides methods for reducing misincorporation by reducing the number of sites of potential misincorporation.

In general, misincorporation is reduced by performing a primer extension reaction in the presence of at least two different nucleotides, one of which is expected to be incorporated into the primer extension product in the absence of a first nucleotide sequence on the template, and the other of which is expected to be incorporated into the primer extension product if the template contains a second nucleotide sequence instead of the first nucleotide sequence. In addition, the primer extension reaction is performed in the presence of at least two polymerases, each of which preferentially incorporates one of the two nucleotides. The polymerase that preferentially incorporates a first nucleotide reduces the possibility of misincorporation of a second nucleotide in primer extension reactions where the template contains a first nucleotide sequence. Preferably, one of the nucleotides is labeled and the other one is not labeled. The labeled nucleotide is preferably the one that is incorporated in the primer extension product when the template contains a sequence to be detected. In alternative embodiments, both first and second nucleotide may be labeled if they are differentially labeled such that the label on one of the nucleotides is detectably different from the label on the other nucleotide.

According to the invention, reducing the rate of misincorporation increases the sensitivity of primer extension assays and allows for the detection of rare nucleic acid variations in heterogeneous biological samples. Misincorporation of a nucleotide corresponding to a mutation in a primer extension reaction can lead to a false positive detection of the presence of the mutation in a nucleic acid sample. In a typical primer extension reaction on a biological sample that contains mostly wild-type nucleic acids, misincorporation results in a background level of false positive signal that is high enough to obscure a true positive signal generated from a relatively small amount of mutant nucleic acids. Therefore, by reducing the amount of misincorporation, aspects of the invention provide highly sensitive and highly specific assays for detecting rare variant and/or mutant nucleic acid in heterogeneous biological samples.

Aspects of the invention involve using two different polymerases; a first polymerase that preferentially incorporates a first nucleotide and a second polymerase that preferentially incorporates a second nucleotide. In one aspect, the first nucleotide can be a variant nucleotide and the second nucleotide can be an unaltered or wild-type nucleotide. In further aspects of the invention, the first nucleotide can be a polymorphism or other alteration, such as a deletion, insertion or point mutation. Having both polymerases present when performing a primer extension reaction reduces the risk of a variant nucleotide binding to a wild-type base, causing a false positive result when screening for nucleic acid variations. Additionally, this method reduces the risk of a wild-type nucleotide binding to a variant base, causing a false negative result when screening for nucleic acid variations.

Primer extension methods of the invention generally comprise identifying a target nucleic acid region suspected of containing a variation, and interrogating the target region using a primer extension reaction. A primer is hybridized to a single stranded nucleic acid in the presence of extension nucleotides and polymerases, and the primer is extended through the target region creating a primer extension product.

In one embodiment, a method of the invention includes the steps of contacting a single stranded target nucleic acid with a nucleic acid primer substantially complementary to said target nucleic acid sequence; providing an extension nucleotide complementary to a variant nucleic acid sequence; and providing a terminator, wherein the terminator corresponds to a wild-type nucleotide at the potentially altered site such that extension of the nucleic acid primer corresponding to a wild-type nucleic acid is prevented. In an alternate embodiment, the extension nucleotide is complementary to a wild-type nucleic acid sequence and the terminator corresponds to a variant nucleotide at the potentially altered site such that extension of the nucleic acid primer corresponding to a variant nucleic acid is prevented.

In further embodiments, a primer is designed to bind and begin hybridization at the base suspected of containing a variant and will only bind and extend if a variant base is present. Alternatively, the primer can be designed to bind and begin hybridization at the base suspected of containing a variant and will only bind and extend if a wild-type base is present. In other embodiments, the primer is designed to bind and begin hybridization at a base upstream from the target region suspected of containing a variant base, and will only extend through the target region if a variant base is present in the target region. Alternatively, the primer can be designed to bind and begin hybridization at a base upstream from the target region suspected of containing a variant base, and will only extend through the target region if no variant base is present.

In another embodiment, the method involves the steps of contacting a single stranded target nucleic acid sequence with a nucleic acid primer substantially complementary to the target nucleic acid sequence, and providing a labeled extension nucleotide complementary to a variant nucleic acid sequence such that the presence of a labeled extension product indicates the presence of a variant in the target nucleic acid region. Alternatively, the method involves the steps of contacting a single stranded target nucleic acid sequence with a nucleic acid primer substantially complementary to the said target nucleic acid sequence, and providing a labeled extension nucleotide complementary to a wild-type nucleic acid sequence such that the presence of a labeled extension product indicates the lack of a variant in the target nucleic acid region. In a further embodiment, the extension nucleotide complementary to an altered nucleic acid sequence is labeled with a first label and the extension nucleotide complementary to a wild-type nucleic acid sequence is labeled with a second label. The first label is different than the second label and can be visually differentiated from the second label.

The extension product can be analyzed and used to indicate the presence or absence of a variant in the target region. The presence of certain extension products can be an indicator of the presence of an insertion, deletion, point-mutation or other alteration within the target region. In one embodiment, methods of the invention are useful in detecting nucleic acid methylation.

Polymerases with Preferential Incorporation:

Preferential incorporation of one terminator over another can be measured by running parallel reactions which differ only in the type and concentration of each terminator. The relative incorporation efficiency of two different terminators can be reflected in the concentrations of terminators in the two reactions. For example, a first reaction that contains 10-fold more of a first terminator than a second reaction containing a second terminator demonstrates that insertion of the first terminator is 10-fold less efficient than that of the second terminator. These concentration levels can be measured by various methods, including, for example, performing titration assays, running the samples on DNA sequencing gel and visualizing the extent of terminator incorporation by autoradiography. If the incorporation of a first terminator over a second terminator is a 10-fold or greater difference, a determination can be made that the first terminator was preferentially incorporated. Preferably, a first polymerase incorporates a first polymerase with between a 2 fold and a 100 fold preference. More preferably, the ratio of incorporation is between 5 fold and 50 fold. Even more preferably, the ratio is about 10 fold. However, ratios less than 2 fold and greater than 100 fold can also be useful. The preference of the first polymerase for the first nucleotide relative to the second nucleotide can also be measured as a percentage increase in incorporation in an assay. Preferably, a first polymerase has between about a 5% and a 100% preference for a first type of nucleotide relative to a second type of nucleotide. More preferably, the preference is between 25% and 75%. Examples of DNA polymerases that preferentially incorporate dideoxy terminators include Taq polymerase and Thermo Sequenase. (Gardner, A., (2002) "Acyclic and dideoxy terminator preferences denote divergent sugar recognition by archaeon and Taq DNA polymerases", Nucleic Acids Research, Vol. 30, No. 2 pp. 605-613.) Examples of DNA polymerases that preferentially incorporate acyclic terminators include Vent, Vent A488L, Deep Vent, 9° N and Pfu. In one embodiment of the invention, preferential incorporation can also be achieved by using dye-labeled terminators. Examples of DNA polymerases that preferentially incorporate dye-labeled terminators include Vent DNA polymerase, which preferentially incorporates dye-labeled dCTP analogs over unmodified dCTPs, and dye-acyCTPs over dye-ddCTPs, and Vent, Deep Vent, Pfu and 9° N polymerases, which preferentially incorporate dye-acyNTPs over dye-ddNTPs.

Applications

Methods of the invention are useful in the context of detecting a rare mutation in a heterogeneous biological sample (e.g. a sporadic mutation in a heterogeneous patient sample); detecting rare genotypes in genotyping reactions (e.g. viral genotyping reactions); detecting mutant or variant sequences in pooled samples (e.g. detecting polymorphisms or inherited sequence variations in pooled patient samples).

3. General Considerations

Methods of the invention also provide screening assays for the detection of a variation in a region of the genome comprising at least one species of nucleotide, and that is characterized by having a sequence for primer hybridization immediately downstream or upstream, and a sequence immediately downstream or upstream that does not contain a nucleotide present in the region suspected to contain a variant. In one embodiment, methods of the invention comprise selecting a nucleic acid having a known wild-type sequence and having a region where a variant is suspected; hybridizing an oligonucleotide primer, or pair of oligonucleotide primers, immediately downstream or upstream of the target region; extending the primer by using a polymerase in the presence of the nucleotide bases that are complementary to the nucleotide bases of the target region, thereby to form a primer extension product; and, further extending the primer extension product in the presence of a labeled nucleotide that is complementary to a nucleotide base downstream from the target region, but not complementary to a nucleotide base within the target region. Further embodiments may include the step of determining the size of the extension product compared to standard (e.g., a wild-type product or a molecular weight standard). In some embodiments, the target nucleic acid is denatured. In some embodiments, the primer is exactly complementary to the target region. In alternative embodiments, the primer may contain at least one or two mismatches in order to reduce the generation of background signal observed after the extension reaction. The nucleic acid primer is preferably a DNA primer or analog thereof. However, the primer may also be a PNA, RNA, or analog thereof.

In one embodiment, methods of the invention can be performed in parallel, whereby the primer extension reaction is run in parallel with more than one biological sample. Such reactions can be run by using a multi-well plate in which one biological sample is placed in each well and each primer extension reaction is performed separately within each well. Each well may contain the same or different biological samples than each of the other wells.

In another embodiment, methods of the invention comprise extending the primer extension product in the presence of labeled and unlabeled nucleotides, the nucleotides being of the same type (e.g., A, T, C, or G) and being complementary to one or more nucleotides downstream from the target region but not complementary to a nucleotide within the target region. In one embodiment the ratio of the labeled nucleotide to unlabeled nucleotide is 1:1. Methods of the invention may also include incorporating more than one monomer of the labeled nucleotide or unlabeled nucleotide into the extension product.

The invention provides for terminators that comprise nucleotides, nucleotide analogs, dideoxynucleotides, or other known molecules appropriate for the invention. In certain embodiments, the invention provides for the use of terminators comprising dideoxynucleotide triphosphates (ddNTP), such as, for example, dideoxyadenosine triphosphates (ddATP), dideoxycytosine triphosphates (ddCTP), dideoxyguanosine triphosphates (ddGTP), dideoxythymidine triphosphates (ddTTP), or dideoxyuridine triphosphates (ddUTP). Other embodiments of the invention provides for the use of other terminators or primers commonly known to those skilled in the art.

In certain embodiments, the terminators may not be detectably labeled. In other embodiments, however, the terminators may be detectably labeled. Terminators may comprise labels such as a fluorophore, a chromophore, an isotoptically labeled moiety, an enzymatic label, or a radioactive label. Other embodiments provide for other labels commonly known to those skilled in the art. Alternate embodiments include a plurality of labels, such as the use of more than one fluorophores to differentiate the detection of particular nucleotides. In another embodiment, the first nucleotide is labeled in similar manner, and the second nucleotide is unlabeled. Furthermore, in certain aspects, extension nucleotides may be detectably labeled in a similar manner.

Methods of the invention are also useful to detect small amounts of hypermethylated template in a heterogeneous biological sample. Hypermethylation can be indicative of the presence of a disease such as cancer. For example, hypermethylation of any one of the APC, hMLH, P16, MGMT, P14, HLTF, MINT31, and MINT2 loci, particularly in the 5' region of the gene, can be indicative of cancer. Particularly useful primers for detecting hypermethylation at a genetic locus are primers that hybridize to a template nucleic acid upstream or immediately adjacent to a position (a CpG) suspected to be methylated if the target genetic locus is hypermethylated. According to the invention, a target nucleic acid sample is treated with bisulfite to modify the unmethylated CpG dinucleotides. The bisulfite reaction modifies the C to a U in an unmethylated CpG dinucleotide. Accordingly, bisulfite modification of a heterogeneous nucleic acid sample containing a small amount of methylated CpG at a predetermined position produces a small amount of target nucleic acid a C and a large amount of target nucleic acid with a U at the predetermined position. The invention allows detection of the small amount of C by including A nucleotide (along with G nucleotide) in the extension reaction to prevent misincorporation of a G nucleotide on a template containing a U at the predetermined position. As discussed above, the A is preferably unlabeled and is preferably a terminator nucleotide. A second polymerase may also be used in this assay as discussed above.

In further embodiments, the invention includes the step of running the primer extension reaction using an internal control nucleic acid having a different nucleotide sequence than the wild-type and the variant. The control nucleotide is complementary to a corresponding control template nucleotide sequence and is not incorporated into the extension product of either a normal or variant primer extension reaction. The control extension nucleotide is preferably labeled. In one embodiment, an internal control nucleic acid can be added to a reference primer extension reaction containing 99% known wild-type template nucleic acid and 1% known variant template nucleic acid in order to generate 1) a labeled primer extension product in which a labeled variant-specific nucleotide has been incorporated and 2) a labeled primer extension product in which a labeled control nucleotide is incorporated. The extension products can provide a reference signal to determine whether the amount of signal produced by a suspected variant in a biological sample reflects a true positive or a true negative result, or whether the variant signal is the result of other reaction conditions. Accordingly, the control signal is used to determine whether the signal from the labeled variant-specific nucleotide is indicative of the presence of a rare variant in a biological sample. The signal strength generated by a primer extension reaction designed to detect a mutant or variant can be compared to the signal strength of the internal control to determine the relative strength of the mutant or variant-specific signal. According to the invention, different percentage concentrations of internal control template can be used to generate a reference level for determining whether a rare variant is present.

According to the invention, the internal control nucleic acid can be included in each primer extension reaction performed using a biological sample of interest so that the signal corresponding to the control can be compared to any signal corresponding to a possible rare variant, therefore providing a reference signal for use in determining whether a rare variant is actually present. A control nucleic acid can be used in conjunction with two different polymerases and does not interfere with the preferential incorporation of a wild-type or variant nucleotide. In a preferred embodiment, the control nucleotide is a terminator nucleotide. In a preferred embodiment, the same lot of labeled nucleotides for the internal control and the same lot of labeled nucleotides for the variant are used throughout each primer extension reaction. This prevents signal fluctuations among different dye lots, which could otherwise be interpreted as false positives or false negatives.

Methods of the invention are especially useful to detect indicia of cancer or precancer in a heterogeneous sample. Stool is a good example of a heterogeneous sample in which methods of the invention are useful. A typical stool sample contains patient nucleic acids, but also contains heterologous nucleic acids, proteins, and other cellular debris consistent with the lytic function of the various nucleases, proteinases and the like found in the colon. Under normal circumstances, stool solidifies as it proceeds from the proximal colon to the distal colon. As the solidifying stool passes through the colon, colonic epithelial cells are sloughed onto the stool. If a patient has a developing tumor or adenoma, cells from the tumor or adenoma will also be sloughed onto stool. Those cells, and/or their debris, will contain molecular indicia of disease (e.g., variations or loss of heterozygosity). In the early stages of development, nucleic acid indicative of an adenoma or tumor comprise only about 1% of the nucleic acid in a voided stool. If left untreated, proportionately more disease-related nucleic acids are found in stool. Methods of the invention are useful for detecting early-stage lesions in heterogeneous samples such as stool. Methods of the invention result in a high degree of sensitivity and specificity for the detection of early-stage disease. Methods of the invention are especially useful in detecting, for example, adenomas in the colon. Adenomas are non-metastatic lesions that frequently have the potential for metastasis. If all adenomas in a patient are detected and removed, the probability of complete cure is virtually certain.

Mutations, such as deletions in the various loci, such as, for example, BAT26, APC, DCC, p53, and Kras have been associated with cancer, such as, for example colorectal cancer. Thus, in a highly-preferred embodiment, the region in which a deletion is suspected to occur is in the BAT26, APC, DCC, p53 and/or Kras locus. Use of methods of the invention on certain loci identifies the characteristic variations (deletions, insertions, point mutations or other alterations) by producing an extension product in affected nucleic acids that is different than the expected wild-type extension product.

Also, in another aspect, methods of the invention provide methods for identifying indicia of cancer in tissue or body fluid samples by interrogating non-apoptotic DNA in those samples. The invention also provides methods for identifying indicia of cancer or precancer in samples containing exfoliated epithelial cells. It has now been recognized that DNA obtained from exfoliated normal (non-cancerous) cells is different than DNA obtained from exfoliated cancer or precancer cells. Normal exfoliated cells typically have undergone apoptosis, and thus produce cells or cellular debris (depending upon the stage of apoptosis) comprising DNA that has been substantially degraded. Exfoliated cancer or precancer cells typically have not undergone apoptosis, and such cells or their debris, while producing some very small fragments as a result of degradation in the sample, typically also contain a higher proportion of large DNA fragments (compared to those observed in cells or debris from exfoliated normal cells). According to the invention, the difference in DNA integrity between normal and abnormal cells is not only a marker for the presence of cancer or precancer in a sample comprising exfoliated cells, but can also be used to preferentially interrogate mutant DNA by interrogating high integrity nucleic acid.

Stool is a good sample for exemplification of methods of the invention. The colonic epithelium undergoes a continual process of exfoliation. Normal epithelial cells undergo apoptosis, and are sloughed into the lumen of the colon, and onto forming stool. Cells from polyps and tumors are also sloughed onto forming stool. However, cells from polyps or tumors are typically not apoptotic. Methods of the invention take advantage of the different characteristics between apoptotic and non-apoptotic cells in order to screen patient samples for indicia of cancer or precancer.

As noted above, non-cancerous (normal) cells undergo apoptosis at regular intervals, or in response to irreparable cell damage. As a result of apoptosis, DNA from normal cells is cleaved into small fragments having about 200 or fewer base pairs, and typically 180 base pairs or less. In contrast, DNA obtained from cancer or precancer cells is much larger than the typical apoptotic fragments. Thus, the presence of large DNA fragments in a sample (e.g., of sloughed colonic epithelium) indicates that there are or were cells in the sample (or the specimen from which it was obtained) that have avoided apoptosis, and its coincidental degradation of DNA. The presence of large DNA fragments represents a positive screen for cancer or precancer.

Accordingly, methods of the invention comprise detecting the presence in a biological sample of species-specific nucleic acids indicative of cancer or precancer. Samples comprising such nucleic acids are identified as having indicia of cancer or precancer. In preferred methods, patients presenting samples having a high proportion of non-apoptotic nucleic acids as determined by methods of the invention are further evaluated for the presence of a tumor, adenoma, or other cancerous or precancerous lesion.

In one aspect, methods of the invention comprise interrogating in a biological sample one or more DNA fragment(s) of a length that would not be substantially present in noncancerous cells or cellular debris. In a preferred embodiment, such fragments are larger than a typical apoptotic spindle fragment, or larger than about 170 base pairs. However, also in a preferred embodiment, methods of the invention comprise interrogating DNA fragments that are greater than about 200 base pairs, and preferably greater than about 500 base pairs. There is no upper limit on these fragments, as all that is necessary is that the fragment be larger than an apoptotic fragment. Typically, however, fragments indicative of cancer or precancer cells are between about 200 and about 3500 base pairs, and ideally between about 500 and about 2500 base pairs.

In the present invention, useful biological samples include any sample from a patient in which a target nucleic acid region is present. These samples can be prepared from any cell, tissue, or body fluid. Biological cell sources include, for example, blood cells, colon cells, buccal cells, cervicovaginal cells, epithelial cells from urine, fetal cells or cells present in tissue obtained by biopsy. Tissues and body fluids include, for example, sputum, pancreatic fluid, bile, lymph, plasma, urine, cerebrospinal fluid, seminal fluid, saliva, breast nipple aspirate, pus, amniotic fluid and stool. Biological samples can also include isolated nucleic acid obtained from any cell, tissue or body fluid of a patient. The nucleic acid can be isolated by any method that is standard in the art and the isolation method will depend on the source of the biological sample.

In one embodiment, one or more specific regions of the target nucleic acid are amplified using any known methods of amplification, such as polymerase chain reaction (PCR). In certain embodiments, the comparative length and/or molecular weight of the extended primer is determined by gel electrophoresis or mass spectroscopy. In further embodiments, detecting labeled products may be performed by capillary electrophoresis or other methods commonly known to those skilled in the art.

Aspects of the invention also comprise kits containing all of the appropriate reagents and material for preparing and conducting the primer extension and/or DNA integrity assays described herein.

Additional aspects of the invention are described in the following sections and illustrated by the following examples.

EXAMPLES

Example 1

Variation Detection at Specific Loci

Experiments were conducted to demonstrate the usefulness of the primer extension invention to detect mutations in the various loci known to be related to colorectal cancer. For example, primer extension protocols were designed using the methods of the invention to detect variants at various loci known to be related to colorectal cancer.

Choosing the Target Region and the Oligonucleotide Primer

Preferably, a locus associated with a disease such as cancer is chosen. Most preferably, a locus that is known to frequently exhibit one or more mutations, such as deletions or point mutations is chosen. Preferably, a chosen locus comprises a nucleotide in which a mutation is suspected to occur. Once a locus is chosen, primers are designed or chosen to maximize specificity of binding to a nucleotide sequence adjacent to the region suspected of containing a mutation. Particularly useful primers are described in this and the following examples.

Sample Preparation and Hybridization

Methods of the invention are performed on any tissue or body fluid, including biopsy samples, and others having a high concentration of affected (i.e., mutated) cells or cellular debris. However, methods of the invention are particularly useful for detecting variations in heterogeneous biological samples. A preferred sample is stool. For the analysis of stool samples, preferred methods of the invention comprise obtaining at least a cross-section or circumferential portion of a voided stool as taught in U.S. Pat. No. 5,741,650, and co-pending, co-owned U.S. patent application Ser. No. 09/059,718, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA), as taught in co-pending, co-owned U.S. patent application Ser. No. 60/122,177, incorporated by reference herein. It has been discovered that the use of at least 16 mM EDTA, and preferably 100 mM EDTA greatly improves the yield of nucleic acid from stool. Thus, a preferred buffer for stool homogenization comprises phosphate buffered saline, 20-100 mM NaCl or KCl, at least 16 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed.

Nucleic acids to be analyzed are chosen based upon known or suspected relationships between specific mutations and cancer or precancer. If desired, sequence-specific hybrid capture is used to isolate specific nucleic acids from the sample. Target nucleic acids may be analyzed by any method of the art. However, target nucleic acids isolated using the capture probes described herein are preferably analyzed using the primer extension assays or DNA integrity methods of the invention. In addition to the detection of the presence of a variation using detection tools such as capillary electrophoresis and other fluorescent detecting methods, other examples of methods for analysis include enumerative analysis of the loss of heterozygosity as taught in U.S. Pat. No. 5,670,325, incorporated by reference herein. Enumerative methods do not require knowledge of the sequence of a variant nucleic acid. Rather such methods determine that there has been an alteration (deletion, substitution, addition, rearrangement, or other mutation) in a wild-type nucleic acid. The investigated loci are chosen based upon the likelihood of an alteration being associated with cancer or precancer. Enumerative methods can be used to compare the number in a sample of a wild-type nucleic acid known not to be altered in cancer or precancer with the number of a wild-type nucleic acid known or suspected to be altered in cancer or precancer. A statistically-significant difference in the two numbers indicates a positive screen. In preferred enumerative methods, a number of molecules containing a first SNP (single nucleotide polymorphism) is compared to a number of molecules containing a second SNP, and the presence of a statistically significant difference is indicative of the presence of diseased, cancerous, or precancerous cells.

Useful primer sequences for sequence specific capture are shown in Table 1. Table 1 provides information regarding the size, percent G/C and TM information for each capture probe.

TABLE 1

Capture Probe Sequences

| Name | Sequence 5'-3' | % GC | TM ($^2/_4$ rule) | TM (nearest neighbor) | SEQ. ID NO: |
| --- | --- | --- | --- | --- | --- |
| CAP-A | Gtggagtatttgatagtgtattaaccttatgtgtgac | 35% | 100 | 75 | 1 |
| CAP-B | Ttccagcagtgtcacagcaccctagaaccaaatccag | 51% | 112 | 89 | 2 |
| CAP-C/D | Cagatagccctggacaaaccatgccaccaagcagaag | 54% | 114 | 91 | 3 |
| CAP-E | Tactcccctgccctcaacaagatgttttgccaactgg | 51% | 112 | 90 | 4 |
| DAP-F1 | Atttcttccatactactacccatccacctctcatc | 43% | 100 | 79 | 5 |
| CAP-F2 | Atgaggccagtgcgccttggggagacctgtggcaagc | 65% | 122 | 97 | 6 |
| CAP-G | Gaaaggacaagggtggttgggagtagatggagcctgg | 57% | 116 | 90 | 7 |
| CAP-J1 | Ttaagaatttaaaaatcgaagatttctataccactgg | 27% | 94 | 77 | 8 |
| CAP-J2 | Acagatagtgaagaaggcttagaaaggagctaaaaga | 38% | 102 | 79 | 9 |
| CAP-L | Gaagttcctggattttctgttgctggatggtagttgc | 46% | 108 | 86 | 10 |
| CAP-M | Gattctgaagaaccaactttgtccttaactagctctt | 38% | 102 | 79 | 11 |

TABLE 1-continued

Capture Probe Sequences

| Name | Sequence 5'-3' | % GC | TM ($^2/_4$ rule) | TM (nearest neighbor) | SEQ. ID NO: |
|---|---|---|---|---|---|
| CAP-N | Ctaagtttgaatccatgctttgctcttcttgattatt | 32% | 98 | 80 | 12 |
| CAP-P | Aagaggagctgggtaacactgtagtattcaaatatgg | 41% | 104 | 80 | 13 |
| CAP-Q | Gaatgtattatttctgccatgccaacaaagtcatcac | 38% | 102 | 83 | 14 |
| CAP-K1 | Tcagaagggagaaacacagtctggattattacagtgc | 43% | 106 | 83 | 15 |
| CAP-K2 | Aattatagtttttattttttgagtctttgctaatgcc | 24% | 92 | 76 | 16 |
| CAP-R1 | Catgtgctgtgactgcttgtagatggccatggcgcgg | 60% | 118 | 96 | 17 |
| CAP-R2 | Gcaactggggtctctgggaggaggggttaagggtggt | 62% | 120 | 93 | 18 |
| CAP-S1 | Gaatgtattatttctgccatgccaacaaagtcatcac | 38% | 102 | 83 | 19 |
| CAP-S2 | Cttctgcttggtggcatggtttgtccagggctatctg | 54% | 114 | 91 | 20 |
| CAP-T1 | Agaagtacatctgctaaacatgagtggggtctcctga | 46% | 108 | 84 | 21 |
| CAP-T2 | gcagttcagagggtccaggttcttccagatgctgata | 51% | 112 | 88 | 22 |

The capture probe sequences are preferably modified with a 5'-biotin. CAP-A is used to capture the sequences at KrasCp2 locus. CAP-B and CAP-C/D are used to capture sequences at the APC locus. CAP-E, CAP-F1, CAP-F2, and CAP-G are used to capture sequences at the p53 locus.

Primer Extension, Labeling and Termination.

A hybridized primer is extended through a target region suspected of containing a variation at a target position using known reagents for primer extension, including extension using DNA polymerases. At least one of the extension nucleotides preferably is labeled using a detectable label. Preferably, a labeled nucleotide is added to the extended primer once extension through a target position containing a variation is complete. In a preferred embodiment, the labeled extension reaction is terminated at a predetermined position downstream from the target position. In an embodiment, the labeling and termination steps are performed simultaneously. In a preferred embodiment a labeled nucleotide is incorporated into the extended primer downstream from the target position. Also, in a preferred embodiment, an unlabeled terminator is incorporated into the extended primer downstream from the labeled nucleotide. Furthermore, in certain embodiments, the labeling and termination steps are performed separately. According to the methods of the invention, labeling and termination reactions are performed downstream from the target position. According to the methods of the invention, an unlabelled terminator nucleotide is preferably provided to prevent extension of primers hybridized adjacent to a wild-type nucleotide at a target position suspected of containing a variation. Accordingly, background due to extension through the wild-type nucleotide at the target position is reduced or essentially eliminated.

Accordingly, preferred methods of the invention comprise providing a primer that specifically hybridizes to a target nucleic acid upstream (5') from a target position suspected of being variant. The hybridized primer is preferably extended in the presence of unlabeled nucleotides that are only incorporated if a variation is present at the target position, and in the essential absence of unlabeled nucleotides that are incorporated if a wild-type nucleotide is present at the target position. An extended primer containing a variant sequence is labeled by further extending the primer in the presence of a labeled nucleotide that is complementary to a wild-type nucleotide at a labeling position downstream (3') (preferably immediately downstream) from the target position. One of ordinary skill in the art will appreciate that the labeled nucleotide is preferably not complementary to the wild-type nucleic acid at the target position. The labeled nucleotide may be an extension nucleotide or alternatively a terminator nucleotide. In one embodiment, the labeled extension product is terminated by including a terminator nucleotide that is complementary to a wild-type nucleotide downstream from the labeling position. One of ordinary skill in the art will appreciate that this terminator nucleotide is preferably not complementary to the variation at the target position or the wild-type nucleotide at the labeling position. Preferably, in order to reduce background labeling due to incorrect extension through a wild-type nucleotide at the target position, an unlabeled terminator complementary to the wild-type nucleotide at the target position is added to cap primers hybridized to wild-type target nucleic acids. In one embodiment, the unlabeled terminator used for capping primers hybridized to wild-type nucleic acids is the same as the terminator that terminates extension of the labeled variant extension products.

The label is preferably a fluorescent tag. Alternatively a radioactive isotope, a molecular weight tag or other detectable label may be incorporated. Various labels are commonly used by those skilled in the art.

Detection and Analysis of the Extension Product

While unlabeled primer extension products are contemplated, in preferred methods of the invention, only extension products that have been extended through the region suspected of containing a variation, such as a deletion, are analyzed, because they are the only extension products that contain a detectable label according to the preferred methods of the invention.

Extended primer products are preferably detected using methods known in the art for detecting labeled oligonucleotides. In some embodiments, useful methods include gel electrophoresis, mass spectroscopy, capillary electrophoresis, sequencing, and other methods for determining the differential length of two primers.

The following examples illustrate practice of the invention using mutation detection in various loci on samples prepared from biological specimens. Also, below are certain illustrative examples of primer extension assays used to detect variations in a biological sample, and therefore diagnose disease in a patient from whom the sample is obtained.

Example 2

Read-Through Primer Extension Protocol

A typical read-through primer extension reaction is shown as follows:

| | |
|---|---|
| ~XXXXXXXX-$N_1$-$N_2$*-T | (extended primer sequence) |
| ~XXXXXXXX-X-X-X | (extended product on the template sequence) |

In the extended primer, $N_1$ is an unlabeled deoxynucleotide triphosphate, $N_2$* is a labeled deoxynucleotide triphosphate (the identity of this labeled nucleotide is preferably different from the unlabeled nucleotide), T is an unlabeled terminator (e.g. unlabeled dideoxynucleotide triphosphate), and X represents an unspecific nucleotide that is defined by the sequence of the target template sequence to which the primer is designed to hybridize.

The unspecific nucleotides in the template sequences can be, for example, A, C, G, or T, and the sequence of the primer is designed to hybridize with the template sequence according to standard Watson-Crick base-pairing rules. The unlabeled deoxynucleotide triphosphate, labeled deoxynucleotide triphosphate, and unlabeled terminator (e.g. unlabeled dideoxynucleotide triphosphate) are added in a primer extension reaction such that the unique bases are added according to the sequence shown by the formula provided above (i.e., ~$N_1$-$N_2$*-T) for a given mutation, wherein the identity of $N_1$ and $N_2$ are preferably different.

In a typical reaction, a 5 µl extension reaction is performed and the extension products are analyzed by capillary electrophoresis. A typical 5 µl reaction contains 1 µl of 10× reaction buffer, 1 µl of 5 µM primer, 0.05 µl of thermal sequencing enzyme (e.g. thermosequenase at 32 U/µl), 1 µl of each unlabeled terminator or extension nucleotide (50 µM) that is included in the reaction, and 0.05 µl of each labeled terminator or extension nucleotide that is included in the reaction. Water is added to generate a 5 µl reaction.

Example 3

Variation Detection at APC (876)

Variants or mutants are detected at APC (876) using a primer with a sequence that is shown underlined in the following a APC nucleotide sequence:

(SEQ ID NO:23)

ggcaacatgactgtcctttcaccatatttgaatactacagtgttacccagctcctcttcatcaagaggaagcttagatagttctcgttctgaaaaa gatagaagtttggagagagaacgcggaattggtctaggcaactaccatccagcaacagaaa<u>atccaggaacttcttcaaag</u>ggaggtttgc agatctccaccactgcagcccagattgccaaagtcatggaagaagtgtcagccattcatacctctcaggaagacagaagttctgggtctacc actgaattacattgtgtgacagatgagagaaatgcacttagaagaagctctgctgcccatacacattcaaacacttacaatttcactaagtcgg aaaattcaaataggacatgttctatgccttatgccaaattaga The following primer and extension product sequences are shown in a 5' to 3' orientation. The following nucleic acid primer and nucleotides are added to the extension reaction:

Nucleic Acid Primer (P1): atccaggaacttcttcaaag (SEQ ID NO:24)

Nucleotides: 1. Unlabeled deoxyguanosine triphosphate (dGTP) ("g")

2. Labeled dideoxyadenosine triphosphate (ddATP) (a*)

The following extension products are obtained for wild type (wt) and mutant (mt) templates:

```
wt-atccaggaacttcttcaaaggga*    (SEQ ID NO:25)
mt-atccaggaacttcttcaaaga*      (SEQ ID NO:26)
```

Example 4

Variation Detection at APC (1554)

Variants or mutants are detected at APC (1554) using a primer with a sequence that is shown underlined in the following a APC nucleotide sequence:

(SEQ ID NO:27)

```
tctgagcctcgatgagccatttatacagaaagatgtggaattaagaataatgcctccagttcaggaaaatgacaatgggaatgaaacagaatc agagcagcctaaagaatcaaatgaaaaccaagagaaagaggcagaaaaaactattgattctgaaaaggacctattagatgattcagatgat gatgatattgaaatactagaagaatgtattatttctgccatgccaacaaagtcatcacgtaaaggcaaaaagccagcccagactgcttcaaaat tacctccacctgtggcaaggaaaccaagt
```

The following primer and extension product sequences are shown in a 5' to 3' orientation. The following nucleic acid primer and nucleotides are added to the extension reaction:

```
Nucleic Acid Primer (Q1):  agagaaagaggcagaaaaaa              (SEQ ID NO:28)

Nucleotides:   1.  Unlabeled dideoxycytosine triphosphate (ddCTP) ("c")
               2.  Unlabeled deoxyadenosine triphosphate (dATP) ("a")
               3.  Unlabeled deoxyguanosine triphosphate (dGTP) ("g")
               4.  Labeled deoxythymidine triphosphate (dTTP) ("t*")
```

The following extension products are obtained for wild type (wt) and mutant (mt) templates:

```
wt-agagaaagaggcagaaaaaac           (SEQ ID NO:29)
mt-agagaaagaggcagaaaaaaat*t*gat*t*c (SEQ ID NO:30)
```

Example 5

Mutation Detection at APC

Other variants or mutants are detected at the APC locus by interrogating amplicons generated by amplification using forward (For) and reverse (Rev) primers and the amplicons are captured by hybridization (Amplicon B is 188 bp long and is generated using B-For tgtagttcattatcatcttt (SEQ ID NO: 31) and B-Rev cttcgcacacaggatcttca (SEQ ID NO: 32), Amplicon C is 185 bp long and is generated using C-For aggcacaaagct-gttgaat (SEQ ID NO: 33) and C-Rev tatcaagtgaactgacaga (SEQ ID NO: 34), Amplicon D is 188 bp long and is generated using D-For cacctccaccacctcctcaa (SEQ ID NO: 35) and D-Rev gtatcagcatctg (SEQ ID NO: 36)).

Variants can be detected in the following reactions using the following primers and nucleotides. The variants are detected as the presence of the following mutant (mt) extension products:

```
Reaction I:
Nucleic Acid Primer  (B1):       aaatagcagaaataaaa (B1)                                  (SEQ ID NO:37)

Nucleotides:            1.   Unlabeled deoxyguanosine triphosphate (dGTP) ("g")
                        2.   Unlabeled deoxyadenosine triphosphate (dATP) ("a")
                        3.   Labeled dideoxythymidine triphosphate (ddTTP) ("t*")

Extension Products:
                             wt-aaataagcagaaataaaaggaaagat*                              (SEQ ID NO:38)

mt-aaatagcagaaataaaagat*                                    (SEQ ID NO:39)

Reaction II:
Nucleic Acid Primer  (B3):       tccaatcttttcttttattt                                    (SEQ ID NO:40)

Option 1:
Nucleotides:            1.   Unlabeled deoxycytosine triphosphate (dCTP) ("c")
                        2.   Labeled dideoxyadenosine triphosphate (ddATP) ("a*")

Extension Products:
                             wt-tccaatcttttcttttatttc                                    (SEQ ID NO:41)

mt1-tccaatcttttcttttattta*                                  (SEQ ID NO:42)

Option 2:
Nucleotides:            1.   Unlabeled deoxycytosine triphosphate (dCTP) ("c")
                        2.   Labeled dideoxyguanosine triphosphate (ddGTP) ("g*")

Extension Products:
                             wt-tccaatcttttcttttatttc                                    (SEQ ID NO:43)

mt2-tccaatcttttcttttatttg*                                  (SEQ ID NO:44)

Option 3
Nucleotides:            1.   Unlabeled deoxycytosine triphosphate (dCTP) ("c")
                        2.   Labeled dideoxythymidine triphosphate (ddTTP) ("t*")

Extension Products:
                             wt-tccaatcttttcttttatttct                                   (SEQ ID NO:45)

mt-tccaatcttttcttttatttt                                    (SEQ ID NO:46)

Reaction III:
Nucleic Acid Primer  (B4):       atcttcagctgactagttc                                     (SEQ ID NO:47)

Nucleotides:            1.   Unlabeled dideoxycytosine triphosphate (ddCTP) ("c")
                        2.   Unlabeled deoxyadenosine triphosphate (dATP) ("a")
                        3.   Labeled deoxythymidine triphosphate (dTTP) ("t*")

Extension Products:
                             wt-atcttcagctgactagttcc                                     (SEQ ID NO:48)

mt-atcttcagctgactagttcat*t*t*at*t*t*c                       (SEQ ID NO:49)

Reaction IV:
Nucleic Acid Primer  (C1):       ctccctcaaaagtggtgct                                     (SEQ ID NO:50)

Nucleotides:            1.   Unlabeled dideoxycytosine triphosphate (ddCTP) ("c")
                        2.   Unlabeled deoxythymidine triphosphate (dTTP) ("t")
                        3.   Labeled deoxyadenosine triphosphate (dATP) ("a*")

Extension Products:
                             wt-ctccctcaaaagtggtgctc                                     (SEQ ID NO:51)

mt-ctccctcaaaagtggtgctta*                                   (SEQ ID NO:52)

Reaction V:
Nucleic Acid Primer  (c2):       gtccacctgaacactatgtt                                    (SEQ ID NO:53)

Nucleotides:            1.   Unlabeled dideoxycytosine triphosphate (ddCTP) ("c")
                        2.   Unlabeled deoxythymidine triphosphate (dTTP) ("t")
                        3.   Labeled deoxyadenosine triphosphate (dATP) ("a*")

Extension Products:
                             wt-gtccacctgaacactatgttc                                    (SEQ TD NO:54)

mt-gtccacctgaacactatgtttta*                                 (SEQ ID NO:55)

Reaction VI:
Nucleic Acid Primer  (c3):       gctaaacatgagtggggt                                      (SEQ ID NO:56)
```

```
Nucleotides:        1.   Unlabeled dideoxycytosine triphosphate (ddCTP) ("c")
                    2.   Unlabeled deoxyadenosine triphosphate (dATP) ("a")
                    3.   Labeled deoxythymidine triphosphate (dTTP) ("t*")

Extension Products:
                         wt-gctaaacatgagtggggtc                               (SEQ ID NO:57)

mt-gctaaacatgagtggggtat*c                            (SEQ ID NO:58)

Reaction VII:
Nucleic Acid Primer (D1):  ctcaaacagctcaaaccaag                               (SEQ ID NO:59)

Nucleotides:        1.   Unlabeled dideoxycytosine triphosphate (ddCTP) ("c")
                    2.   Unlabeled deoxythymidine triphosphate (dTTP) ("t")
                    3.   Labeled deoxyguanosine triphosphate (dGTP) ("g*")

Extension Products:
                         wt-ctcaaacagctcaaaccaagc                             (SEQ ID NO:60)

mt-ctcaaacagctcaaaccaagtg*                           (SEQ lID NO:61)

Reaction VIII:
Nucleic Acid Primer (D3):  tgcttaggtccactttctct                               (SEQ ID NO:62)

Nucleotides:        1.   Labeled dideoxycytosine triphosphate (ddCTP) ("c*")
                    2.   Unlabeled deoxythyrnidine triphosphate (dTTP) ("t")

Extension Products:
                         wt-tgcttaggtccactttctctc*                            (SEQ ID NO:63)

mt-tgcttaggtccactttctcttttttc*                       (SEQ ID NO:64)
```

Example 6

Variation Detection at Kras Cp2

Variants are detected at the HUMRASK02 (exon1) by interrogating amplicons generated by amplification using forward (For) and reverse (Rev) primers and the amplicons are captured by hybridization (Amplicon A is 242 bp long and is generated using A-For cctgctgaaaatgactgaa (SEQ ID NO: 65) and A-Rev tatgaaaatggtcagagaaa (SEQ ID NO: 66)).

Variants can be detected in the following reactions using the following primers and nucleotides. The variants are detected as the presence of the following mutant (mt) extension products:

```
Reaction I:
Nucleic Acid Primer (A1):   aacttgtggtagttggagct                              (SEQ ID NO:67)

Option 1:
Nucleotides:        1.   Unlabeled deoxyguanosine triphosphate (dGTP) ("g")
                    2.   Labeled dideoxyadenosine triphosphate (ddATP) ("a*")

Extension Products:
                         wt-aacttgtggtagttggagctgg                            (SEQ ID NO:68)

mt1-aacttgtggtagttggagcta*                           (SEQ ID NO:69)

Option 2.
Nucleotides:        1.   Unlabeled deoxyguanosine triphosphate (dGTP) ("g")
                    2.   Labeled dideoxycytosine triphosphate (ddCTP) ("c*")

Extension Products:
                         wt-aacttgtggtagttggagctgg                            (SEQ ID NO:70)

mt2-aacttgtggtagttggagctc*                           (SEQ ID NO:71)

Option 3:
Nucleotides:        1.   Unlabeled deoxyguanosine triphosphate (dGTP) ("g")
                    2.   Labeled dideoxythymidine triphosphate (ddTTP) ("t*")

Extension Products:
                         wt-aacttgtggtagttggagctggt*                          (SEQ ID NO:72)

mt-aacttgtggtagttggagctt*                            (SEQ ID NO:73)

Reaction II:
Nucleic Acid Primer (A2 rev):  ggcactttgcctacgcca                             (SEQ ID NO:74)
```

-continued

```
Option 1.
Nucleotides:       1.      Unlabeled deoxycytosine triphosphate (dCTP) ("c")
                   2.      Labeled dideoxythymidine triphosphate (ddTTP) ("t*")

Extension Products:
                           wt-ggcactttgcctacgccacc                                    (SEQ ID NO:75)

mt1-ggcactttgcctacgccat*                                   (SEQ ID NO:76)

Option 2:
Nucleotides:       1.      Unlabeled deoxycytosine triphosphate (dCTP) ("c")
                   2.      Labeled dideoxyguanosine triphosphate (ddGTP) ("g*")

Extension Products:
                           wt-ggcactttgcctacgccacc                                    (SEQ ID NO:77)

mt2-ggcactttgcctacgccag*                                   (SEQ ID NO:78)

Option 3:
Nucleotides:       1.      Unlabeled deoxycytosine triphosphate (dCTP) ("c")
                   2.      Labeled dideoxyadenosine triphosphate (ddATP) ("a*")

Extension Products:
                           wt-acttgtggtagttggagctgcca*                                (SEQ ID NO:79)

mt-acttgtggtagttggagctga*                                  (SEQ ID NO:80)

Reaction III:
Nucleic Acid Primer  (A3 rev):   aaggcactttgcctacg                                   (SEQ ID NO:81)

Option 1:
Nucleotides:       1.      Unlabeled deoxycytosine triphosphate (dCTP) ("c")
                   2.      Labeled dideoxyguanosine triphosphate (ddGTP) ("g*")

Extension Products:
                           wt-aaggcactttgcctacgcc                                     (SEQ ID NO:82)

mt1-gaaggcactttgcctacgg*                                   (SEQ ID NO:83)

Option 2:
Nucleotides:       1.      Unlabeled deoxycytosine triphosphate (dCTP) ("c")
                   2.      Labeled dideoxythymidine triphosphate (ddTTP) ("t*")

Extension Products:
                           wt-aaggcactttgcctacgcc                                     (SEQ ID NO:84)

mt2-gaaggcactttgcctacgt*                                   (SEQ ID NO:85)

Option 3:
Nucleotides:       1.      Unlabeled deoxycytosine triphosphate (dCTP) ("c")
                   2.      Labeled dideoxyadenosine triphosphate (ddATP) ("a*")

Extension Products:
                           wt-ggggcactttgcctacgcca*                                   (SEQ ID NO:86)

wt-aaggcactttgcctacga*                                     (SEQ ID NO:87)
```

Example 7

Variation Detection at p53 (HSP53)

Variants or mutants at the p53 locus are detected by interrogating amplicons generated by amplification using forward (For) and reverse (Rev) primers and the amplicons are captured by hybridization (Amplicon E is 203 bp long and is generated using E-For ccatctacaagcagtc (SEQ ID NO: 88) and E-Rev cagacctaagagcaatca (SEQ ID NO: 89), Amplicon F is 229 bp long and is generated using F-For taccaccatccactacaa (SEQ ID NO: 90) and F-Rev taccttctttagccatt (SEQ ID NO: 91), Amplicon G is 226 bp long and is generated using G-For ctgcctcttgcttctctttt (SEQ ID NO: 92) and G-Rev tgcttgcttacct (SEQ ID NO: 93)).

Variants can be detected in the following reactions using the following primers and nucleotides. The variants are detected as the presence of the following mutant (mt) extension products:

Reaction I:
Nucleic Acid Primer (E1):       catgacggaggttgtgaggc                                            (SEQ ID NO:94)

An A or T mutation is detected.
Nucleotides:    1.      Unlabeled dideoxyguanosine triphosphate (ddGTP) ("g")
                2.      Unlabeled deoxyadenosine triphosphate (dATP) ("a")
                3.      Unlabeled deoxythymidine triphosphate (dTTP) ("t")
                4.      Labeled deoxycytosine triphosphate (dCTP) ("c*")

Extension Products:
                wt-catgacggaggttgtgaggcg                                                        (SEQ ID NO:95)

mt-ggtgacggaggttgtgaggcac*tg                                                    (SEQ ID NO:96)

mt-catgacggaggttgtgaggctc*tg                                                    (SEQ ID NO:97)

Reaction II:
Nucleic Acid Primer (F1 rev):   ggatgggcctcggttcatgc                                            (SEQ ID NO:98)

Nucleotides:    1.      Unlabeled dideoxycytosine triphosphate (ddCTP) ("c")
                2.      Unlabeled deoxythymidine triphosphate (dTTP) ("t")
                3.      Unlabeled deoxyadenosine triphosphate (dATP) ("a")
                4.      Labeled deoxyguanosine triphosphate (dGTP) ("g*")

Extension Products:
                wt-ggatgggcctcggttcatgcc                                                        (SEQ ID NO:99)

mt1-ggatgggcctcggttcatgcag*c                                                    (SEQ ID NO:100)

mt2-ggatgggcctcggttcatgctg*c                                                    (SEQ ID NO:101)

Reaction III:
Nucleic Acid Primer (F2):       gtaacagttcctgcatgggcg                                           (SEQ ID NO:102)

Nucleotides:    1.      Unlabeled dideoxyguanosine triphosphate (ddGTP) ("g")
                2.      Unlabeled deoxyadenosine triphosphate (dATP) ("a")
                3.      Unlabeled deoxythymidine triphosphate (dTTP) ("t")
                4.      Labeled deoxycytosine triphosphate (dCTP) ("c*")

Extension Products:
                wt-gtaacagttcctgcatgggcgg                                                       (SEQ ID NO:103)

mt-gtaacagttcctgcatgggcgac*atg                                                  (SEQ ID NO:104)

mt-gtaacagttcctgcatgggcgtc*atg                                                  (SEQ ID NO:105)

Reaction IV:
Nucleic Acid Primer (F3):       cctgcatgggcggcatgaac                                            (SEQ ID NO:106)

Nucleotides:    1.      Unlabeled dideoxycytosine triphosphate (ddCTP) ("c")
                2.      Unlabeled deoxythymidine triphosphate (dTTP) ("t")
                3.      Labeled deoxyguanosine triphosphate (dGTP) ("g*")

Extension Products:
                wt-cctgcatgggcggcatgaacc                                                        (SEQ ID NO:107)

mt-cctgcatgggcggcatgaactg*g*                                                    (SEQ ID NO:108)

Reaction V:
Nucleic Acid Primer (F4 rev):   gatggtgaggatgggcctc                                             (SEQ ID NO:109)

Nucleotides:    1.      Unlabeled dideoxycytosine triphosphate (ddCTP) ("c")
                2.      Unlabeled deoxythymidine triphosphate (dTTP) ("t")
                3.      Labeled deoxyguanosine triphosphate (dGTP) ("g*")

Extension Products:
                wt-gatggtgaggatgggcctcc                                                         (SEQ ID NO:110)

mt-gatggtgaggatgggcctctg*g*ttc                                                  (SEQ ID NO:111)

Reaction VI:
Nucleic Acid Primer (G1):       gacggaacagctttgagg                                              (SEQ ID NO:112)

Nucleotides:    1.      Unlabeled dideoxycytosine triphosphate (ddCTP) ("c")
                2.      Unlabeled deoxyadenosine triphosphate (dATP) ("a")
                3.      Unlabeled deoxythymidine triphosphate (dTTP) ("t")
                4.      Labeled deoxyguanosine triphosphate (dGTP) ("g*")

```
                                       -continued
Extension Products:
                         wt-gacggaacagctttgaggc                                (SEQ ID NO:113)

mt-gacggaacagctttgaggag*c                             (SEQ ID NO:114)

mt-gacggaacagctttgaggtg*c                             (SEQ ID NO:115)

Reaction VII:
Nucleic Acid Primer (G2): acggaacagctttgaggtgc                                 (SEQ ID NO:116)

Nucleotides:       1.    Unlabeled dideoxyguanosine triphosphate (ddGTP) ("g")
                   2.    Unlabeled deoxyadenosine triphosphate (dATP) ("a")
                   3.    Labeled deoxythymidine triphosphate (dTTP) ("1*")

Extension Products:
                         wt-acggaacagctttgaggtgcg                              (SEQ ID NO:117)

mt-acggaacagctttgaggtgcat*g                           (SEQ ID NO:118)

Reaction VIII:
Nucleic Acid Primer (G3): gtgcctgtcctgggagagac                                 (SEQ ID NO:119)

Nucleotides:       1.    Unlabeled dideoxycytosine triphosphate (ddCTP) ("c")
                   2.    Unlabeled deoxythymidine triphosphate (dTTP) ("t")
                   3.    Labeled deoxyguanosine triphosphate (dGTP) ("g*")

Extension Products:
                         wt-gtgcctgtcctgggagagacc                              (SEQ ID NO:120)

wt-gtgcctgtcctgggagagactg*g*c                         (SEQ ID NO:121)
```

Example 8

Mutations Detected in Various Sites on a Target Gene

Table 2 identifies certain mutations that are detected for various sequences that are specific to a particular site on a gene. In addition, the chart identifies the type of mutation that is associated with the mutant sequence. These sequences that have been identified are used according to the methods of the invention to detect and diagnose disease, such as colorectal cancer, in a non-invasive procedure.

TABLE 2

| Gene | Site | Mutation Type | Sequence (5' to 3') | SEQ ID NO: | Mutations Detected |
|---|---|---|---|---|---|
| k-ras | K12p1 | Point Mutation | Aacttgtggtagttggagct | 122 | G to A, C, or T |
| k-ras | K12p2 | Point Mutation | Acttgtggtagttggagctg | 123 | G to A, C, or T |
| k-ras | K13p2 | Point Mutation | Tgtggtagttggagctggtg | 124 | G to A, C, or T |
| APC | 1309 | Deletion | Aaatagcagaaataaaa | 125 | 2-5 bp Deletions |
| APC | 1306 | Point Mutation | Tccaatcttttcttttattt | 126 | G to A, C, or T |
| APC | 1312 | Point Mutation | Atcttcagctgacctagttc | 127 | G to T |
| APC | 1367 | Point Mutation | Ctccctccaaaagtggtgct | 128 | C to T |
| APC | 1378 | Point Mutation | Gtccacctgtacactatgtt | 129 | C to T |
| APC | 1379 | Point Mutation | Cctaaacataagtggggtct | 130 | G to T |
| APC | 1450 | Point Mutation | Ctcaaacagcacaaaccaag | 131 | C to T |
| APC | 1465 | Point Mutation (Deletion) | Tgcttaggcccactttctct | 132 | G to A |
| P53 | 175p2 | Point Mutation | Catgacggaggttgtgaggc | 133 | G to A or T |
| P53 | 245p1 | Point Mutation | Gtaacagttcctgcatgggc | 134 | G to A or T |
| P53 | 245p2 | Point Mutation | Taacagttcctgcatgggcg | 135 | G to A or T |
| P53 | 248p1 | Point Mutation | Cctgcatgggcggcatgaac | 136 | C to T |
| P53 | 248p2 | Point Mutation | Ctgcatgggcggcatgaacc | 137 | G to A |

TABLE 2-continued

| Gene | Site | Mutation Type | Sequence (5' to 3') | SEQ ID NO: | Mutations Detected |
|---|---|---|---|---|---|
| P53 | 273p1 | Point Mutation | Gacggaacagctttgaggtg | 138 | C to T |
| P53 | 273p2 | Point Mutation | Acggaacagctttgaggtgc | 139 | G to A |
| P53 | 282 | Point Mutation | Gtgcctatcctgggagagac | 140 | C to T |
| Bat26 | Bat26 | Deletion | Gcccttaaccttttcaggt | 141 | 4-15 bp Deletion |
| APC | 876 | Point Mutation | Ggtggagatctgcaaacctc | 142 | C to T |
| APC | 1554 | Point Mutation | agagaaagaggcagaaaaaa | 143 | C to A |

Example 9

Primer Sequences for DNA Integrity Analysis

Table 3 identifies particular DNA integrity assay primer sequences, along with a label (if any). Also provided are the lengths of these primer sequences. Furthermore, as the Oligo Name Bases having a "XXX-D-XXX" designation refers to those DNA integrity primer sequences related to APC. Also, the Oligo Name Bases having a "XXX-E-XXX" designation refers to those DNA integrity primer sequences related to p53. Furthermore, Table 3 shows useful capture sequences, along with a label that are used according to the methods of the invention.

The CAP-D designation refers to APC, and the CAP-E designation refers to p53. Also, the Oligo Name Bases also refers to the expected band sizes for the associated DIA primer sequence. For example, the labeled primer sequence having the "1.3-D-REV" Oligo Name Base designation may expect the detection of a nucleic acid fragment having a length of 1.3 Kb. The capture probe sequences that are used according to the methods of the invention are shown in Table 1 above. Certain of the capture probe sequences may be cross-references to various capture probes provided in the Examples herein.

In general, capture probes are preferably biotinylated so that they can be purified (along with the capture nucleic acids) using, for example, steptavidin coated beads according to the

TABLE 3

| Oligo Name Bases | Sequence 5'-3' | Label | SEQ ID NO: |
|---|---|---|---|
| PCR-D-FOR | gcggtcccaaaagggtcagtcacctccaccacctcctcaa | N/A | 144 |
| 200-D-REV | gcggtcccaaaagggtcagtgtatcagcatctggaagaa | 5'-Biotin | 145 |
| 400-D-REV | gcggtcccaaaaggtcagtcatcatcatctgaatcatct | 5'-Biotin | 146 |
| 800-D-REV | gcggtcccataagggtcagttcacctgactgtgctcctcc | 5'-Biotin | 147 |
| 1.3-D-REV | gcggtccctaaagggtcagtttggctgctttgcaatagctt | 5'-Biotin | 148 |
| 1.8-D-REV | gcggtcccataagggtcagtttggcattgcggagcttatac | 5'-Biotin | 149 |
| 2.4-D-REV | gcggtcccaaaagggtcagtggcttaattctgatttcaca | 5'-Biotin | 150 |
| PCR-E-FOR | gcggtcccaaaagggtcagtccatctacaagcagtca | N/A | 151 |
| PCR-E-FOR | gcggtcccaaaagggtcagtcagacctaagagcaatca | 5'-Biotin | 152 |
| 400-E-REV | gcggtcccaaaagggtcagtcccatttactttgcacatct | 5'-Biotin | 153 |
| 800-E-REV | gcggtcccaaaagggtcagtcccatgcaggaactgtt | 5'-Biotin | 154 |
| 1.3-E-REV | gcggtcccaaaagggtcagagtatggaagaaateggtaa (same sequence as PCR-F-REV) | 5'-Biotin | 155 |
| 1.8-E-REV | gcggtcccaaaagggtcagtagcatctgtatcaggcaaag | 5'-Biotin | 156 |
| 2.4-E-REV | gcggtccgaaaagggtcagtgggcaacagagcaagatg | 5'-Biotin | 157 |
| Capture Sequences | | | |
| CAP-E | cagatagccctggacaaaccatgccaccaagcagaag | 5'-Biotin | 158 |
| CAP-E | tactcccctgccctcaacaagatgttttgccaactgg | 5'-Biotin | 159 | methods known in the art. Also, sequences may be purified and detected according to other methods commonly known to those skilled in the art.

Example 10

Internal Control Samples for Primer Extension Reactions

As illustrated in Table 4, mutant, wild-type and internal controls with a one base difference at the mutation site and a different labeled acyclo nucleotide were used to distinguish mutant from internal control samples.

TABLE 4

Site: A1

| Sequence type | Sequence with different labeled acyclo nucleotide | SEQ ID NO: |
|---|---|---|
| Mutant | AacttgtggtagttggagctT | 160 |
| Wildtype | AacttgtggtagttggagctG | 161 |
| Internal control | AacttgtggtagttggagctC | 162 |

R110 acyclo-TTP, Tamra acyclo-CTP and unlabeled ddGTP were used in the reaction cocktail. Samples were generated with oligo controls by making 2%, 1% mutant and 100% wildtype and all samples were mixed with 1% of the internal control. Four reaction conditions were tested using two different dilutions (1:20 and 1:100, Table 5, T is the mutant nucleotide and C is the control nucleotide) of the labeled nucleotides to see how this influences variability. The results of these reactions are shown in FIG. 1.

TABLE 5

| | |
|---|---|
| T1_20 | C1_20 |
| T1_20 | C1_100 |
| T1_100 | C1_20 |
| T1_100 | C1_100 |

Figure 2:
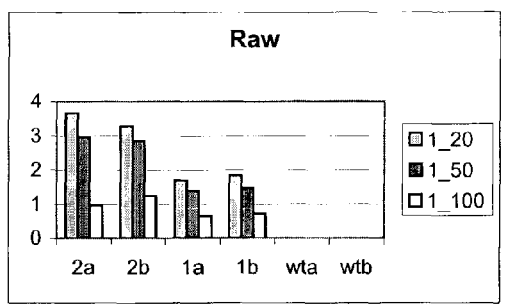
FIG. 2 shows four charts that illustrate use of the same labeled terminator for the internal control and the sample sequence.
Figure 2:
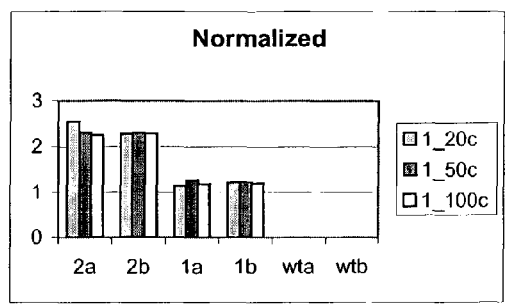
Figure 2:
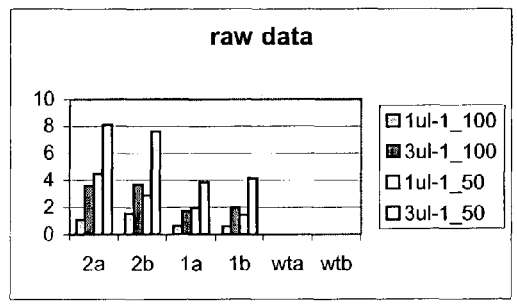
Figure 2:
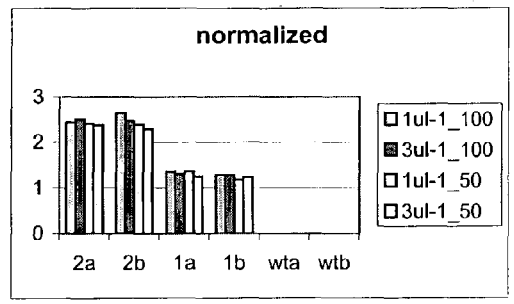

Using the same labeled terminator for the internal control and sample eliminates variability of replicates as well as sample to control ratios for different terminator lots, as illustrated in FIG. 2. Using the same lot of labeled nucleotide for the internal control and sample will correct for lot fluctuations, and it is therefore a valid method to use absolute ratios (sample-to-control) in the determination of whether a sample is positive or negative.

Example 11

Single Base Extension Mutant Detection Reactions

The following primers are used in single base extension reactions to detect mutations at the loci described in Examples 1-10 above. The nucleotide used for blocking each extension reaction is preferably a terminator nucleotide such as a ddNTP or an acyclo terminator. The labeled nucleotide that is incorporated in the presence of a mutation also is preferably a terminator nucleotide such as a labeled ddNTP or an acyclo terminator Preferably the extension reaction is repeated several times by cycling the reaction between extension and denaturing temperatures for 5 to 50 cycles, more preferably for 10 to 40 cycles, and more preferably for about 20 to 30 cycles.

TABLE 6

| SBE primer | Sequence | SEQ. ID NO: |
|---|---|---|
| (A1 SBE) | Aacttgtggtagttggagct | 163 |
| (A2 SBE) | Acttgtggtagttggagctg | 164 |
| (A3 SBE) | Tgtggtagttggagctggtg | 165 |
| (B1 SBE) | Aaatagcagaaataaaa | 166 |
| (B1 SBE) | Aaatagcagaaataaaa | 167 |
| (B3 SBE) | Tccaatcttttcttttattt | 168 |
| (B4 SBE) | Atcttcagctgacctagttc | 169 |
| (C1 SBE) | Ctccctccaaaagtggtgct | 170 |
| (C2 SBE) | Gtccacctgtacactatgtt | 171 |
| (C3 SBE) | Gctaaacataagtggggtct | 172 |
| (D1 SBE) | Ctcaaacagcacaaaccaag | 173 |
| (D3 SBE) | Tgcttaggcccactttctct | 174 |
| (E1 SBE) | Catgacggaggttgtgaggc | 175 |
| (F1 SBE) | Gtaacagttcctgcatgggc | 176 |
| (F2 SBE) | Taacagttcctgcatgggcg | 177 |
| (F3 SBE) | Cctgcatgggcggcatgaac | 178 |
| (F4 SBE) | Ctgcatgggcggcatgaacc | 179 |
| (G1 SBE) | Gacggaacagctttgaggtg | 180 |
| (G2 SBE) | Acggaacagctttgaggtgc | 181 |
| (G3 SBE) | Gtgcctatcctgggagagac | 182 |
| (P1 SBE) | Ggtggagatctgcaaacctc | 183 |
| (Q1 SBE) | Agagaaagaggcagaaaaaa | 184 |
| (J1 BAT-26) | Gcccttaaccttttcaggt | 185 |

The following reaction conditions were used for the different single base extension primers (SBE primers) shown in Table 6:

Reaction I: Nucleic Acid SBE Primers A1, A2 and A3 (Kras Cp2)

Three separate 5 µl reactions were run for each primer, each reaction including 5 µM primer, 10× reaction buffer, Acyclopol polymerase, and water as described above. Each reaction also included the following nucleotides:

Nucleotides:

1. 50 µM Unlabeled terminator (dd or acyclo GTP)
2. Labeled terminator (R110-dd or R110-acylco ATP)
3. Labeled terminator (R110-dd or R110-acylco CTP)
4. Labeled terminator (R110-dd or R110-acylco TTP)

Reaction II: Nucleic Acid Primer B1 (APC 1309)

A 5 µl extension reaction included 5 µM primer, 10× reaction buffer, 0.025 µL Acyclopol (32 U/µL), 0.15 µl Thermosequenase, 1.775 µL water. Each reaction also included the following nucleotides:

Nucleotides:

1. 2 mM Unlabeled deoxyadenosine triphosphate/deoxyguanosine triphosphate (dATP/dGTP)

2. Labeled terminator (R110-dd or R110-acylco TTP)

Reaction III: Nucleic Acid SBE Primer B3 (APC 1306)

A 5 µl extension reaction included 5 µM primer, 10× reaction buffer, 0.025 µL Acyclopol (32 U/µL), 1.825 µL water. Each reaction also included the following nucleotides:

Nucleotides:
1. 50 µM Unlabeled terminator (dd or acyclo CTP)
2. Labeled terminator (R110-dd or R110-acylco ATP)
3. Labeled terminator (R110-dd or R110-acylco GTP)
4. Labeled terminator (R110-dd or R110-acylco TTP)

Reaction IV: Nucleic Acid SBE Primer B4 (APC 1312)

A 5 µl extension reaction included 5 µM primer, 10× reaction buffer, 0.025 µL Acyclopol (32 U/µL), 0.925 µL water. Each reaction also included the following nucleotides:

Nucleotides:
1. 50 µM Unlabeled terminator (dd or acyclo CTP)
2. 50 µM Unlabeled terminator (dd or acyclo TTP)
3. Labeled terminator (R110-dd or R110-acylco ATP)

Reaction V: Nucleic Acid SBE Primers C1 and C2 (APC)

Two separate reactions were run for each primer, each reaction including 5 µM primer, 10× reaction buffer, 0.025 µL Acyclopol (32 U/µL), and water. Each reaction also included the following nucleotides:

Nucleotides:
1. 50 µM Unlabeled terminator (dd or acyclo ATP)
2. 50 µM Unlabeled terminator (dd or acyclo CTP)
3. 50 µM Unlabeled terminator (dd or acyclo GTP)
4. Labeled terminator (R110-dd or R110-acylco TTP)

Reaction VI: Nucleic Acid SBE Primer C3 (APC)

A 5 µl extension reaction included 5 µM primer, 10× reaction buffer, 0.025 µL Acyclopol (32 U/µL), 1.925 µL water. Each reaction also included the following nucleotides:

Nucleotides:
1. 50 µM Unlabeled terminator (dd or acyclo CTP)
2. Labeled terminator (R110-dd or R110-acylco ATP)

Reaction VII: Nucleic Acid SBE Primers D1 and D3 (APC)

Two separate reactions were run for each primer, each reaction including 5 µM primer, 10× reaction buffer, 0.025 µL Acyclopol (32 U/µL), 1.825 µL water. Each reaction also included the following nucleotides:

Nucleotides:
1. 50 µM Unlabeled terminator (dd or acyclo ATP)
2. 50 µM Unlabeled terminator (dd or acyclo CTP)
3. 50 µM Unlabeled terminator (dd or acyclo GTP)
4. Labeled terminator (R110-dd or R110-acylco TTP)

Reaction VIII: Nucleic Acid SBE Primer E1, F1 and F2 (p53)

Three separate reactions were run, each of which including 5 µM primer, 10× reaction buffer, 0.025 µL Acyclopol (32 U/µL), and 0.875 µL water. Each reaction also included the following nucleotides:

Nucleotides:
1. 50 µM terminator (dd or acyclo CTP)
2. 50 µM terminator (dd or acyclo GTP)
3. Labeled terminator (R110-dd or R110-acylco ATP)
4. Labeled terminator (R110-dd or R110-acylco TTP)

Reaction IX: Nucleic Acid SBE Primer F3 (p53)

A 5 µl extension reaction included 5 µM primer, 10× reaction buffer, 0.025 µL Acyclopol (32 U/µL), and water. Each reaction also included the following nucleotides:

Nucleotides:
1. 50 µM Unlabeled terminator (dd or acyclo ATP)
2. 50 µM Unlabeled terminator (dd or acyclo CTP)
3. 50 µM Unlabeled terminator (dd or acyclo GTP)
4. Labeled terminator (R110-dd or R110-acylco TTP)

Reaction X: Nucleic Acid SBE Primer F4 (p53)

A 5 µl extension reaction included 5 µM primer, 10× reaction buffer, 0.025 µL Acyclopol (32 U/µL), and water. Each reaction also included the following nucleotides:

Nucleotides:
1. 50 µM Unlabeled terminator (dd or acyclo CTP)
2. 50 µM Unlabeled terminator (dd or acyclo GTP)
3. 50 µM Unlabeled terminator (dd or acyclo TTP)
4. Labeled terminator (R110-dd or R110-acylco ATP)

Reaction XI: Nucleic Acid SBE Primer G1 (p53)

A 5 µl extension reaction included 5 µM primer, 10× reaction buffer, 0.025 µL Acyclopol (32 U/µL), and 0.875 µL water. Each reaction also included the following nucleotides:

Nucleotides:
1. 50 µM Unlabeled terminator (dd or acyclo CTP)
2. 50 µM Unlabeled terminator (dd or acyclo GTP)
3. Labeled dideoxyadenosine triphosphate (R110-ddATP)
4. Labeled terminator (R110-dd or R110-acylco TTP)

Reaction XII: Nucleic Acid SBE Primer G2 (p53)

A 5 µl extension reaction included 5 µM primer, 10× reaction buffer, 0.025 µL Acyclopol (32 U/µL), and 1.925 µL water. Each reaction also included the following nucleotides:

Nucleotides:
1. 50 µM Unlabeled terminator (dd or acyclo GTP)
2. Labeled terminator (R110-dd or R110-acylco ATP)

Reaction XIII: Nucleic Acid SBE Primer G3 (p 53)

A 5 µl extension reaction included 5 µM primer, 10× reaction buffer, 0.025 µL Acyclopol (32 U/µL), and 1.925 µL water. Each reaction also included the following nucleotides:

Nucleotide:
1. 50 µM Unlabeled terminator (dd or acyclo CTP)
2. Labeled terminator (R110-dd or R110-acylco TTP)

Reaction XIV: Nucleic Acid Primer J1 (BA T-26)

A 5 µl extension reaction included 5 µM primer, 10× reaction buffer, 0.025 µL Acyclopol (32 U/µL), 0.01 µL Thermo sequenase, and water. Each reaction also included the following nucleotides:

Nucleotides:
1. 2 mM Unlabeled deoxyadenosine triphosphate (dATP)
2. Labeled terminator (R110-dd or R110-acylco GTP)

Reaction XV: Nucleic Acid SBE Primers P1 and Q1 (APC)

A 5 µl extension reaction included 5 µM primer, 10× reaction buffer, 0.025 µL Acyclopol (32 U/µL), and water. Each reaction also included the following nucleotides:

Nucleotides:
1. 50 µM Unlabeled terminator (dd or acyclo CTP)
2. 50 µM Unlabeled terminator (dd or acyclo GTP)
3. 50 µM Unlabeled terminator (dd or acyclo TTP)
4. Labeled dideoxyadenosine triphosphate (R110-ddATP)

We claim:

1. A method for minimizing nucleotide misincorporation in a primer extension assay, the method comprising the steps of:
   a) providing a heterogeneous nucleic acid sample comprising a target nucleic acid containing a predetermined position suspected of containing a first variant base and a second variant base;
   b) contacting the heterogeneous nucleic acid sample with a primer complementary to a region adjacent to the predetermined position, a first nucleotide and a second nucleotide, wherein the first nucleotide is complementary to the first variant base and the second nucleotide is complementary to the second variant base and is a chain terminator;
   c) providing a first polymerase that preferentially incorporates said first nucleotide and a second polymerase that preferentially incorporates said second nucleotide;
   d) extending said primer in a primer extension reaction, wherein the first polymerase preferentially incorporates said first nucleotide into the extended primer on a template containing the first variant base at the predetermined position and the second polymerase preferentially incorporates said second nucleotide into the extended primer on a template containing the second variant base at the predetermined position, thereby reducing misincorporation of the first nucleotide into the extended primer on the template containing the second variant base.

2. The method of claim 1, wherein the second nucleotide is a dideoxynucleotide.

3. A method for detecting the presence of a variation at a predetermined position in a heterogeneous nucleic acid sample, the method comprising the steps of:
   a) contacting a heterogeneous nucleic acid sample with a primer substantially complementary to a region adjacent to the predetermined position suspected of containing a variant base, a first nucleotide complementary to the variant base, and a second nucleotide complementary to the wild-type base, wherein the first nucleotide is labeled with a detectable signal and the second nucleotide is a chain terminator,
   b) providing a first polymerase that preferentially incorporates said first nucleotide, and a second polymerase that preferentially incorporates said second nucleotide,
   c) performing a primer extension reaction to generate extended primers, and
   d) detecting the presence of the detectable signal in the extended primers, wherein the presence of the signal indicates the presence of the variation at the predetermined position.

4. The method of claim 3, wherein the detectable signal is a fluorescent signal.

5. The method of claim 3, further comprising adding to the primer extension reaction a terminator nucleotide complementary to a nucleotide downstream from said predetermined position.

6. The method of claim 3, wherein the variant base is present in less than 10% of nucleic acid molecules in the heterogeneous nucleic acid sample.

7. The method of claim 3, wherein the variant base is present in less than 1% of nucleic acid molecules in the heterogeneous nucleic acid sample.

8. The method of claim 3, wherein the heterogeneous nucleic acid sample comprises nucleic acids prepared from cells, tissue, or body fluid.

9. The method of claim 8, wherein the cells are selected from blood cells, colon cells, buccal cells, cervicovaginal cells, epithelial cells, fetal cells, and/or cells present in tissue obtained by biopsy.

10. The method of claim 8, wherein the body fluid is selected from blood, sputum, pancreatic fluid, bile, lymph, plasma, urine, cerebrospinal fluid, seminal fluid, saliva, breast nipple aspirate, pus, amniotic fluid and/or stool.

11. The method of claim 1, wherein the first nucleotide is labeled with a detectable signal.

12. The method of claim 1, wherein the first polymerase has between about 5% and a 100% preference for the first nucleotide relative to the second nucleotide.

13. The method of claim 1, wherein the second polymerase has between about 5% and a 100% preference for the second nucleotide relative to the first nucleotide.

* * * * *

SEQUENCE LISTING

<160> NUMBER OF SEQ IDS NOS: 185

<210> SEQ ID NO 1
<211> LENGTH: 37
<212> TYPE: DNA
<213> ORGANISM: Artificial Sequence
<220> FEATURE:
<223> OTHER INFORMATION: Primer sequence 1

<400> SEQUENCE: 1
gtggagtatt tgatagtgta ttaaccttat gtgtgac          37

<210> SEQ ID NO 2
<211> LENGTH: 37
<212> TYPE: DNA
<213> ORGANISM: Artificial Sequence
<220> FEATURE:
<223> OTHER INFORMATION: Primer sequence 2

<400> SEQUENCE: 2
ttccagcagt gtcacagcac cctagaacca aatccag          37

<210> SEQ ID NO 3
<211> LENGTH: 37
<212> TYPE: DNA
<213> ORGANISM: Artificial Sequence
<220> FEATURE:
<223> OTHER INFORMATION: Primer sequence 3

<400> SEQUENCE: 3
cagatagccc tggacaaacc atgccaccaa gcagaag          37

<210> SEQ ID NO 4
<211> LENGTH: 37
<212> TYPE: DNA
<213> ORGANISM: Artificial Sequence
<220> FEATURE:
<223> OTHER INFORMATION: Primer sequence 4

<400> SEQUENCE: 4
tactcccctg ccctcaacaa gatgttttgc caactgg          37

<210> SEQ ID NO 5
<211> LENGTH: 35
<212> TYPE: DNA
<213> ORGANISM: Artificial Sequence
<220> FEATURE:
<223> OTHER INFORMATION: Primer sequence 5

<400> SEQUENCE: 5
atttcttcca tactactacc catccacctc tcatc          35

<210> SEQ ID NO 6
<211> LENGTH: 37
<212> TYPE: DNA
<213> ORGANISM: Artificial Sequence
<220> FEATURE:
<223> OTHER INFORMATION: Primer sequence 6

<400> SEQUENCE: 6
atgaggccag tgcgccttgg ggagacctgt ggcaagc          37

<210> SEQ ID NO 7
<211> LENGTH: 37

<212> TYPE: DNA
<213> ORGANISM: Artificial Sequence
<220> FEATURE:
<223> OTHER INFORMATION: Primer sequence 7

<400> SEQUENCE: 7
gaaaggacaa gggtggttgg gagtagatgg agcctgg                              37

<210> SEQ ID NO 8
<211> LENGTH: 37
<212> TYPE: DNA
<213> ORGANISM: Artificial Sequence
<220> FEATURE:
<223> OTHER INFORMATION: Primer sequence 8

<400> SEQUENCE: 8
ttaagaattt aaaaatcgaa gatttctata ccactgg                              37

<210> SEQ ID NO 9
<211> LENGTH: 37
<212> TYPE: DNA
<213> ORGANISM: Artificial Sequence
<220> FEATURE:
<223> OTHER INFORMATION: Capture primer 9

<400> SEQUENCE: 9
acagatagtg aagaaggctt agaaaggagc taaaaga                              37

<210> SEQ ID NO 10
<211> LENGTH: 36
<212> TYPE: DNA
<213> ORGANISM: Artificial Sequence
<220> FEATURE:
<223> OTHER INFORMATION: Primer sequence 10

<400> SEQUENCE: 10
gaagttcctg gattttctgt tgctggatgg tagttg                               36

<210> SEQ ID NO 11
<211> LENGTH: 37
<212> TYPE: DNA
<213> ORGANISM: Artificial Sequence
<220> FEATURE:
<223> OTHER INFORMATION: Primer sequence 11

<400> SEQUENCE: 11
gattctgaag aaccaacttt gtccttaact agctctt                              37

<210> SEQ ID NO 12
<211> LENGTH: 37
<212> TYPE: DNA
<213> ORGANISM: Artificial Sequence
<220> FEATURE:
<223> OTHER INFORMATION: Primer sequence 12

<400> SEQUENCE: 12
ctaagtttga atccatgctt tgctcttctt gattatt                              37

<210> SEQ ID NO 13
<211> LENGTH: 37
<212> TYPE: DNA
<213> ORGANISM: Artificial Sequence
<220> FEATURE:
<223> OTHER INFORMATION: Capture primer 13

<400> SEQUENCE: 13

-continued

```
aagaggagct gggtaacact gtagtattca aatatgg                              37

<210> SEQ ID NO 14
<211> LENGTH: 37
<212> TYPE: DNA
<213> ORGANISM: Artificial Sequence
<220> FEATURE:
<223> OTHER INFORMATION: Primer sequence 14

<400> SEQUENCE: 14
gaatgtatta tttctgccat gccaacaaag tcatcac                              37

<210> SEQ ID NO 15
<211> LENGTH: 37
<212> TYPE: DNA
<213> ORGANISM: Artificial Sequence
<220> FEATURE:
<223> OTHER INFORMATION: Primer sequence 15

<400> SEQUENCE: 15
tcagaaggga gaaacacagt ctggattatt acagtgc                              37

<210> SEQ ID NO 16
<211> LENGTH: 37
<212> TYPE: DNA
<213> ORGANISM: Artificial Sequence
<220> FEATURE:
<223> OTHER INFORMATION: Primer sequence 16

<400> SEQUENCE: 16
aattatagtt tttatttttt gagtctttgc taatgcc                              37

<210> SEQ ID NO 17
<211> LENGTH: 37
<212> TYPE: DNA
<213> ORGANISM: Artificial Sequence
<220> FEATURE:
<223> OTHER INFORMATION: Primer sequence 17

<400> SEQUENCE: 17
catgtgctgt gactgcttgt agatggccat ggcgcgg                              37

<210> SEQ ID NO 18
<211> LENGTH: 37
<212> TYPE: DNA
<213> ORGANISM: Artificial Sequence
<220> FEATURE:
<223> OTHER INFORMATION: Primer sequence 18

<400> SEQUENCE: 18
gcaactgggg tctctgggag gaggggttaa gggtggt                              37

<210> SEQ ID NO 19
<211> LENGTH: 37
<212> TYPE: DNA
<213> ORGANISM: Artificial Sequence
<220> FEATURE:
<223> OTHER INFORMATION: Primer sequence 19

<400> SEQUENCE: 19
gaatgtatta tttctgccat gccaacaaag tcatcac                              37

<210> SEQ ID NO 20
<211> LENGTH: 37
<212> TYPE: DNA
<213> ORGANISM: Artificial Sequence
```

```
<220> FEATURE:
<223> OTHER INFORMATION: Primer sequence 20

<400> SEQUENCE: 20
cttctgcttg gtggcatggt ttgtccaggg ctatctg                              37

<210> SEQ ID NO 21
<211> LENGTH: 37
<212> TYPE: DNA
<213> ORGANISM: Artificial Sequence
<220> FEATURE:
<223> OTHER INFORMATION: Primer sequence 21

<400> SEQUENCE: 21
agaagtacat ctgctaaaca tgagtggggt ctcctga                              37

<210> SEQ ID NO 22
<211> LENGTH: 37
<212> TYPE: DNA
<213> ORGANISM: Artificial Sequence
<220> FEATURE:
<223> OTHER INFORMATION: Primer sequence 22

<400> SEQUENCE: 22
gcagttcaga gggtccaggt tcttccagat gctgata                              37

<210> SEQ ID NO 23
<211> LENGTH: 416
<212> TYPE: DNA
<213> ORGANISM: Artificial Sequence
<220> FEATURE:
<223> OTHER INFORMATION: APC nucleotide sequence

<400> SEQUENCE: 23
ggcaacatga ctgtcctttc accatatttg aatactacag tgttacccag ctcctcttca     60
tcaagaggaa gcttagatag ttctcgttct gaaaaagata gaagtttgga gagagaacgc    120
ggaattggtc taggcaacta ccatccagca acagaaaatc caggaacttc ttcaaaggga    180
ggtttgcaga tctccaccac tgcagcccag attgccaaag tcatggaaga agtgtcagcc    240
attcatacct ctcaggaaga cagaagttct gggtctacca ctgaattaca ttgtgtgaca    300
gatgagagaa atgcacttag aagaagctct gctgcccata cacattcaaa cacttacaat    360
ttcactaagt cggaaaattc aaataggaca tgttctatgc cttatgccaa attaga        416

<210> SEQ ID NO 24
<211> LENGTH: 20
<212> TYPE: DNA
<213> ORGANISM: Artificial Sequence
<220> FEATURE:
<223> OTHER INFORMATION: Primer sequence 24

<400> SEQUENCE: 24
atccaggaac ttcttcaaag                                                 20

<210> SEQ ID NO 25
<211> LENGTH: 23
<212> TYPE: DNA
<213> ORGANISM: Artificial Sequence
<220> FEATURE:
<223> OTHER INFORMATION: Primer sequence 25

<400> SEQUENCE: 25
atccaggaac ttcttcaaag gga                                             23
```

```
<210> SEQ ID NO 26
<211> LENGTH: 21
<212> TYPE: DNA
<213> ORGANISM: Artificial Sequence
<220> FEATURE:
<223> OTHER INFORMATION: Primer sequence 26

<400> SEQUENCE: 26
atccaggaac ttcttcaaag a                                              21

<210> SEQ ID NO 27
<211> LENGTH: 307
<212> TYPE: DNA
<213> ORGANISM: Artificial Sequence
<220> FEATURE:
<223> OTHER INFORMATION: APC nucleotide sequence

<400> SEQUENCE: 27
tctgagcctc gatgagccat ttatacagaa agatgtggaa ttaagaataa tgcctccagt      60
tcaggaaaat gacaatggga atgaaacaga atcagagcag cctaaagaat caaatgaaaa     120
ccaagagaaa gaggcagaaa aaactattga ttctgaaaag gacctattag atgattcaga     180
tgatgatgat attgaaatac tagaagaatg tattatttct gccatgccaa caaagtcatc     240
acgtaaaggc aaaaagccag cccagactgc ttcaaaatta cctccacctg tggcaaggaa     300
accaagt                                                               307

<210> SEQ ID NO 28
<211> LENGTH: 20
<212> TYPE: DNA
<213> ORGANISM: Artificial Sequence
<220> FEATURE:
<223> OTHER INFORMATION: Primer sequence 28

<400> SEQUENCE: 28
agagaaagag gcagaaaaaa                                                 20

<210> SEQ ID NO 29
<211> LENGTH: 21
<212> TYPE: DNA
<213> ORGANISM: Artificial Sequence
<220> FEATURE:
<223> OTHER INFORMATION: Primer sequence 29

<400> SEQUENCE: 29
agagaaagag gcagaaaaaa c                                              21

<210> SEQ ID NO 30
<211> LENGTH: 30
<212> TYPE: DNA
<213> ORGANISM: Artificial Sequence
<220> FEATURE:
<223> OTHER INFORMATION: Primer sequence 30

<400> SEQUENCE: 30
agagaaagag gcagaaaaaa atattgattc                                      30

<210> SEQ ID NO 31
<211> LENGTH: 20
<212> TYPE: DNA
<213> ORGANISM: Artificial Sequence
<220> FEATURE:
<223> OTHER INFORMATION: Primer sequence 31

<400> SEQUENCE: 31
```

```
tgtagttcat tatcatctttt                                              20

<210> SEQ ID NO 32
<211> LENGTH: 20
<212> TYPE: DNA
<213> ORGANISM: Artificial Sequence
<220> FEATURE:
<223> OTHER INFORMATION: Primer sequence 32

<400> SEQUENCE: 32
cttcgcacac aggatcttca                                               20

<210> SEQ ID NO 33
<211> LENGTH: 19
<212> TYPE: DNA
<213> ORGANISM: Artificial Sequence
<220> FEATURE:
<223> OTHER INFORMATION: Primer sequence 33

<400> SEQUENCE: 33
aggcacaaag ctgttgaat                                                19

<210> SEQ ID NO 34
<211> LENGTH: 19
<212> TYPE: DNA
<213> ORGANISM: Artificial Sequence
<220> FEATURE:
<223> OTHER INFORMATION: Primer sequence 34

<400> SEQUENCE: 34
tatcaagtga actgacaga                                                19

<210> SEQ ID NO 35
<211> LENGTH: 20
<212> TYPE: DNA
<213> ORGANISM: Artificial Sequence
<220> FEATURE:
<223> OTHER INFORMATION: Primer sequence 35

<400> SEQUENCE: 35
cacctccacc acctcctcaa                                               20

<210> SEQ ID NO 36
<211> LENGTH: 13
<212> TYPE: DNA
<213> ORGANISM: Artificial Sequence
<220> FEATURE:
<223> OTHER INFORMATION: Primer sequence 36

<400> SEQUENCE: 36
gtatcagcat ctg                                                      13

<210> SEQ ID NO 37
<211> LENGTH: 17
<212> TYPE: DNA
<213> ORGANISM: Artificial Sequence
<220> FEATURE:
<223> OTHER INFORMATION: Primer sequence 37

<400> SEQUENCE: 37
aaatagcaga aataaaa                                                  17

<210> SEQ ID NO 38
<211> LENGTH: 25
<212> TYPE: DNA
```

```
<213> ORGANISM: Artificial Sequence
<220> FEATURE:
<223> OTHER INFORMATION: Primer sequence 38

<400> SEQUENCE: 38
aaatagcaga aataaaagga aagat                                        25

<210> SEQ ID NO 39
<211> LENGTH: 20
<212> TYPE: DNA
<213> ORGANISM: Artificial Sequence
<220> FEATURE:
<223> OTHER INFORMATION: Primer sequence 39

<400> SEQUENCE: 39
aaatagcaga aataaaagat                                              20

<210> SEQ ID NO 40
<211> LENGTH: 20
<212> TYPE: DNA
<213> ORGANISM: Artificial Sequence
<220> FEATURE:
<223> OTHER INFORMATION: Primer sequence 40

<400> SEQUENCE: 40
tccaatcttt tcttttattt                                              20

<210> SEQ ID NO 41
<211> LENGTH: 21
<212> TYPE: DNA
<213> ORGANISM: Artificial Sequence
<220> FEATURE:
<223> OTHER INFORMATION: Primer sequence 41

<400> SEQUENCE: 41
tccaatcttt tcttttattt c                                            21

<210> SEQ ID NO 42
<211> LENGTH: 21
<212> TYPE: DNA
<213> ORGANISM: Artificial Sequence
<220> FEATURE:
<223> OTHER INFORMATION: Primer sequence 42

<400> SEQUENCE: 42
tccaatcttt tcttttattt a                                            21

<210> SEQ ID NO 43
<211> LENGTH: 21
<212> TYPE: DNA
<213> ORGANISM: Artificial Sequence
<220> FEATURE:
<223> OTHER INFORMATION: Primer sequence 43

<400> SEQUENCE: 43
tccaatcttt tcttttattt c                                            21

<210> SEQ ID NO 44
<211> LENGTH: 21
<212> TYPE: DNA
<213> ORGANISM: Artificial Sequence
<220> FEATURE:
<223> OTHER INFORMATION: Primer sequence 44

<400> SEQUENCE: 44
tccaatcttt tcttttattt g                                            21
```

<210> SEQ ID NO 45
<211> LENGTH: 22
<212> TYPE: DNA
<213> ORGANISM: Artificial Sequence
<220> FEATURE:
<223> OTHER INFORMATION: Primer sequence 45

<400> SEQUENCE: 45
tccaatcttt tcttttattt ct                                              22

<210> SEQ ID NO 46
<211> LENGTH: 21
<212> TYPE: DNA
<213> ORGANISM: Artificial Sequence
<220> FEATURE:
<223> OTHER INFORMATION: Primer sequence 46

<400> SEQUENCE: 46
tccaatcttt tcttttattt t                                               21

<210> SEQ ID NO 47
<211> LENGTH: 19
<212> TYPE: DNA
<213> ORGANISM: Artificial Sequence
<220> FEATURE:
<223> OTHER INFORMATION: Primer sequence 47

<400> SEQUENCE: 47
atcttcagct gactagttc                                                  19

<210> SEQ ID NO 48
<211> LENGTH: 20
<212> TYPE: DNA
<213> ORGANISM: Artificial Sequence
<220> FEATURE:
<223> OTHER INFORMATION: Primer sequence 48

<400> SEQUENCE: 48
atcttcagct gactagttcc                                                 20

<210> SEQ ID NO 49
<211> LENGTH: 29
<212> TYPE: DNA
<213> ORGANISM: Artificial Sequence
<220> FEATURE:
<223> OTHER INFORMATION: Primer sequence 49

<400> SEQUENCE: 49
atcttcagct gactagttca ttttatttc                                       29

<210> SEQ ID NO 50
<211> LENGTH: 19
<212> TYPE: DNA
<213> ORGANISM: Artificial Sequence
<220> FEATURE:
<223> OTHER INFORMATION: Primer sequence 50

<400> SEQUENCE: 50
ctccctcaaa agtggtgct                                                  19

<210> SEQ ID NO 51
<211> LENGTH: 20
<212> TYPE: DNA
<213> ORGANISM: Artificial Sequence
<220> FEATURE:

<223> OTHER INFORMATION: Primer sequence 51

<400> SEQUENCE: 51
ctccctcaaa agtggtgctc                                          20

<210> SEQ ID NO 52
<211> LENGTH: 21
<212> TYPE: DNA
<213> ORGANISM: Artificial Sequence
<220> FEATURE:
<223> OTHER INFORMATION: Primer sequence 52

<400> SEQUENCE: 52
ctccctcaaa agtggtgctt a                                        21

<210> SEQ ID NO 53
<211> LENGTH: 20
<212> TYPE: DNA
<213> ORGANISM: Artificial Sequence
<220> FEATURE:
<223> OTHER INFORMATION: Primer sequence 53

<400> SEQUENCE: 53
gtccacctga acactatgtt                                          20

<210> SEQ ID NO 54
<211> LENGTH: 21
<212> TYPE: DNA
<213> ORGANISM: Artificial Sequence
<220> FEATURE:
<223> OTHER INFORMATION: Primer sequence 54

<400> SEQUENCE: 54
gtccacctga acactatgtt c                                        21

<210> SEQ ID NO 55
<211> LENGTH: 22
<212> TYPE: DNA
<213> ORGANISM: Artificial Sequence
<220> FEATURE:
<223> OTHER INFORMATION: Primer sequence 55

<400> SEQUENCE: 55
gtccacctga acactatgtt ta                                       22

<210> SEQ ID NO 56
<211> LENGTH: 18
<212> TYPE: DNA
<213> ORGANISM: Artificial Sequence
<220> FEATURE:
<223> OTHER INFORMATION: Primer sequence 56

<400> SEQUENCE: 56
gctaaacatg agtggggt                                            18

<210> SEQ ID NO 57
<211> LENGTH: 19
<212> TYPE: DNA
<213> ORGANISM: Artificial Sequence
<220> FEATURE:
<223> OTHER INFORMATION: Primer sequence 57

<400> SEQUENCE: 57
gctaaacatg agtggggtc                                           19

```
<210> SEQ ID NO 58
<211> LENGTH: 21
<212> TYPE: DNA
<213> ORGANISM: Artificial Sequence
<220> FEATURE:
<223> OTHER INFORMATION: Primer sequence 58

<400> SEQUENCE: 58
gctaaacatg agtggggtat c                                              21

<210> SEQ ID NO 59
<211> LENGTH: 20
<212> TYPE: DNA
<213> ORGANISM: Artificial Sequence
<220> FEATURE:
<223> OTHER INFORMATION: Primer sequence 59

<400> SEQUENCE: 59
ctcaaacagc tcaaaccaag                                                20

<210> SEQ ID NO 60
<211> LENGTH: 21
<212> TYPE: DNA
<213> ORGANISM: Artificial Sequence
<220> FEATURE:
<223> OTHER INFORMATION: Primer sequence 60

<400> SEQUENCE: 60
ctcaaacagc tcaaaccaag c                                              21

<210> SEQ ID NO 61
<211> LENGTH: 22
<212> TYPE: DNA
<213> ORGANISM: Artificial Sequence
<220> FEATURE:
<223> OTHER INFORMATION: Primer sequence 61

<400> SEQUENCE: 61
ctcaaacagc tcaaaccaag tg                                             22

<210> SEQ ID NO 62
<211> LENGTH: 20
<212> TYPE: DNA
<213> ORGANISM: Artificial Sequence
<220> FEATURE:
<223> OTHER INFORMATION: Primer sequence 62

<400> SEQUENCE: 62
tgcttaggtc cactttctct                                                20

<210> SEQ ID NO 63
<211> LENGTH: 21
<212> TYPE: DNA
<213> ORGANISM: Artificial Sequence
<220> FEATURE:
<223> OTHER INFORMATION: Primer sequence 63

<400> SEQUENCE: 63
tgcttaggtc cactttctct c                                              21

<210> SEQ ID NO 64
<211> LENGTH: 25
<212> TYPE: DNA
<213> ORGANISM: Artificial Sequence
<220> FEATURE:
<223> OTHER INFORMATION: Primer sequence 64
```

```
<400> SEQUENCE: 64
tgcttaggtc cactttctct ttttt                                          25

<210> SEQ ID NO 65
<211> LENGTH: 19
<212> TYPE: DNA
<213> ORGANISM: Artificial Sequence
<220> FEATURE:
<223> OTHER INFORMATION: Primer sequence 65

<400> SEQUENCE: 65
cctgctgaaa atgactgaa                                                 19

<210> SEQ ID NO 66
<211> LENGTH: 20
<212> TYPE: DNA
<213> ORGANISM: Artificial Sequence
<220> FEATURE:
<223> OTHER INFORMATION: Primer sequence 66

<400> SEQUENCE: 66
tatgaaaatg gtcagagaaa                                                20

<210> SEQ ID NO 67
<211> LENGTH: 20
<212> TYPE: DNA
<213> ORGANISM: Artificial Sequence
<220> FEATURE:
<223> OTHER INFORMATION: Primer sequence 67

<400> SEQUENCE: 67
aacttgtggt agttggagct                                                20

<210> SEQ ID NO 68
<211> LENGTH: 22
<212> TYPE: DNA
<213> ORGANISM: Artificial Sequence
<220> FEATURE:
<223> OTHER INFORMATION: Primer sequence 68

<400> SEQUENCE: 68
aacttgtggt agttggagct gg                                             22

<210> SEQ ID NO 69
<211> LENGTH: 21
<212> TYPE: DNA
<213> ORGANISM: Artificial Sequence
<220> FEATURE:
<223> OTHER INFORMATION: Primer sequence 69

<400> SEQUENCE: 69
aacttgtggt agttggagct a                                              21

<210> SEQ ID NO 70
<211> LENGTH: 22
<212> TYPE: DNA
<213> ORGANISM: Artificial Sequence
<220> FEATURE:
<223> OTHER INFORMATION: Primer sequence 70

<400> SEQUENCE: 70
aacttgtggt agttggagct gg                                             22

<210> SEQ ID NO 71
<211> LENGTH: 21
```

```
<212> TYPE: DNA
<213> ORGANISM: Artificial Sequence
<220> FEATURE:
<223> OTHER INFORMATION: Primer sequence 71

<400> SEQUENCE: 71
aacttgtggt agttggagct c                                              21

<210> SEQ ID NO 72
<211> LENGTH: 23
<212> TYPE: DNA
<213> ORGANISM: Artificial Sequence
<220> FEATURE:
<223> OTHER INFORMATION: Primer sequence 72

<400> SEQUENCE: 72
aacttgtggt agttggagct ggt                                            23

<210> SEQ ID NO 73
<211> LENGTH: 21
<212> TYPE: DNA
<213> ORGANISM: Artificial Sequence
<220> FEATURE:
<223> OTHER INFORMATION: Primer sequence 73

<400> SEQUENCE: 73
aacttgtggt agttggagct t                                              21

<210> SEQ ID NO 74
<211> LENGTH: 18
<212> TYPE: DNA
<213> ORGANISM: Artificial Sequence
<220> FEATURE:
<223> OTHER INFORMATION: Primer sequence 74

<400> SEQUENCE: 74
ggcactttgc ctacgcca                                                  18

<210> SEQ ID NO 75
<211> LENGTH: 20
<212> TYPE: DNA
<213> ORGANISM: Artificial Sequence
<220> FEATURE:
<223> OTHER INFORMATION: Primer sequence 75

<400> SEQUENCE: 75
ggcactttgc ctacgccacc                                                20

<210> SEQ ID NO 76
<211> LENGTH: 19
<212> TYPE: DNA
<213> ORGANISM: Artificial Sequence
<220> FEATURE:
<223> OTHER INFORMATION: Primer sequence 76

<400> SEQUENCE: 76
ggcactttgc ctacgccat                                                 19

<210> SEQ ID NO 77
<211> LENGTH: 20
<212> TYPE: DNA
<213> ORGANISM: Artificial Sequence
<220> FEATURE:
<223> OTHER INFORMATION: Primer sequence 77

<400> SEQUENCE: 77
```

```
ggcactttgc ctacgccacc                                              20

<210> SEQ ID NO 78
<211> LENGTH: 19
<212> TYPE: DNA
<213> ORGANISM: Artificial Sequence
<220> FEATURE:
<223> OTHER INFORMATION: Primer sequence 78

<400> SEQUENCE: 78
ggcactttgc ctacgccag                                               19

<210> SEQ ID NO 79
<211> LENGTH: 23
<212> TYPE: DNA
<213> ORGANISM: Artificial Sequence
<220> FEATURE:
<223> OTHER INFORMATION: Primer sequence 79

<400> SEQUENCE: 79
acttgtggta gttggagctg cca                                          23

<210> SEQ ID NO 80
<211> LENGTH: 21
<212> TYPE: DNA
<213> ORGANISM: Artificial Sequence
<220> FEATURE:
<223> OTHER INFORMATION: Primer sequence 80

<400> SEQUENCE: 80
acttgtggta gttggagctg a                                            21

<210> SEQ ID NO 81
<211> LENGTH: 17
<212> TYPE: DNA
<213> ORGANISM: Artificial Sequence
<220> FEATURE:
<223> OTHER INFORMATION: Primer sequence 81

<400> SEQUENCE: 81
aaggcacttt gcctacg                                                 17

<210> SEQ ID NO 82
<211> LENGTH: 19
<212> TYPE: DNA
<213> ORGANISM: Artificial Sequence
<220> FEATURE:
<223> OTHER INFORMATION: Primer sequence 82

<400> SEQUENCE: 82
aaggcacttt gcctacgcc                                               19

<210> SEQ ID NO 83
<211> LENGTH: 18
<212> TYPE: DNA
<213> ORGANISM: Artificial Sequence
<220> FEATURE:
<223> OTHER INFORMATION: Primer sequence 83

<400> SEQUENCE: 83
aaggcacttt gcctacgg                                                18

<210> SEQ ID NO 84
<211> LENGTH: 19
<212> TYPE: DNA
<213> ORGANISM: Artificial Sequence
```

```
<220> FEATURE:
<223> OTHER INFORMATION: Primer sequence 84

<400> SEQUENCE: 84
aaggcacttt gcctacgcc                                                    19

<210> SEQ ID NO 85
<211> LENGTH: 18
<212> TYPE: DNA
<213> ORGANISM: Artificial Sequence
<220> FEATURE:
<223> OTHER INFORMATION: Primer sequence 85

<400> SEQUENCE: 85
aaggcacttt gcctacgt                                                     18

<210> SEQ ID NO 86
<211> LENGTH: 20
<212> TYPE: DNA
<213> ORGANISM: Artificial Sequence
<220> FEATURE:
<223> OTHER INFORMATION: Primer sequence 86

<400> SEQUENCE: 86
aaggcacttt gcctacgcca                                                   20

<210> SEQ ID NO 87
<211> LENGTH: 18
<212> TYPE: DNA
<213> ORGANISM: Artificial Sequence
<220> FEATURE:
<223> OTHER INFORMATION: Primer sequence 87

<400> SEQUENCE: 87
aaggcacttt gcctacga                                                     18

<210> SEQ ID NO 88
<211> LENGTH: 16
<212> TYPE: DNA
<213> ORGANISM: Artificial Sequence
<220> FEATURE:
<223> OTHER INFORMATION: Primer sequence 88

<400> SEQUENCE: 88
ccatctacaa gcagtc                                                       16

<210> SEQ ID NO 89
<211> LENGTH: 18
<212> TYPE: DNA
<213> ORGANISM: Artificial Sequence
<220> FEATURE:
<223> OTHER INFORMATION: Primer sequence 89

<400> SEQUENCE: 89
cagacctaag agcaatca                                                     18

<210> SEQ ID NO 90
<211> LENGTH: 18
<212> TYPE: DNA
<213> ORGANISM: Artificial Sequence
<220> FEATURE:
<223> OTHER INFORMATION: Primer sequence 90

<400> SEQUENCE: 90
taccaccatc cactacaa                                                     18
```

```
<210> SEQ ID NO 91
<211> LENGTH: 17
<212> TYPE: DNA
<213> ORGANISM: Artificial Sequence
<220> FEATURE:
<223> OTHER INFORMATION: Primer sequence 91

<400> SEQUENCE: 91
taccttcttt agccatt                                                    17

<210> SEQ ID NO 92
<211> LENGTH: 20
<212> TYPE: DNA
<213> ORGANISM: Artificial Sequence
<220> FEATURE:
<223> OTHER INFORMATION: Primer sequence 92

<400> SEQUENCE: 92
ctgcctcttg cttctctttt                                                 20

<210> SEQ ID NO 93
<211> LENGTH: 13
<212> TYPE: DNA
<213> ORGANISM: Artificial Sequence
<220> FEATURE:
<223> OTHER INFORMATION: Primer sequence 93

<400> SEQUENCE: 93
tgcttgctta cct                                                        13

<210> SEQ ID NO 94
<211> LENGTH: 20
<212> TYPE: DNA
<213> ORGANISM: Artificial Sequence
<220> FEATURE:
<223> OTHER INFORMATION: Primer sequence 94

<400> SEQUENCE: 94
catgacggag gttgtgaggc                                                 20

<210> SEQ ID NO 95
<211> LENGTH: 21
<212> TYPE: DNA
<213> ORGANISM: Artificial Sequence
<220> FEATURE:
<223> OTHER INFORMATION: Primer sequence 95

<400> SEQUENCE: 95
catgacggag gttgtgaggc g                                               21

<210> SEQ ID NO 96
<211> LENGTH: 24
<212> TYPE: DNA
<213> ORGANISM: Artificial Sequence
<220> FEATURE:
<223> OTHER INFORMATION: Primer sequence 96

<400> SEQUENCE: 96
catgacggag gttgtgaggc actg                                            24

<210> SEQ ID NO 97
<211> LENGTH: 24
<212> TYPE: DNA
<213> ORGANISM: Artificial Sequence
<220> FEATURE:
<223> OTHER INFORMATION: Primer sequence 97
```

-continued

<400> SEQUENCE: 97
catgacggag gttgtgaggc tctg                                        24

<210> SEQ ID NO 98
<211> LENGTH: 20
<212> TYPE: DNA
<213> ORGANISM: Artificial Sequence
<220> FEATURE:
<223> OTHER INFORMATION: Primer sequence 98

<400> SEQUENCE: 98
ggatgggcct cggttcatgc                                             20

<210> SEQ ID NO 99
<211> LENGTH: 21
<212> TYPE: DNA
<213> ORGANISM: Artificial Sequence
<220> FEATURE:
<223> OTHER INFORMATION: Primer sequence 99

<400> SEQUENCE: 99
ggatgggcct cggttcatgc c                                           21

<210> SEQ ID NO 100
<211> LENGTH: 23
<212> TYPE: DNA
<213> ORGANISM: Artificial Sequence
<220> FEATURE:
<223> OTHER INFORMATION: Primer sequence 100

<400> SEQUENCE: 100
ggatgggcct cggttcatgc agc                                         23

<210> SEQ ID NO 101
<211> LENGTH: 23
<212> TYPE: DNA
<213> ORGANISM: Artificial Sequence
<220> FEATURE:
<223> OTHER INFORMATION: Primer sequence 101

<400> SEQUENCE: 101
ggatgggcct cggttcatgc tgc                                         23

<210> SEQ ID NO 102
<211> LENGTH: 21
<212> TYPE: DNA
<213> ORGANISM: Artificial Sequence
<220> FEATURE:
<223> OTHER INFORMATION: Primer sequence 102

<400> SEQUENCE: 102
gtaacagttc ctgcatgggc g                                           21

<210> SEQ ID NO 103
<211> LENGTH: 22
<212> TYPE: DNA
<213> ORGANISM: Artificial Sequence
<220> FEATURE:
<223> OTHER INFORMATION: Primer sequence 103

<400> SEQUENCE: 103
gtaacagttc ctgcatgggc gg                                          22

<210> SEQ ID NO 104

<210> SEQ ID NO 104
<211> LENGTH: 26
<212> TYPE: DNA
<213> ORGANISM: Artificial Sequence
<220> FEATURE:
<223> OTHER INFORMATION: Primer sequence 104

<400> SEQUENCE: 104
gtaacagttc ctgcatgggc gacatg                                    26

<210> SEQ ID NO 105
<211> LENGTH: 26
<212> TYPE: DNA
<213> ORGANISM: Artificial Sequence
<220> FEATURE:
<223> OTHER INFORMATION: Primer sequence 105

<400> SEQUENCE: 105
gtaacagttc ctgcatgggc gtcatg                                    26

<210> SEQ ID NO 106
<211> LENGTH: 20
<212> TYPE: DNA
<213> ORGANISM: Artificial Sequence
<220> FEATURE:
<223> OTHER INFORMATION: Primer sequence 106

<400> SEQUENCE: 106
cctgcatggg cggcatgaac                                           20

<210> SEQ ID NO 107
<211> LENGTH: 21
<212> TYPE: DNA
<213> ORGANISM: Artificial Sequence
<220> FEATURE:
<223> OTHER INFORMATION: Primer sequence 107

<400> SEQUENCE: 107
cctgcatggg cggcatgaac c                                         21

<210> SEQ ID NO 108
<211> LENGTH: 23
<212> TYPE: DNA
<213> ORGANISM: Artificial Sequence
<220> FEATURE:
<223> OTHER INFORMATION: Primer sequence 108

<400> SEQUENCE: 108
cctgcatggg cggcatgaac tgg                                       23

<210> SEQ ID NO 109
<211> LENGTH: 19
<212> TYPE: DNA
<213> ORGANISM: Artificial Sequence
<220> FEATURE:
<223> OTHER INFORMATION: Primer sequence 109

<400> SEQUENCE: 109
gatggtgagg atgggcctc                                            19

<210> SEQ ID NO 110
<211> LENGTH: 20
<212> TYPE: DNA
<213> ORGANISM: Artificial Sequence
<220> FEATURE:
<223> OTHER INFORMATION: Primer sequence 110

<400> SEQUENCE: 110

-continued

```
gatggtgagg atgggcctcc                                              20

<210> SEQ ID NO 111
<211> LENGTH: 25
<212> TYPE: DNA
<213> ORGANISM: Artificial Sequence
<220> FEATURE:
<223> OTHER INFORMATION: Primer sequence 111

<400> SEQUENCE: 111
gatggtgagg atgggcctct ggttc                                        25

<210> SEQ ID NO 112
<211> LENGTH: 18
<212> TYPE: DNA
<213> ORGANISM: Artificial Sequence
<220> FEATURE:
<223> OTHER INFORMATION: Primer sequence 112

<400> SEQUENCE: 112
gacggaacag ctttgagg                                                18

<210> SEQ ID NO 113
<211> LENGTH: 19
<212> TYPE: DNA
<213> ORGANISM: Artificial Sequence
<220> FEATURE:
<223> OTHER INFORMATION: Primer sequence 113

<400> SEQUENCE: 113
gacggaacag ctttgaggc                                               19

<210> SEQ ID NO 114
<211> LENGTH: 21
<212> TYPE: DNA
<213> ORGANISM: Artificial Sequence
<220> FEATURE:
<223> OTHER INFORMATION: Primer sequence 114

<400> SEQUENCE: 114
gacggaacag ctttgaggag c                                            21

<210> SEQ ID NO 115
<211> LENGTH: 21
<212> TYPE: DNA
<213> ORGANISM: Artificial Sequence
<220> FEATURE:
<223> OTHER INFORMATION: Primer sequence 115

<400> SEQUENCE: 115
gacggaacag ctttgaggtg c                                            21

<210> SEQ ID NO 116
<211> LENGTH: 20
<212> TYPE: DNA
<213> ORGANISM: Artificial Sequence
<220> FEATURE:
<223> OTHER INFORMATION: Primer sequence 116

<400> SEQUENCE: 116
acggaacagc tttgaggtgc                                              20

<210> SEQ ID NO 117
<211> LENGTH: 21
<212> TYPE: DNA
```

```
<213> ORGANISM: Artificial Sequence
<220> FEATURE:
<223> OTHER INFORMATION: Primer sequence 117

<400> SEQUENCE: 117
acggaacagc tttgaggtgc g                                          21

<210> SEQ ID NO 118
<211> LENGTH: 23
<212> TYPE: DNA
<213> ORGANISM: Artificial Sequence
<220> FEATURE:
<223> OTHER INFORMATION: Primer sequence 118

<400> SEQUENCE: 118
acggaacagc tttgaggtgc atg                                        23

<210> SEQ ID NO 119
<211> LENGTH: 20
<212> TYPE: DNA
<213> ORGANISM: Artificial Sequence
<220> FEATURE:
<223> OTHER INFORMATION: Primer sequence 119

<400> SEQUENCE: 119
gtgcctgtcc tgggagagac                                            20

<210> SEQ ID NO 120
<211> LENGTH: 21
<212> TYPE: DNA
<213> ORGANISM: Artificial Sequence
<220> FEATURE:
<223> OTHER INFORMATION: Primer sequence 120

<400> SEQUENCE: 120
gtgcctgtcc tgggagagac c                                          21

<210> SEQ ID NO 121
<211> LENGTH: 24
<212> TYPE: DNA
<213> ORGANISM: Artificial Sequence
<220> FEATURE:
<223> OTHER INFORMATION: Primer sequence 121

<400> SEQUENCE: 121
gtgcctgtcc tgggagagac tggc                                       24

<210> SEQ ID NO 122
<211> LENGTH: 20
<212> TYPE: DNA
<213> ORGANISM: Artificial Sequence
<220> FEATURE:
<223> OTHER INFORMATION: Primer sequence 122

<400> SEQUENCE: 122
aacttgtggt agttggagct                                            20

<210> SEQ ID NO 123
<211> LENGTH: 20
<212> TYPE: DNA
<213> ORGANISM: Artificial Sequence
<220> FEATURE:
<223> OTHER INFORMATION: Primer sequence 123

<400> SEQUENCE: 123
acttgtggta gttggagctg                                            20
```

```
<210> SEQ ID NO 124
<211> LENGTH: 20
<212> TYPE: DNA
<213> ORGANISM: Artificial Sequence
<220> FEATURE:
<223> OTHER INFORMATION: Primer sequence 124

<400> SEQUENCE: 124
tgtggtagtt ggagctggtg                                                    20

<210> SEQ ID NO 125
<211> LENGTH: 17
<212> TYPE: DNA
<213> ORGANISM: Artificial Sequence
<220> FEATURE:
<223> OTHER INFORMATION: Primer sequence 125

<400> SEQUENCE: 125
aaatagcaga aataaaa                                                       17

<210> SEQ ID NO 126
<211> LENGTH: 20
<212> TYPE: DNA
<213> ORGANISM: Artificial Sequence
<220> FEATURE:
<223> OTHER INFORMATION: Primer sequence 126

<400> SEQUENCE: 126
tccaatcttt tcttttattt                                                    20

<210> SEQ ID NO 127
<211> LENGTH: 20
<212> TYPE: DNA
<213> ORGANISM: Artificial Sequence
<220> FEATURE:
<223> OTHER INFORMATION: Primer sequence 127

<400> SEQUENCE: 127
atcttcagct gacctagttc                                                    20

<210> SEQ ID NO 128
<211> LENGTH: 20
<212> TYPE: DNA
<213> ORGANISM: Artificial Sequence
<220> FEATURE:
<223> OTHER INFORMATION: Primer sequence 128

<400> SEQUENCE: 128
ctccctccaa aagtggtgct                                                    20

<210> SEQ ID NO 129
<211> LENGTH: 20
<212> TYPE: DNA
<213> ORGANISM: Artificial Sequence
<220> FEATURE:
<223> OTHER INFORMATION: Primer sequence 129

<400> SEQUENCE: 129
gtccacctgt acactatgtt                                                    20

<210> SEQ ID NO 130
<211> LENGTH: 20
<212> TYPE: DNA
<213> ORGANISM: Artificial Sequence
<220> FEATURE:
```

<223> OTHER INFORMATION: Primer sequence 130

<400> SEQUENCE: 130
cctaaacata agtgggtct                                              20

<210> SEQ ID NO 131
<211> LENGTH: 20
<212> TYPE: DNA
<213> ORGANISM: Artificial Sequence
<220> FEATURE:
<223> OTHER INFORMATION: Primer sequence 131

<400> SEQUENCE: 131
ctcaaacagc acaaaccaag                                             20

<210> SEQ ID NO 132
<211> LENGTH: 20
<212> TYPE: DNA
<213> ORGANISM: Artificial Sequence
<220> FEATURE:
<223> OTHER INFORMATION: Primer sequence 132

<400> SEQUENCE: 132
tgcttaggcc cactttctct                                             20

<210> SEQ ID NO 133
<211> LENGTH: 20
<212> TYPE: DNA
<213> ORGANISM: Artificial Sequence
<220> FEATURE:
<223> OTHER INFORMATION: Primer sequence 133

<400> SEQUENCE: 133
catgacggag gttgtgaggc                                             20

<210> SEQ ID NO 134
<211> LENGTH: 20
<212> TYPE: DNA
<213> ORGANISM: Artificial Sequence
<220> FEATURE:
<223> OTHER INFORMATION: Primer sequence 134

<400> SEQUENCE: 134
gtaacagttc ctgcatgggc                                             20

<210> SEQ ID NO 135
<211> LENGTH: 20
<212> TYPE: DNA
<213> ORGANISM: Artificial Sequence
<220> FEATURE:
<223> OTHER INFORMATION: Primer sequence 135

<400> SEQUENCE: 135
taacagttcc tgcatgggcg                                             20

<210> SEQ ID NO 136
<211> LENGTH: 20
<212> TYPE: DNA
<213> ORGANISM: Artificial Sequence
<220> FEATURE:
<223> OTHER INFORMATION: Primer sequence 136

<400> SEQUENCE: 136
cctgcatggg cggcatgaac                                             20

```
<210> SEQ ID NO 137
<211> LENGTH: 20
<212> TYPE: DNA
<213> ORGANISM: Artificial Sequence
<220> FEATURE:
<223> OTHER INFORMATION: Primer sequence 137

<400> SEQUENCE: 137
ctgcatgggc ggcatgaacc                                                 20

<210> SEQ ID NO 138
<211> LENGTH: 20
<212> TYPE: DNA
<213> ORGANISM: Artificial Sequence
<220> FEATURE:
<223> OTHER INFORMATION: Primer sequence 138

<400> SEQUENCE: 138
gacggaacag ctttgaggtg                                                 20

<210> SEQ ID NO 139
<211> LENGTH: 20
<212> TYPE: DNA
<213> ORGANISM: Artificial Sequence
<220> FEATURE:
<223> OTHER INFORMATION: Primer sequence 139

<400> SEQUENCE: 139
acggaacagc tttgaggtgc                                                 20

<210> SEQ ID NO 140
<211> LENGTH: 20
<212> TYPE: DNA
<213> ORGANISM: Artificial Sequence
<220> FEATURE:
<223> OTHER INFORMATION: Primer sequence 140

<400> SEQUENCE: 140
gtgcctatcc tgggagagac                                                 20

<210> SEQ ID NO 141
<211> LENGTH: 20
<212> TYPE: DNA
<213> ORGANISM: Artificial Sequence
<220> FEATURE:
<223> OTHER INFORMATION: Primer sequence 141

<400> SEQUENCE: 141
gcccttaacc tttttcaggt                                                 20

<210> SEQ ID NO 142
<211> LENGTH: 20
<212> TYPE: DNA
<213> ORGANISM: Artificial Sequence
<220> FEATURE:
<223> OTHER INFORMATION: Primer sequence 142

<400> SEQUENCE: 142
ggtggagatc tgcaaacctc                                                 20

<210> SEQ ID NO 143
<211> LENGTH: 20
<212> TYPE: DNA
<213> ORGANISM: Artificial Sequence
<220> FEATURE:
<223> OTHER INFORMATION: Primer sequence 143
```

```
<400> SEQUENCE: 143
agagaaagag gcagaaaaaa                                              20

<210> SEQ ID NO 144
<211> LENGTH: 40
<212> TYPE: DNA
<213> ORGANISM: Artificial Sequence
<220> FEATURE:
<223> OTHER INFORMATION: Primer sequence 144

<400> SEQUENCE: 144
gcggtcccaa aagggtcagt cacctccacc acctcctcaa                        40

<210> SEQ ID NO 145
<211> LENGTH: 39
<212> TYPE: DNA
<213> ORGANISM: Artificial Sequence
<220> FEATURE:
<223> OTHER INFORMATION: Primer sequence 145

<400> SEQUENCE: 145
gcggtcccaa aagggtcagt gtatcagcat ctggaagaa                         39

<210> SEQ ID NO 146
<211> LENGTH: 38
<212> TYPE: DNA
<213> ORGANISM: Artificial Sequence
<220> FEATURE:
<223> OTHER INFORMATION: Primer sequence 146

<400> SEQUENCE: 146
gcggtcccaa aaggtcagtc atcatcatct gaatcatc                          38

<210> SEQ ID NO 147
<211> LENGTH: 40
<212> TYPE: DNA
<213> ORGANISM: Artificial Sequence
<220> FEATURE:
<223> OTHER INFORMATION: Primer sequence 147

<400> SEQUENCE: 147
gcggtcccat aagggtcagt tcacctgact gtgctcctcc                        40

<210> SEQ ID NO 148
<211> LENGTH: 41
<212> TYPE: DNA
<213> ORGANISM: Artificial Sequence
<220> FEATURE:
<223> OTHER INFORMATION: Primer sequence 148

<400> SEQUENCE: 148
gcggtcccta aagggtcagt ttggctgctt tgcaatagct t                      41

<210> SEQ ID NO 149
<211> LENGTH: 41
<212> TYPE: DNA
<213> ORGANISM: Artificial Sequence
<220> FEATURE:
<223> OTHER INFORMATION: Primer sequence 149

<400> SEQUENCE: 149
gcggtcccat aagggtcagt ttggcattgc ggagcttata c                      41

<210> SEQ ID NO 150
<211> LENGTH: 40
```

<212> TYPE: DNA
<213> ORGANISM: Artificial Sequence
<220> FEATURE:
<223> OTHER INFORMATION: Primer sequence 150

<400> SEQUENCE: 150
gcggtcccaa aagggtcagt ggcttaattc tgatttcaca           40

<210> SEQ ID NO 151
<211> LENGTH: 37
<212> TYPE: DNA
<213> ORGANISM: Artificial Sequence
<220> FEATURE:
<223> OTHER INFORMATION: Primer sequence 151

<400> SEQUENCE: 151
gcggtcccaa aagggtcagt ccatctacaa gcagtca              37

<210> SEQ ID NO 152
<211> LENGTH: 38
<212> TYPE: DNA
<213> ORGANISM: Artificial Sequence
<220> FEATURE:
<223> OTHER INFORMATION: Primer sequence 152

<400> SEQUENCE: 152
gcggtcccaa aagggtcagt cagacctaag agcaatca             38

<210> SEQ ID NO 153
<211> LENGTH: 40
<212> TYPE: DNA
<213> ORGANISM: Artificial Sequence
<220> FEATURE:
<223> OTHER INFORMATION: Primer sequence 153

<400> SEQUENCE: 153
gcggtcccaa aagggtcagt cccatttact ttgcacatct           40

<210> SEQ ID NO 154
<211> LENGTH: 37
<212> TYPE: DNA
<213> ORGANISM: Artificial Sequence
<220> FEATURE:
<223> OTHER INFORMATION: Primer sequence 154

<400> SEQUENCE: 154
gcggtcccaa aagggtcagt cccatgcagg aactgtt              37

<210> SEQ ID NO 155
<211> LENGTH: 39
<212> TYPE: DNA
<213> ORGANISM: Artificial Sequence
<220> FEATURE:
<223> OTHER INFORMATION: Primer sequence 155

<400> SEQUENCE: 155
gcggtcccaa aagggtcaga gtatggaaga aatcggtaa            39

<210> SEQ ID NO 156
<211> LENGTH: 40
<212> TYPE: DNA
<213> ORGANISM: Artificial Sequence
<220> FEATURE:
<223> OTHER INFORMATION: Primer sequence 156

<400> SEQUENCE: 156

-continued gcggtcccaa aagggtcagt agcatctgta tcaggcaaag    40

<210> SEQ ID NO 157
<211> LENGTH: 38
<212> TYPE: DNA
<213> ORGANISM: Artificial Sequence
<220> FEATURE:
<223> OTHER INFORMATION: Primer sequence 157

<400> SEQUENCE: 157
gcggtccgaa aagggtcagt gggcaacaga gcaagatg    38

<210> SEQ ID NO 158
<211> LENGTH: 37
<212> TYPE: DNA
<213> ORGANISM: Artificial Sequence
<220> FEATURE:
<223> OTHER INFORMATION: Primer sequence 158

<400> SEQUENCE: 158
cagatagccc tggacaaacc atgccaccaa gcagaag    37

<210> SEQ ID NO 159
<211> LENGTH: 37
<212> TYPE: DNA
<213> ORGANISM: Artificial Sequence
<220> FEATURE:
<223> OTHER INFORMATION: Primer sequence 159

<400> SEQUENCE: 159
tactcccctg ccctcaacaa gatgttttgc caactgg    37

<210> SEQ ID NO 160
<211> LENGTH: 21
<212> TYPE: DNA
<213> ORGANISM: Artificial Sequence
<220> FEATURE:
<223> OTHER INFORMATION: Primer sequence 160

<400> SEQUENCE: 160
aacttgtggt agttggagct t    21

<210> SEQ ID NO 161
<211> LENGTH: 21
<212> TYPE: DNA
<213> ORGANISM: Artificial Sequence
<220> FEATURE:
<223> OTHER INFORMATION: Primer sequence 161

<400> SEQUENCE: 161
aacttgtggt agttggagct g    21

<210> SEQ ID NO 162
<211> LENGTH: 21
<212> TYPE: DNA
<213> ORGANISM: Artificial Sequence
<220> FEATURE:
<223> OTHER INFORMATION: Primer sequence 162

<400> SEQUENCE: 162
aacttgtggt agttggagct c    21

<210> SEQ ID NO 163
<211> LENGTH: 20
<212> TYPE: DNA
<213> ORGANISM: Artificial Sequence

```
<220> FEATURE:
<223> OTHER INFORMATION: Primer sequence 163

<400> SEQUENCE: 163
aacttgtggt agttggagct                                              20

<210> SEQ ID NO 164
<211> LENGTH: 20
<212> TYPE: DNA
<213> ORGANISM: Artificial Sequence
<220> FEATURE:
<223> OTHER INFORMATION: Primer sequence 164

<400> SEQUENCE: 164
acttgtggta gttggagctg                                              20

<210> SEQ ID NO 165
<211> LENGTH: 20
<212> TYPE: DNA
<213> ORGANISM: Artificial Sequence
<220> FEATURE:
<223> OTHER INFORMATION: Primer sequence 165

<400> SEQUENCE: 165
tgtggtagtt ggagctggtg                                              20

<210> SEQ ID NO 166
<211> LENGTH: 17
<212> TYPE: DNA
<213> ORGANISM: Artificial Sequence
<220> FEATURE:
<223> OTHER INFORMATION: Primer sequence 166

<400> SEQUENCE: 166
aaatagcaga aataaaa                                                 17

<210> SEQ ID NO 167
<211> LENGTH: 17
<212> TYPE: DNA
<213> ORGANISM: Artificial Sequence
<220> FEATURE:
<223> OTHER INFORMATION: Primer sequence 167

<400> SEQUENCE: 167
aaatagcaga aataaaa                                                 17

<210> SEQ ID NO 168
<211> LENGTH: 20
<212> TYPE: DNA
<213> ORGANISM: Artificial Sequence
<220> FEATURE:
<223> OTHER INFORMATION: Primer sequence 168

<400> SEQUENCE: 168
tccaatcttt tcttttattt                                              20

<210> SEQ ID NO 169
<211> LENGTH: 20
<212> TYPE: DNA
<213> ORGANISM: Artificial Sequence
<220> FEATURE:
<223> OTHER INFORMATION: Primer sequence 169

<400> SEQUENCE: 169
atcttcagct gacctagttc                                              20
```

<210> SEQ ID NO 170
<211> LENGTH: 20
<212> TYPE: DNA
<213> ORGANISM: Artificial Sequence
<220> FEATURE:
<223> OTHER INFORMATION: Primer sequence 170

<400> SEQUENCE: 170
ctccctccaa aagtggtgct                                                    20

<210> SEQ ID NO 171
<211> LENGTH: 20
<212> TYPE: DNA
<213> ORGANISM: Artificial Sequence
<220> FEATURE:
<223> OTHER INFORMATION: Primer sequence 171

<400> SEQUENCE: 171
gtccacctgt acactatgtt                                                    20

<210> SEQ ID NO 172
<211> LENGTH: 20
<212> TYPE: DNA
<213> ORGANISM: Artificial Sequence
<220> FEATURE:
<223> OTHER INFORMATION: Primer sequence 172

<400> SEQUENCE: 172
gctaaacata agtggggtct                                                    20

<210> SEQ ID NO 173
<211> LENGTH: 20
<212> TYPE: DNA
<213> ORGANISM: Artificial Sequence
<220> FEATURE:
<223> OTHER INFORMATION: Primer sequence 173

<400> SEQUENCE: 173
ctcaaacagc acaaaccaag                                                    20

<210> SEQ ID NO 174
<211> LENGTH: 20
<212> TYPE: DNA
<213> ORGANISM: Artificial Sequence
<220> FEATURE:
<223> OTHER INFORMATION: Primer sequence 174

<400> SEQUENCE: 174
tgcttaggcc cactttctct                                                    20

<210> SEQ ID NO 175
<211> LENGTH: 20
<212> TYPE: DNA
<213> ORGANISM: Artificial Sequence
<220> FEATURE:
<223> OTHER INFORMATION: Primer sequence 175

<400> SEQUENCE: 175
catgacggag gttgtgaggc                                                    20

<210> SEQ ID NO 176
<211> LENGTH: 20
<212> TYPE: DNA
<213> ORGANISM: Artificial Sequence
<220> FEATURE:
<223> OTHER INFORMATION: Primer sequence 176

<400> SEQUENCE: 176
gtaacagttc ctgcatgggc           20

<210> SEQ ID NO 177
<211> LENGTH: 20
<212> TYPE: DNA
<213> ORGANISM: Artificial Sequence
<220> FEATURE:
<223> OTHER INFORMATION: Primer sequence 177

<400> SEQUENCE: 177
taacagttcc tgcatgggcg           20

<210> SEQ ID NO 178
<211> LENGTH: 20
<212> TYPE: DNA
<213> ORGANISM: Artificial Sequence
<220> FEATURE:
<223> OTHER INFORMATION: Primer sequence 178

<400> SEQUENCE: 178
ctgcatgggc ggcatgaacc           20

<210> SEQ ID NO 179
<211> LENGTH: 20
<212> TYPE: DNA
<213> ORGANISM: Artificial Sequence
<220> FEATURE:
<223> OTHER INFORMATION: Primer sequence 179

<400> SEQUENCE: 179
ctgcatgggc ggcatgaacc           20

<210> SEQ ID NO 180
<211> LENGTH: 20
<212> TYPE: DNA
<213> ORGANISM: Artificial Sequence
<220> FEATURE:
<223> OTHER INFORMATION: Primer sequence 180

<400> SEQUENCE: 180
gacggaacag ctttgaggtg           20

<210> SEQ ID NO 181
<211> LENGTH: 20
<212> TYPE: DNA
<213> ORGANISM: Artificial Sequence
<220> FEATURE:
<223> OTHER INFORMATION: Primer sequence 181

<400> SEQUENCE: 181
acggaacagc tttgaggtgc           20

<210> SEQ ID NO 182
<211> LENGTH: 20
<212> TYPE: DNA
<213> ORGANISM: Artificial Sequence
<220> FEATURE:
<223> OTHER INFORMATION: Primer sequence 182

<400> SEQUENCE: 182
gtgcctatcc tgggagagac           20

<210> SEQ ID NO 183

-continued

```
<211> LENGTH: 20
<212> TYPE: DNA
<213> ORGANISM: Artificial Sequence
<220> FEATURE:
<223> OTHER INFORMATION: Primer sequence 183

<400> SEQUENCE: 183
ggtggagatc tgcaaacctc                                                    20

<210> SEQ ID NO 184
<211> LENGTH: 20
<212> TYPE: DNA
<213> ORGANISM: Artificial Sequence
<220> FEATURE:
<223> OTHER INFORMATION: Primer sequence 184

<400> SEQUENCE: 184
agagaaagag gcagaaaaaa                                                    20

<210> SEQ ID NO 185
<211> LENGTH: 20
<212> TYPE: DNA
<213> ORGANISM: Artificial Sequence
<220> FEATURE:
<223> OTHER INFORMATION: Primer sequence 185

<400> SEQUENCE: 185
gcccttaacc tttttcaggt                                                    20
```